(12) United States Patent
Masui et al.

(10) Patent No.: US 8,563,732 B2
(45) Date of Patent: Oct. 22, 2013

(54) OXYIMINO COMPOUNDS AND THE USE THEREOF

(75) Inventors: Moriyasu Masui, Osaka (JP); Hidenori Mikamiyama, Osaka (JP); Naoki Tsuno, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 583 days.

(21) Appl. No.: 12/602,441

(22) PCT Filed: May 30, 2008

(86) PCT No.: PCT/US2008/006888
§ 371 (c)(1),
(2), (4) Date: May 24, 2010

(87) PCT Pub. No.: WO2008/150470
PCT Pub. Date: Dec. 11, 2008

(65) Prior Publication Data
US 2010/0240703 A1    Sep. 23, 2010

Related U.S. Application Data

(60) Provisional application No. 60/924,808, filed on May 31, 2007.

(51) Int. Cl.
*A61K 31/44* (2006.01)
*C07D 211/00* (2006.01)

(52) U.S. Cl.
USPC .......................................... 546/242; 514/335

(58) Field of Classification Search
USPC ....................................................... 546/242
See application file for complete search history.

(56) References Cited

U.S. PATENT DOCUMENTS

| | | | |
|---|---|---|---|
| 3,577,441 A | 5/1971 | Kaminsky et al. | |
| 4,585,785 A | 4/1986 | Walsh et al. | |
| 4,816,452 A * | 3/1989 | Pearson et al. | 514/196 |
| 5,880,138 A | 3/1999 | Heinz et al. | |
| 6,011,035 A | 1/2000 | Snutch et al. | |
| 6,136,839 A | 10/2000 | Isakson et al. | |
| 6,310,059 B1 | 10/2001 | Snutch | |
| 6,340,678 B1 | 1/2002 | Matsuhisa et al. | |
| 6,492,375 B2 | 12/2002 | Snutch | |
| 2001/0029258 A1 | 10/2001 | Snutch | |
| 2003/0199541 A1 | 10/2003 | Lampilas et al. | |
| 2004/0204404 A1 | 10/2004 | Zelle et al. | |
| 2005/0020572 A1 | 1/2005 | Aszodi et al. | |
| 2008/0081825 A1* | 4/2008 | Nakai et al. | 514/318 |
| 2009/0298878 A1 | 12/2009 | Matsumura et al. | |
| 2009/0306136 A1 | 12/2009 | Matsumura et al. | |

FOREIGN PATENT DOCUMENTS

| | | |
|---|---|---|
| CN | 1850823 A | 10/2006 |
| EP | 0 987 264 A1 | 3/2000 |
| EP | 1 307 457 B1 | 4/2004 |
| EP | 1 741 702 A1 | 10/2007 |
| GB | 1 446 980 A | 8/1976 |
| GB | 2 040 933 A | 9/1980 |
| GB | 2 231 048 A | 11/1990 |
| JP | 50-84523 A | 7/1975 |
| JP | S62-59282 | 3/1987 |
| WO | WO 98/39325 A | 9/1998 |
| WO | WO 99/24399 A | 5/1999 |
| WO | WO 99/26926 A | 6/1999 |
| WO | WO 00/35886 A2 | 6/2000 |
| WO | WO 02/10172 A1 | 2/2002 |
| WO | WO 02/057241 A1 | 7/2002 |
| WO | WO 02/074741 A1 | 9/2002 |
| WO | WO 2004/022535 A1 | 3/2004 |
| WO | WO 2004/083167 A1 | 9/2004 |

(Continued)

OTHER PUBLICATIONS

International Search Report from the U.S. Patent and Trademark Office for International Application No. PCT/US2008/06888 (Aug. 29, 2008).

(Continued)

*Primary Examiner* — John Mabry
(74) *Attorney, Agent, or Firm* — Finnegan, Henderson, Farabow, Garrett & Dunner, LLP

(57) ABSTRACT

The invention relates to oxyimino compounds of (Formula I), and pharmaceutically acceptable salts, prodrugs and solvates thereof, wherein: Y is CO or $SO_m$; Z is hydrogen, each optionally substituted lower alkyl, lower alkenyl, aryl, heterocyclyl etc. $R^1$ and $R^2$ are each independently hydrogen, each optionally substituted lower alkyl, lower alkenyl, cycloalkyl, aryl, heterocyclyl etc., each X is independently =O, optionally substituted lower alkyl, cyano, nitro etc., m is 1 or 2, p is 0, 1 or 2 and q is 0 or 1. The invention is also directed to the use compounds of Formula I to treat, prevent or ameliorate a disorder responsive to the blockade of calcium channels, and particularly N-type calcium channels. Compounds of the present invention are especially useful for treating pain.

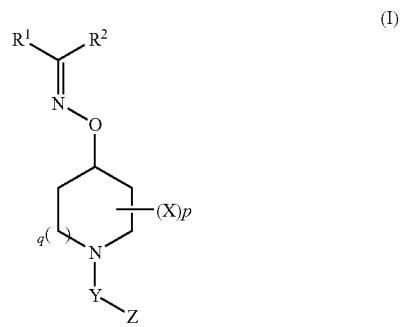

7 Claims, No Drawings

(56) References Cited

FOREIGN PATENT DOCUMENTS

| WO | WO 2004/105750 A1 | 12/2004 |
|---|---|---|
| WO | WO 2005/048933 A2 | 6/2005 |
| WO | WO 2005/097129 A2 | 10/2005 |
| WO | WO 2005/105743 A1 | 11/2005 |
| WO | WO 2006/040181 A2 | 4/2006 |
| WO | WO-2006/122014 A2 | 11/2006 |
| WO | WO 2007/007886 A1 | 1/2007 |
| WO | WO 2007/028638 A1 | 3/2007 |
| WO | WO 2007/085357 A1 | 8/2007 |
| WO | WO 2007/110449 A1 | 10/2007 |
| WO | WO 2007/118853 A1 | 10/2007 |
| WO | WO 2007/118854 A1 | 10/2007 |
| WO | WO 2007/147713 A1 | 12/2007 |
| WO | WO 2008/008398 A2 | 1/2008 |
| WO | WO 2008/124118 A1 | 10/2008 |
| WO | WO 2008/150447 A1 | 12/2008 |
| WO | WO 2008/150470 A1 | 12/2008 |
| WO | WO 2009/040659 A2 | 4/2009 |
| WO | WO 2009/151152 A1 | 12/2009 |
| WO | WO 2010/014257 A2 | 2/2010 |

OTHER PUBLICATIONS

Brower "New paths to pain relief", Nature Biotechnology, vol. 18, (2000), pp. 387-391.
Castellano et al., "Cloning and Expression of a Neuronal Calcium Channel β Subunit", The Journal of Biological Chemistry, vol. 268, No. 17, (1993), pp. 12359-12366.
Cattanach et al., "Preparation of 4a-Alkoxy-1,2,3,4,4a,9b-hexahydro- and -1,2,3,4-tetra-hyro-benzofuro [3,2-c] pyridines", J. Chem. Soc., Section C: Organic, pp. 53-60, (1971).
Davila, "Molecular and Functional Diversity of Voltage-Gated Calcium Channels", Annals of the New York Academy of Sciences, pp. 102-117, (1999).
Dubel et al., "Molecular cloning of the a-1 subunit of an w-conotoxin-sensitive calcium channel", Proc. National Academy of Science, USA, vol. 89, (1992), pp. 5058-5062.
Filer, "Isotopes in the Physical and Biomedical Sciences", Labeled Compounds (Part A), vol. 1, (1987), Chapter 6, pp. 156-192.
Frampton et al., "Approaches to a Scaleable Synthesis of CH8757: A Potent Inhibitor of Matrix Metalloproteinases", Organic Process Research & Development, vol. 8, No. 3, pp. 414-417, (2004).
Halazy et al., Database CAPLUS on STN (Columbus, OH, USA) No. 135:288686, "Synthesis of substituted N-acyl/sulfonyl pyrrolidine derivatives as bax inhibitors" abstract, 3 pages, (2001).
Halazy et al., Database CAPLUS on STN (Columbus, OH, USA) No. 135:303763, "Preparation of pyrrolidnes as inhibitors of Bax function", abstract, 2 pages, (2001).
Hamil et al., "Improved Patch-Clamp Techniques for High-Resolution Current Recording from Cells and Cell-Free Membrane Patches", European Journal of Physiology, (1981), pp. 85-100.
Hanson, "Analgesic, Antipyretic and Anti-inflammatory Drugs", College of Pharmacy and School of Medicine, vol. II, pp. 1196-1122 (1995).
Hu et al., "The Discovery of [1-(4-Dimethylamino-benzyl)-piperdin-4-yl]-[4-(3,3-dimethylbuty1)-phenyl]-(3-methyl-but-2-enyl)-Amine, an N-type Ca$^{+2}$ Channel Blocker with Oral Activity for Analgesia", Bioorganic & Medicinal Chemistry, vol. 8, pp. 1203-1212, (2000).
Hunskaar et al., "Formalin test in mice, a useful technique for evaluating mild analgesics", Journal of Neuroscience Methods, (1985), pp. 69-76.
Insel, "Analgesic-Antipretic and Antiinflammatory Agents and Drugs Employed in the Treatment of Gout", Chapter 27, (1996), pp. 617-657.
International Preliminary Report on Patentability issued Dec. 14, 2010, for PCT/JP2009/061140.
International Preliminary Report on Patentability issued Dec. 1, 2009, for International Application No. PCT/US2008/006855.
International Preliminary Report on Patentability issued Dec. 1, 2009, for PCT/US2008/006888.
International Preliminary Report on Patentability issued Jan. 14, 2009, for International Application No. PCT/US2007/015827.
International Search Report mailed Aug. 29, 2008, for International Application No. PCT/US2008/006855.
International Search Report mailed Aug. 4, 2009, for International Application No. PCT/JP2009/061140.
International Search Report mailed Oct. 7, 2008, for International Application No. PCT/US2007/015827.
Itsuno et al., "Asymmetric Reduction of Chiral Acetophenone Oxime Ethers to Optically Active Primary Amines", Chemistry Letters, pp. 1133-1136 (1986).
Kim, "Rat brain expresses an alternatively spliced form of the dihydropyridine-sensitive L-type calcium channel α2 subunit", Proc. National Academy of Science, USA, vol. 89, (1992), pp. 3251-3255.
Kim et al., "An experimental model for peripheral neuropathy produced by segmental spinal nerve ligation in the rat", Pain 50, (1992), pp. 355-363.
Koch, "cDNA Cloning of a Dihydropyridine-sensitive Calcium Channel from Rat Aorta", The Journal of Biological Chemistry, vol. 265, No. 29, (1990), pp. 17786-17791.
Leeson et al., "Effects of Five-membered Ring Conformation on Bioreceptor Recognition: Identification of 3R-Amino-1-hydroxy-4R-methylpyrrolidin-2-one (L-687,414) as a Potent Glycine/N-Methyl-D-Aspartate Receptor Antagonist", J. Chem. Soc. Chem. Commun., pp. 1578-1580, (1990).
Levine, "Inflammatory pain", Textbook of Pain, $3^{rd}$ Edition, (1994) pp. 45-56.
Lin et al., "Identification of Functionally Distinct Isoforms of the N-Type Ca$^{2+}$ Channel in Rat Sympathetic Ganglia and Brain", Neuron, vol. 18, (1997), pp. 153-166.
McBriar et al., Database CAPLUS on STN (Columbus, OH, USA) No. 137:125084, "Preparation of substituted ureas as MCH antagonists useful in the treatment of obesity", abstract, 2 pages, (2002).
Mori et al., "Synthesis of Carbapenam Skeletons Using a Ruthenium-Catalyzed Cyclization", Organic Letters, vol. 2, No. 20, (2000), pp. 3245-3247.
Phuket et al., "Synthesis and Structure-Activity Studies of Some Antitumor Congeners of ι- -Canaline", Drug Development Research 47, (1999), pp. 170-177.
Pragnell et al., "Cloning and tissue-specific expression of the brain calcium channel β-subunit", Federation of European Biochemical Societies, vol. 291, (1991), pp. 253-258.
Shibata et al., "Preparation of sulfamide derivatives as antitumor agents", Abstract of WO 2004/083167 identified as CAPLUS 2004: 799553 and as Registry No. RN 765958-60-9 (2 pages) entered Oct. 20, 2004.
Smith et al., Database CAPLUS on STN (Columbus, OH, USA) No. 109:38215, "Synthesis and pharmacological activity on angiotensin-converting enzyme inhibitors: N-mercaptoacy1-4-substituted-s-prolines" abstract, 2 pages, (1988).
Song et al., "(S)-4-Methyl-2-(methylamino)pentanoic Acid [4,4-Bis(4-fluorophenyl)butyl]amide Hydrochloride, a Novel Calcium Channel Antagonist, Is Efficacious in Several Animal Models of Pain", Journal of Medicinal Chemistry, vol. 43, No. 19, pp. 3473-3477, (2000).
Stein et al., "Unilateral Inflammation of the Hindpaw in Rats as a Model of Prolonged Noxious Stimulation: Alterations in Behavior and Nociceptive Thresholds", Pharmacology Biochemistry & Behavior, vol. 31, (1988), pp. 445-451.
Tallier et al., "Use of a sterically demanding Lewis acid to direct ring expansion of monoactivated methylenecyclopropanes", Tetrahedron, (2007), pp. 8469-8477.
Vanderesse et al., "α-Aminoxy Acids as Building Blocks for the Oxime and Hydroxylamine Pseudopeptide Links. Application to the Synthesis of Human Elastase Inhibitors", Journal of Peptide Science, vol. 9, pp. 282-299 (2003).
Vanegas et al., "Effects of antagonists to high-threshold calcium channels upon spinal mechanisms of pain, hyperalgesia and allodynia", PAIN, 85, pp. 9-18, (2000).
Wallace, "Calcium and Sodium Channel Antagonists for the Treatment of Pain", The Clinical Journal of Pain, vol. 16, No. 2, pp. S80-S85, (2000).

(56) References Cited

OTHER PUBLICATIONS

Werchan et al., Verlauf und Produkte der Umsetzung von Isocyanaten mit 2,2,6,6-Tetramethylpiperidin-4-onoxim, Journal für Praktische Chemie(Leipzig) 1979, vol. 321(5), p. 865-869.

Yang et al., "A kind of compound quinolines and its preparation method and use comprising hydroxyimino" Machine translation of CN 1850823A, CNIPR, http://english.cnipr.com/enpat/index.htm, 78 pages, (Dec. 11, 2008).

Yang et al., "Preparation of 1,8-naphthyridine derivatives as antibacterial agents", Abstract of CN 1850823, STN Tokyo, CAPLUS 2006: 1129102, entered Oct. 30, 2006.

Zámocká et al., Synthese und carbamoylierung von 4-oximino-2,2,6,6,-tetramethylpiperidin-1-carbon säureestern, Zeitschrift für Chemie, 1980, vol. 20(2), p. 56-57.

European Supplementary Search Report and Search Opinion, mailed Jul. 8, 2011, for European Application No. 07810356.1.

Parthiban et al., "Synthesis and Microbiological Evaluation of Some N-methyl Piperidone Oxime Ethers," Medicinal Chemistry Research, 14(8-9):523-538 (2005).

Smith et al. "Synthesis and Pharmacological Activity of Angiotensin Converting Enzyme Inhibitors: N-(mercaptoacyl)-4-substituted-(s)-prolines," Journal of Medicinal Chemistry, American Chemical Society, 31(4):875-885 (Jan. 1, 1988).

Cossy et al., "A Short Synthesis of Cisapride: A Gastrointestinal Stimulant Derived from cis-4-amino-3-methoxypiperidine," Tetrahedron Letters, 42(33):5713-5715 (Aug. 13, 2001).

Database Registry, Chemical Abstracts Service, "1-methyl-O-[bis(4-fluorophenyl)methyl] oxime-4-piperidinone," Database Accession No. 445392-83-6 (Aug. 29, 2002).

Teodori et al., "Design, Synthesis, and Preliminary Pharmacological Evaluation of 4-Aminopiperidine Derivatives as N-Type Calcium Channel Blockers Active on Pain and Neuropathic Pain," Journal of Medicinal Chemistry, American Chemical Society, 47:6070-6081 (Jan. 1, 2004).

Schroeder et al., "N-Type Calcium Channel Blockers: Novel Therapeutics for the Treatment of Pain," Medicinal Chemistry, Bentham Science Publishers, Ltd., 2(5):535-543 (Sep. 1, 2006).

European Supplementary Search Report and Search Opinion, mailed Aug. 16, 2011, for European Application No. 08767992.4.

* cited by examiner

SEQUENCE LISTING

<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
caccatggtc cgcttcgggg ac                                              22

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccgttcagtg gcctcctcc                                                  19

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctagcaccag tgatcctggt ctg                                             23

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agtgcgttgt gagcgcagta                                                 20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
caccatggtc cagaagagcg g                                          21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tctcagcgga tgtagacgcc t                                          21

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
caccatgtat gacgactcct ac                                         22

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggtggtcagt agctgtcctt agg                                        23

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caccatggct gctggctgcc t                                          21

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agagggtcac catagatagt gtctg                                      25

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 11
caccatgatt cgggccttcg ct                                               22

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agcctgcgga ctacaggttg ctgac                                            25
```

OXYIMINO COMPOUNDS AND THE USE THEREOF

PRIORITY INFORMATION

This application is the national stage of International Application No. PCT/US2008/006888, filed May 30, 2008, which claims the benefit of U.S. Provisional Application No. 60/924,808, filed May 31, 2007, which is incorporated herein by reference.

BACKGROUND OF THE INVENTION

1. Field of the Invention

This invention is in the field of medicinal chemistry. The invention relates to oxyimino compounds and the discovery that these compounds act as blockers of calcium ($Ca^{2+}$) channels.

2. Background Art

Calcium ions play fundamental roles in the regulation of many cellular processes. It is therefore essential that their intracellular levels be maintained under strict, yet dynamic control (Davila, H. M., *Annals of the New York Academy of Sciences*, pp. 102-117 (1999)). Voltage-gated calcium channels (VGCC) serve as one of the important mechanisms for fast calcium influx into the cell. Calcium channels are hetero-oligomeric proteins consisting of a pore-forming subunit (α1), which is able to form functional channels on its own in heterologous expression systems, and a set of auxiliary or regulatory subunits. Calcium channels have been classified based on their pharmacological and/or electrophysiological properties. The classification of voltage-gated calcium channels divides them into three groups: (i) high voltage-activated (HVA) channels, which include L-, N-, P-, and Q-types; (ii) intermediate (IVA) voltage-activated R-type channels; and (iii) low voltage-activated (LVA) T-type channels (Davila, supra). Voltage-gated calcium channels (VGCC) are also known as voltage-dependent calcium channels (VDCC) or voltage-sensitive calcium channels (VSCC).

Voltage-sensitive calcium channels (VSCC) regulate intracellular calcium concentration, which affects various important neuronal functions such as cellular excitability, neurotransmitter release, hormone secretion, intracellular metabolism, neurosecretory activity and gene expression (Hu et al., *Bioorganic & Medicinal Chemistry* 8:1203-1212 (2000)). N-type channels are found mainly in central and peripheral neurons, being primarily located on presynaptic nerve terminals. These channels regulate the calcium flux required for depolarization-evoked release of a transmitter from synaptic endings. The transmission of pain signals from the periphery to the central nervous system (CNS) is mediated by N-type calcium channels located in the spinal cord (Song et al., *J. Med. Chem.* 43:3474-3477 (2000)).

The six types of calcium channels (i.e., L, N, P, Q, R, and T) are expressed throughout the nervous system (Wallace, M. S., *The Clinical Journal of Pain* 16:580-585 (2000)). Voltage-sensitive calcium channels of the N-type exist in the superficial laminae of the dorsal horn and are thought to modulate nociceptive processing by a central mechanism. Blockade of the N-type calcium channel in the superficial dorsal horn modulates membrane excitability and inhibits neurotransmitter release, resulting in pain relief. Wallace (supra) suggests that based on animal models, N-type calcium channel antagonists have a greater analgesic potency than sodium channel antagonists.

N-type calcium channel blockers have usefulness for neuroprotection and analgesia. Ziconotide, which is a selective N-type calcium channel blocker, has been found to have analgesic activity in animal models and neuroprotective activity in focal and global ischemia models (Song et al., supra). Examples of known calcium channel blockers include flunarizine, fluspirilene, cilnipide, PD 157767, SB-201823, SB-206284, NNC09-0026, and PD 151307 (Hu et al., supra).

Blockade of N-type channels can prevent and/or attenuate subjective pain as well as primary and/or secondary hyperalgesia and allodynia in a variety of experimental and clinical conditions (Vanegas, H. et al., *Pain* 85:9-18 (2000)). N-type voltage-gated calcium channels (VGCC) play a major role in the release of synaptic mediators such as glutamate, acetylcholine, dopamine, norepinephrine, gamma-aminobutyric acid (GABA) and calcitonin gene-related peptide (CGRP).

Inhibition of voltage-gated L-type calcium channels has been shown to be beneficial for neuroprotection (Song et al., supra). However, inhibition of cardiac L-type calcium channels can lead to hypotension. It is believed that a rapid and profound lowering of arterial pressure tends to counteract the neuroprotective effects of L-type calcium channel blockers. A need exists for antagonists that are selective for N-type calcium channels over L-type calcium channels to avoid potential hypotensive effects.

Similar compounds to those of the present invention are described in EP1741702, WO2005097129 and WO1999026926, but the structures of these compounds are different from those of the present invention.

BRIEF SUMMARY OF THE INVENTION

The present invention is related to the use of oxyimino compounds represented by Formula I, I' or I" below, and the pharmaceutically acceptable salts, prodrugs and solvates thereof, as blockers of calcium ($Ca^{2+}$) channels. Certain compounds of Formula I, I' or I" show selectivity as N-type calcium channel blockers.

The invention is also related to treating, preventing or ameliorating a disorder responsive to the blockade of calcium channels in a mammal suffering from excess activity of said channels by administering an effective amount of a compound of Formula I, I' or I", or a pharmaceutically acceptable salt, prodrug or solvate thereof, as described herein. Specifically, the invention is related to treating, preventing or ameliorating a disorder responsive to the blockade of N-type calcium channels in a mammal suffering from excess activity of said channels by administering an effective amount of a compound of Formula I, I' or I", or a pharmaceutically acceptable salt, prodrug or solvate thereof, as described herein.

One aspect of the present invention is directed to novel compounds of Formula I, or a pharmaceutically acceptable salt, prodrug or solvate thereof. Another aspect of the present invention is directed to the use of the novel compounds of Formula I, compounds of Formula I' or compounds of Formula I", or a pharmaceutically acceptable salt, prodrug or solvate thereof, as blockers of N-type calcium channels.

A further aspect of the present invention is to provide a method for treating, preventing or ameliorating stroke, neuronal damage resulting from head trauma, epilepsy, pain (e.g., acute pain, chronic pain, which includes but is not limited to, neuropathic pain and inflammatory pain, or surgical pain), migraine, a mood disorder, schizophrenia, a neurodegenerative disorder (e.g., Alzheimer's disease, amyotrophic lateral sclerosis (ALS), or Parkinson's disease), depression, anxiety, a psychosis, hypertension, or cardiac arrhythmia, by administering an effective amount of a compound of Formula I, I' or I", or a pharmaceutically acceptable salt, prodrug or solvate thereof, to a mammal in need of such treatment, prevention or amelioration.

A further aspect of the present invention is to provide a pharmaceutical composition useful for treating, preventing or ameliorating a disorder responsive to the blockade of calcium ion channels, especially N-type calcium ion channels, said pharmaceutical composition containing an effective amount of a compound of Formula I, I' or I", or a pharmaceutically acceptable salt, prodrug or solvate thereof, in a mixture with one or more pharmaceutically acceptable carriers.

Also, an aspect of the invention is to provide a method of modulating calcium channels, especially N-type calcium channels, in a mammal, wherein said method comprises administering to the mammal an effective amount of at least one compound of Formula I, I' or I", or a pharmaceutically acceptable salt, prodrug or solvate thereof.

A further aspect of the present invention is to provide radiolabeled compounds of Formula I, I' or I" and the use of such compounds, or their pharmaceutically acceptable salts, prodrugs or solvates, as radioligands for their binding site on the calcium channel.

A further aspect of the invention is to provide a method for screening a candidate compound for the ability to bind to a receptor using a $^3H$, $^{11}C$ or $^{14}C$ radiolabeled compound of Formula I, I' or I", or a pharmaceutically acceptable salt, prodrug or solvate thereof. This method comprises a) introducing a fixed concentration of the radiolabeled compound to the receptor to form a mixture; b) titrating the mixture with a candidate compound; and c) determining the binding of the candidate compound to said receptor.

A further aspect of the invention is to provide the use of a compound of Formula I, I' or I", or a pharmaceutically acceptable salt, prodrug or solvate thereof, in the manufacture of a medicament for treating, preventing or ameliorating stroke, neuronal damage resulting from head trauma, epilepsy, pain, migraine, a mood disorder, schizophrenia, a neurodegenerative disorder, depression, anxiety, a psychosis, hypertension, or cardiac arrhythmia in a mammal. In a preferred embodiment, the invention provides the use of a compound of Formula I, I' or I", or a pharmaceutically acceptable salt, prodrug or solvate thereof, in the manufacture of a medicament for treating, preventing or ameliorating pain (e.g., acute pain, chronic pain, which includes but is not limited to, neuropathic pain and inflammatory pain or surgical pain).

Additional embodiments and advantages of the invention will be set forth in part in the description that follows, and will flow from the description, or may be learned by practice of the invention. The embodiments and advantages of the invention will be realized and attained by means of the elements and combinations particularly pointed out in the appended claims.

It is to be understood that both the foregoing summary and the following detailed description are exemplary and explanatory only and are not restrictive of the invention, as claimed.

DETAILED DESCRIPTION OF THE INVENTION

One aspect of the present invention is based upon the use of compounds of Formula I, I' or I", and the pharmaceutically acceptable salts, prodrugs and solvates thereof, as blockers of $Ca^{2+}$ channels. In view of this property, compounds of Formula I, and the pharmaceutically acceptable salts, prodrugs and solvates thereof, are useful for treating disorders responsive to the blockade of calcium ion channels. In one aspect, compounds of Formula I, I' or I", and the pharmaceutically acceptable salts, prodrugs and solvates thereof, selectively block N-type calcium ion channels and, thus, are useful for treating disorders responsive to the selective blockade of N-type calcium ion channels.

The present invention provides

1) A compound having the Formula I:

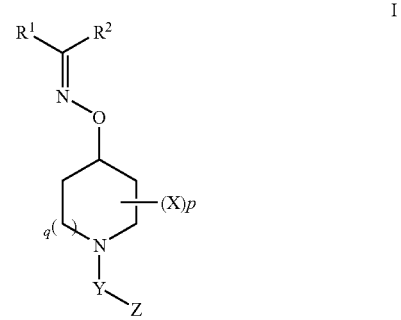

or a pharmaceutically acceptable salt, a prodrug or a solvate thereof, wherein:

Y is CO or $SO_m$;

Z is hydrogen, optionally substituted lower alkyl, optionally substituted lower alkenyl, optionally substituted lower alkynyl, optionally substituted cycloalkyl, optionally substituted bicycloalkyl, optionally substituted cycloalkenyl, optionally substituted aryl, optionally substituted heterocyclyl, $NR^5R^6$, $OR^5$, $SR^5$, $COR^5$ or $CONR^5R^6$;

$R^1$ and $R^2$ are each independently hydrogen, optionally substituted lower alkyl, optionally substituted lower alkenyl, optionally substituted lower alkynyl, optionally substituted cycloalkyl, optionally substituted cycloalkenyl, optionally substituted aryl, optionally substituted heterocyclyl, cyano, $COR^5$, or $CONR^5R^6$, or $R^1$ and $R^2$ taken together, with the carbon atom to which they are attached, form optionally substituted cycloalkyl, optionally substituted bicycloalkyl, optionally substituted cycloalkenyl or optionally substituted heterocyclyl;

$R^5$ and $R^6$ are each independently hydrogen, optionally substituted lower alkyl, optionally substituted lower alkenyl, optionally substituted lower alkynyl, optionally substituted cycloalkyl, optionally substituted bicycloalkyl, optionally substituted cycloalkenyl, optionally substituted aryl or optionally substituted heterocyclyl;

each X is independently =O, optionally substituted lower alkyl, optionally substituted lower alkenyl, optionally substituted lower alkynyl, halogen, cyano, nitro, $NR^5R^6$, $OR^5$, $SR^5$, $COR^5$, $COOR^5$, $CONR^5R^6$, $NR^5COR^5$, $OCOR^5$, $SOR^5$, $SO_2R^5$, $SO_3R^5$, $SONR^5R^6$, $SO_2NR^5R^6$, $NR^5SOR^5$, or $NR^5SO_2R^5$;

m is 1 or 2;

p is 0, 1 or 2; and q is 0 or 1;

and provided that when $R^1$ is optionally substituted phenyl, $R^2$ is optionally substituted heterocyclyl or thiazolylcarbamoyl, and Y is CO, then Z is not methyl, tert-butoxy or 2-(N,N'-dimethylamino)ethoxy.

when $R^1$ is aminothiazolyl, $R^2$ is $CONHR^6$, $R^6$ is optionally substituted heterocyclyl and Y is CO, Z is not 4-nitrobenzyloxy.

2) The compound of the above 1), wherein Y is $SO_2$.

3) The compound of the above 1) or 2), wherein Z is optionally substituted aryl or optionally substituted heterocyclyl.

4) A pharmaceutical composition, comprising the compound of any of the above 1) to 3) and a pharmaceutically acceptable carrier.

5) A method of treating, preventing or ameliorating a disorder responsive to the blockade of calcium channels in a mammal suffering from said disorder, comprising administering to a mammal in need of such treatment, prevention or amelioration an effective amount of a compound of any of the above 1) to 3).

6) The method of the above 5), wherein a disorder responsive to the blockade of N-type calcium channels is treated, prevented or ameliorated.

7) A method for treating, preventing or ameliorating stroke, neuronal damage resulting from head trauma, epilepsy, pain, migraine, a mood disorder, schizophrenia, a neurodegenerative disorder, depression, anxiety, a psychosis, hypertension or cardiac arrhythmia in a mammal, comprising administering an effective amount of a compound of any of the above 1) to 3).

8) The method of the above 7), wherein the method is for treating, preventing or ameliorating pain selected from the group consisting of chronic pain, acute pain, and surgical pain.

9) A method of modulating calcium channels in a mammal, comprising administering to the mammal at least one compound of any one of the above 1) to 3).

10) The method of the above 9), wherein the N-type calcium channel is modulated.

11) A compound having the Formula I as described in the above 1) to 3), wherein the compound is $^3H$, $^{11}C$, or $^{14}C$ radiolabeled.

12) A method of screening a candidate compound for the ability to bind to a receptor using a radiolabeled compound of the above 11), comprising a) introducing a fixed concentration of the radiolabeled compound to the receptor to form a mixture; b) titrating the mixture with a candidate compound; and c) determining the binding of the candidate compound to said receptor.

13) Use of a compound of Formula I as described in any one of the above 1) to 3) in the manufacture of a medicament for the treating, preventing or ameliorating stroke, neuronal damage resulting from head trauma, epilepsy, pain, migraine, a mood disorder, schizophrenia, a neurodegenerative disorder, depression, anxiety, a psychosis, hypertension or cardiac arrhythmia in a mammal.

14) Use of a compound of Formula I as described in any one of the above 1) to 3) in the manufacture of a medicament for the treating, preventing or ameliorating pain selected from chronic pain, acute pain, and surgical pain.

15) A pharmaceutical composition for modulating calcium channels in a mammal, comprising the compound having the Formula I':

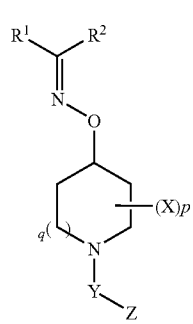

or a pharmaceutically acceptable salt, a prodrug or a solvate thereof, wherein:

Y is CO or $SO_m$;

Z is hydrogen, optionally substituted lower alkyl, optionally substituted lower alkenyl, optionally substituted lower alkynyl, optionally substituted cycloalkyl, optionally substituted bicycloalkyl, optionally substituted cycloalkenyl, optionally substituted aryl, optionally substituted heterocyclyl, $NR^5R^6$, $OR^5$, $SR^5$, $COR^5$ or $CONR^5R^6$;

$R^1$ and $R^2$ are each independently hydrogen, optionally substituted lower alkyl, optionally substituted lower alkenyl, optionally substituted lower alkynyl, optionally substituted cycloalkyl, optionally substituted cycloalkenyl, optionally substituted aryl, optionally substituted heterocyclyl, cyano, $COR^5$, or $CONR^5R^6$, or $R^1$ and $R^2$ taken together, with the carbon atom to which they are attached, form optionally substituted cycloalkyl, optionally substituted bicycloalkyl, optionally substituted cycloalkenyl or optionally substituted heterocyclyl;

$R^5$ and $R^6$ are each independently hydrogen, optionally substituted lower alkyl, optionally substituted lower alkenyl, optionally substituted lower alkynyl, optionally substituted cycloalkyl, optionally substituted bicycloalkyl, optionally substituted cycloalkenyl, optionally substituted aryl or optionally substituted heterocyclyl;

each X is independently =O, optionally substituted lower alkyl, optionally substituted lower alkenyl, optionally substituted lower alkynyl, halogen, cyano, nitro, $NR^5R^6$, $OR^5$, $SR^5$, $COR^5$, $COOR^S$, $CONR^5R^6$, $NR^5COR^5$, $OCOR^5$, $SOR^5$, $SO_2R^5$, $SO_3R^5$, $SONR^5R^6$, $SO_2NR^5R^6$, $NR^5SOR^5$, or $NR^5SO_2R^5$;

m is 1 or 2;

p is 0, 1 or 2; and q is 0 or 1;

and a pharmaceutically acceptable carrier.

16) A method of treating, preventing or ameliorating a disorder responsive to the blockade of calcium channels in a mammal suffering from said disorder, comprising administering to a mammal in need of such treatment, prevention or amelioration an effective amount of a compound of the above 15).

17) The method of the above 16), wherein a disorder responsive to the blockade of N-type calcium channels is treated, prevented or ameliorated.

18) A method for method for treating, preventing or ameliorating stroke, neuronal damage resulting from head trauma, epilepsy, pain, migraine, a mood disorder, schizophrenia, a neurodegenerative disorder, depression, anxiety, a psychosis, hypertension or cardiac arrhythmia in a mammal, comprising administering an effective amount of a compound of the above 15).

19) The method of the above 18), wherein the method is for treating, preventing or ameliorating pain selected from the group consisting of chronic pain, acute pain, and surgical pain.

20) A method of modulating calcium channels in a mammal, comprising administering to the mammal at least one compound the above 15).

21) The method of the above 20), wherein the N-type calcium channel is modulated.

22) A method of screening a candidate compound for the ability to bind to a receptor using a radiolabeled compound of the above 15), comprising a) introducing a fixed concentration of the radiolabeled compound to the receptor to form a mixture; b) titrating the mixture with a candidate compound; and c) determining the binding of the candidate compound to said receptor.

23) Use of a compound of the above 15) in the manufacture of a medicament for the treating, preventing or ameliorating stroke, neuronal damage resulting from head trauma, epilepsy, pain, migraine, a mood disorder, schizophrenia, a neurodegenerative disorder, depression, anxiety, a psychosis, hypertension or cardiac arrhythmia in a mammal.

24) Use of a compound of the above 15) in the manufacture of a medicament for the treating, preventing or ameliorating pain selected from the group consisting of chronic pain, acute pain, and surgical pain.

25) A kit comprising a container containing an effective amount of the compound or a pharmaceutically acceptable derivative of the compound of the above 1).

In the present specification, the term "halogen" includes fluorine, chlorine, bromine and iodine. Fluorine or chlorine is preferable. The halogen parts of "halo(lower)alkyl", "halo(lower)alkoxy" and "haloacyl" are the same as the above "halogen"

The term "lower alkyl" includes straight or branched chain alkyl having 1 to 10 carbon atoms, preferably 1 to 6 carbon atoms and most preferably 1 to 3 carbon atoms. For example, included are methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl, n-decyl and the like.

The optional substituents in "optionally substituted lower alkyl", include
1) halogen,
2) hydroxy,
3) carboxy,
4) mercapto,
5) cyano,
5) lower alkoxy optionally substituted with at least one substituent selected from the group consisting of Group A and Group C,
6) acyl optionally substituted with at least one substituent selected from the group consisting of Group A, Group B and Group C,
7) acyloxy optionally substituted with at least one substituent selected from the group consisting of Group A, Group B and Group C
8) lower alkoxycarbonyl optionally substituted with at least one substituent selected from the group consisting of Group A and Group C,
9) aryloxycarbonyl optionally substituted with at least one substituent selected from the group consisting of Group A, Group B and Group C,
10) lower alkylthio optionally substituted with at least one substituent selected from the group consisting of Group A and Group C,
11) lower alkylsulfonyl optionally substituted with at least one substituent selected from the Group A and Group C,
12) amino optionally substituted with at least one substituent selected from the group consisting of Group A, Group B and Group C
13) imino optionally substituted with at least one substituent selected from the group consisting of Group A, Group B and Group C,
14) carbamoyl optionally substituted with at least one substituent selected from the group consisting of Group B and Group C,
15) carbamoyloxy optionally substituted with at least one substituent selected from the group consisting of Group B and Group C,
16) thiocarbamoyl optionally substituted with at least one substituent selected from the group consisting of Group B and Group C,
17) cycloalkyl optionally substituted with at least one substituent selected from the group consisting of Group A, Group B and Group C,
18) cycloalkenyl optionally substituted with at least one substituent selected from the group consisting of Group A, Group B and Group C,
19) aryl optionally substituted with at least one substituent selected from the group consisting of Group A, Group B and Group C,
20) heterocyclyl optionally substituted with at least one substituent selected from the group consisting of Group A, Group B, Group C and oxo,
21) aryloxy optionally substituted with at least one substituent selected from the group consisting of Group A, Group B and Group C,
22) arylthio optionally substituted with at least one substituent selected from the group consisting of Group A, Group B and Group C,
23) cycloalkylsulfonyl optionally substituted with at least one substituent selected from the group consisting of Group A, Group B and Group C,
24) arylsulfonyl optionally substituted with at least one substituent selected from the group consisting of Group A, Group B and Group C,
25) heterocyclylsulfonyl optionally substituted with at least one substituent selected from the group consisting of Group A, Group B, Group C, and oxo and the like.

Group A includes hydroxy, halogen, lower alkoxy, halo(lower)alkoxy, hydroxy(lower)alkoxy, aryl(lower)alkoxy, acyl, haloacyl, aminoacyl, acyloxy, carboxy, lower alkoxycarbonyl, carbamoyl, lower alkylcarbamoyl, and optionally substituted amino, wherein the substituents are selected from the group consisting of halogen, hydroxy, lower alkyl, hydroxy(lower)alkyl, lower alkoxy(lower)alkyl, acyl, cycloalkyl, aryl and heterocyclyl.

Group B includes lower alkyl, halo(lower)alkyl, hydroxy(lower)alkyl, lower alkoxy(lower)alkyl, amino(lower)alkyl, lower alkylamino(lower)alkyl, aryl(lower)alkyl and heterocyclyl(lower)alkyl.

Group C includes optionally substituted cycloalkyl, optionally substituted cycloalkenyl, optionally substituted aryl and optionally substituted heterocyclyl, wherein the substituents are selected from the group consisting of Group A, Group B and oxo.

The term "optionally substituted lower alkyl" refers to a lower alkyl that can be substituted with one or more of the above-mentioned substituents at any possible positions.

The lower alkyl parts of "lower alkoxy", "lower alkoxycarbonyl", "lower alkylsulfonyl", "lower alkylthio", "halo(lower)alkyl", "hydroxy(lower)alkyl", "amino(lower)alkyl", "lower alkylamino", "lower alkylamino(lower)alkyl", "aryl (lower)alkyl", "halo(lower)alkoxy", "hydroxy(lower) alkoxy", "lower alkoxy(lower)alkyl", "aryl(lower)alkoxy", "lower alkylcarbamoyl", "heterocyclyl(lower)alkyl", and "lower alkylenedioxy" are as defined for "lower alkyl".

The optional substituents in "optionally substituted lower alkoxy" include those defined for "optionally substituted lower alkyl".

The term "lower alkenyl" refers to straight or branched chain alkenyl of 2 to 10 carbon atoms, preferably 2 to 8 carbon atoms, more preferably 3 to 6 carbon atoms having at least one double bond at any possible positions. For example, useful lower alkenyl groups include vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl and the like.

The optional substituents in "optionally substituted lower alkenyl" and "optionally substituted lower alkynyl" include those defined for "optionally substituted lower alkyl".

The term "lower alkynyl" refers to straight or branched chain alkenyl of 2 to 10 carbon atoms, preferably 2 to 8 carbon atoms, more preferably 3 to 6 carbon atoms having at least one triple bond at any possible positions. Furthermore, "lower alkynyl" can have at least one double bond at any possible positions. Suitable lower alkynyl groups are, for example, ethynyl, propynyl, butynyl, pentynyl, hexynyl, heptynyl, octynyl, nonynyl, decynyl and the like.

Substituents for "optionally substituted lower alkynyl" are those defined for "optionally substituted lower alkyl".

The term "acyl" refers to straight or branched chain aliphatic acyl having 1 to 10 carbon atoms, preferably 1 to 6 carbon atoms, more preferably 1 to 4 carbon atoms, cyclic aliphatic acyl having 4 to 9 carbon atoms, preferably 4 to 7 carbon atoms, aroyl and heterocyclylcarbonyl. Suitable acyl groups include, for example, formyl, acetyl, propionyl, butyryl, isobutyryl, valeryl, pivaloyl, hexanoyl, acryloyl, propioloyl, methacryloyl, crotonoyl, cyclopropylcarbonyl, cyclohexylcarbonyl, cyclooctylcarbonyl, benzoyl, pyridinecarbonyl, pyrimidinecarbonyl, piperidincarbonyl, piperazinocarbonyl, morphorinocarbonyl and the like.

The acyl part in "acyloxy" "haloacyl" and "aminoacyl" is that defined for "acyl".

The term "cycloalkyl" refers to a carbocycle having 3 to 8 carbon atoms, and includes cyclopropyl, cyclobutyl, cyclopentyl, cyclohexyl, cycloheptyl, cyclooctyl and the like.

Examples of substituents for "optionally substituted cycloalkyl" are
1) lower alkyl optionally substituted with at least one substituent selected from the group consisting of Group A and Group C, and
2) the same as those defined for "optionally substituted lower alkyl".

The term "optionally substituted cycloalkyl" refers to a cycloalkyl defined above that can be substituted with one or more of these substituents.

The cycloalkyl part of "cycloalkylsulfonyl" is as defined for "cycloalkyl".

The term "bicycloalkyl" refers to a bicyclic hydrocarbon ring system having from 6 to 14 carbon atoms and at least one saturated cyclic alkyl ring. Examples of bicycloalkyl groups are indanyl, norbornyl, 1,2,3,4-tetrahydronaphthyl, 5,6,7,8-tetrahydronaphthyl, perhydronaphthyl, and the like.

Examples of substituents for "optionally substituted bicycloalkyl" are the same as those for the above "optionally substituted cycloalkyl."

The term "cycloalkenyl" refers to a group having at least one double bond at any possible positions in the above "cycloalkyl". Examples are cyclopropenyl, cyclobutenyl, cyclopentenyl, cyclohexenyl and cyclohexadienyl. Substituents for "optionally substituted cycloalkenyl" are those defined for "optionally substituted cycloalkyl."

As substituents for "optionally substituted amino", exemplified are
1) lower alkyl optionally substituted with at least one substituent selected from the group consisting of Group A and Group C, and
2) the same as those defined for "optionally substituted lower alkyl". The term "lower alkylamino" includes mono-alkylamino and di-alkylamino. The term "aryl" includes phenyl, naphthyl, anthryl, phenanthryl, indenyl and the like. Phenyl is preferable.

The aryl parts of "aryloxy", "aryloxycarbonyl", "arylthio", "arylsulfonyl", "aryl(lower)alkyl", and "aryl(lower)alkoxy" are the same as the above "aryl".

The terms "heterocyclyl" or "heterocycle" refer to a heterocyclic group containing at least one heteroatom arbitrarily selected from the group consisting of O, S and N. Suitable heterocyclyl groups are, for example, 5- or 6-membered heteroaryl groups, such as pyrrolyl, imidazolyl, pyrazolyl, pyridyl, pyridazinyl, pyrimidinyl, pyrazinyl, isoxazolyl, oxazolyl, oxadiazolyl, isothiazolyl, thiazolyl, thiadiazolyl, furyl and thienyl; fused heterocyclyl groups having two rings, such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazoropyridyl, imidazothiazolyl, pyrazinopyridazinyl, quinazolinyl, quinolyl, isoquinolyl, naphthyridinyl, dihydropyridyl, tetrahydroquinolyl and tetrahydrobenzothienyl; fused heterocyclyl groups having three rings such as carbazolyl, acridinyl, xanthenyl, phenothiazinyl, phenoxathiinyl, phenoxazinyl and dibenzofuryl; and non-aromatic heterocyclyl such as dioxanyl, thiiranyl, oxiranyl, oxathiolanyl, azetidinyl, thianyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydrofuryl, tetrahydropyranyl, tetrahydrothiazolyl and tetrahydroisothiazolyl.

The heterocyclyl parts of "heterocyclyl(lower)alkyl" and "heterocyclylsulfonyl" are the same as the above "heterocyclyl".

Examples of the substituents for "optionally substituted aryl" and "optionally substituted heterocyclyl" are
1) the same as those for the above "optionally substituted lower alkyl",
2) lower alkyl optionally substituted with at least one substituent selected from the Group A and Group C,
3) oxo and
4) lower alkylenedioxy.

These substituents may attach to one or more of any possible positions.

The phrase "$R^1$ and $R^2$ taken together, with the carbon atom to which they are attached, form optionally substituted cycloalkane, optionally substituted cycloalkene, optionally substituted bicycloalkane, or optionally substituted heterocycle" means

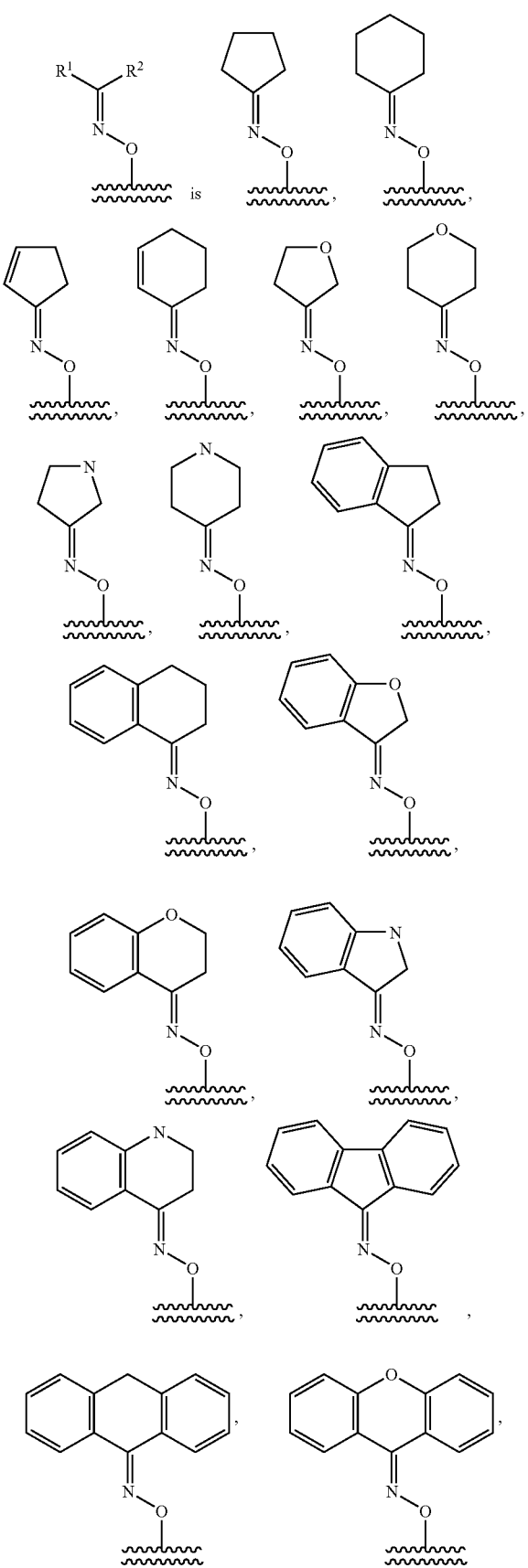

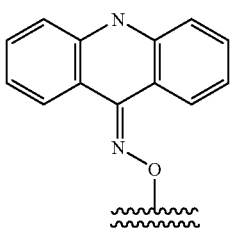

or the like. These cycloalkane, cycloalkene, bicycloalkane, and heterocycle may be substituted with the substituents described in the above "optionally substituted cycloalkyl", "optionally substituted cycloalkenyl", "optionally substituted bicycloalkyl", "optionally substituted heterocyclyl", respectively.

When p is 2, each X can be the same or different

In one embodiment, preferable Oxyimino Compounds are the compounds of the following Formula I":

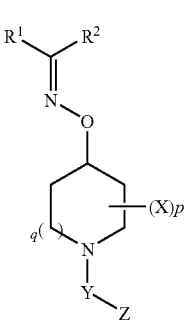

wherein =$CR^1R^2$ is selected from the group consisting of:

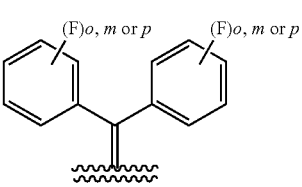

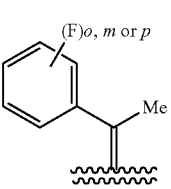

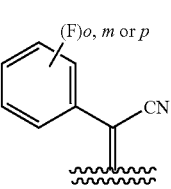

-continued (Cd) ![structure with (Cl)o, m or p on phenyl, Me substituent]

(Ce) ![structure with (Cl)o, m or p on phenyl, CN substituent]

(Cf) ![structure with (CN)o, m or p on phenyl, Me substituent]

(Cg) ![structure with (CN)o, m or p on phenyl, CN substituent]

(Ch) ![4-pyridyl with Me]

(Ci) ![4-pyridyl with CN]

(Cj) ![3-pyridyl with Me]

(Ck) ![3-pyridyl with CN]

(Cl) ![2-pyridyl with Me]

(Cm) ![2-pyridyl with CN]

(Cn) ![bis(2-pyridyl)]

(Co) ![4-Cl-2-pyridyl with Me]

(Cp) ![6-Cl-2-pyridyl with Me]

(Cq) ![2-Cl-4-pyridyl with Me]

(Cr) ![5-Cl-3-pyridyl with Me]

(Cs) ![4-CN-2-pyridyl with Me]

(Ct) ![6-CN-2-pyridyl with Me]

(Cu) ![2-CN-4-pyridyl with Me]

(Cv) ![5-CN-3-pyridyl with Me]

-continued
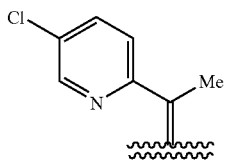 (Cw)
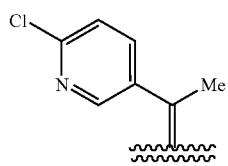 (Cx)
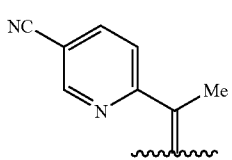 (Cy)
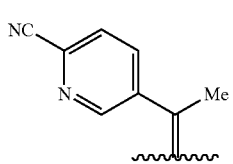 (Cz)
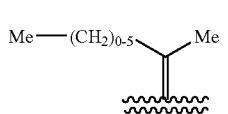 (Caa)
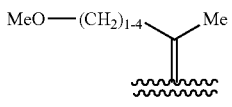 (Cab)
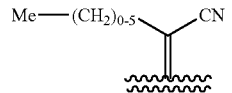 (Cac)
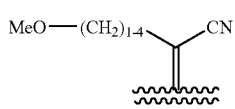 (Cad)
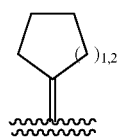 (Cae)
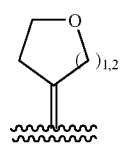 (Caf)
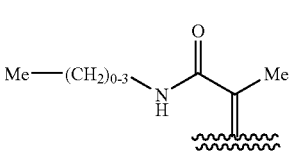 (Cag)
-continued
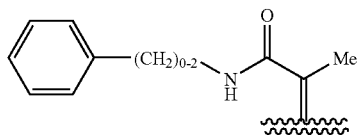 (Cah)
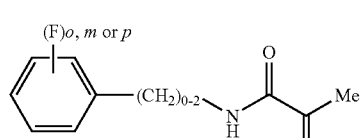 (Cai)
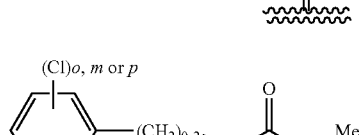 (Caj)
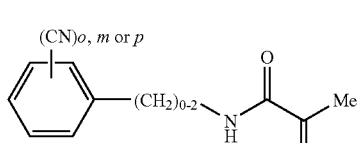 (Cak)
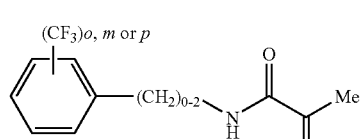 (Cal)
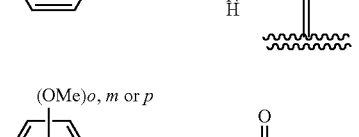 (Cam)
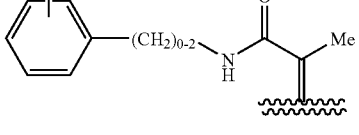 (Can)
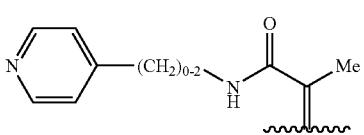 (Cao) and
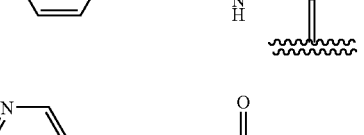 (Cap)
In another embodiment, useful compounds of the Formula I" include those wherein

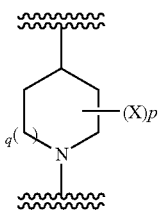
(hereinafter referred to as Xpq) is one of the followings:
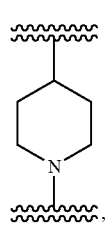
(Ra)
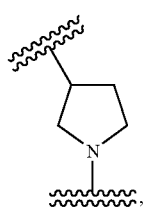
(Rb)
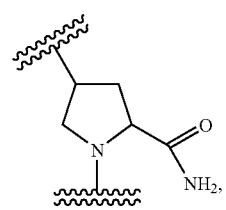
(Rc)
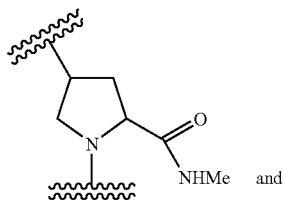
(Rd)
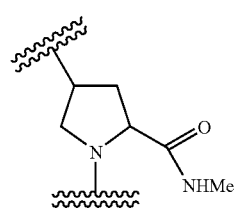
and
(Re)
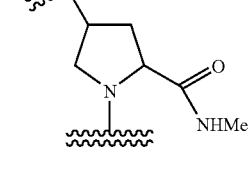
In another embodiment, useful compounds of the Formula I" include those wherein Y—Z is one of the followings:
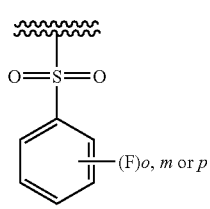
(YZa)
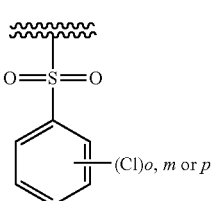
(YZb)
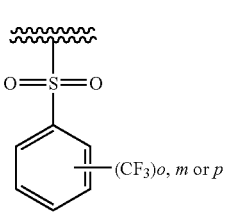
(YZc)
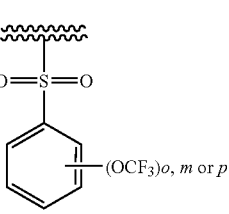
(YZd)
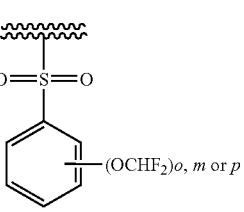
(YZe)
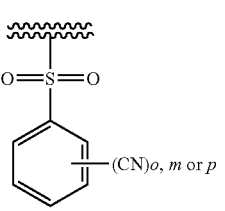
(YZf)
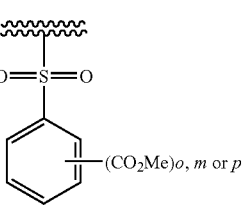
(YZg)
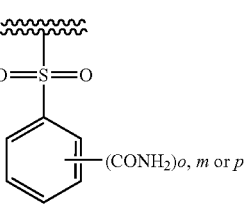
(YZh)

-continued
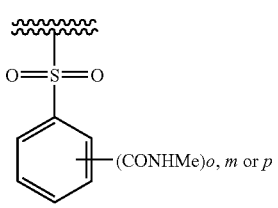
(YZi)
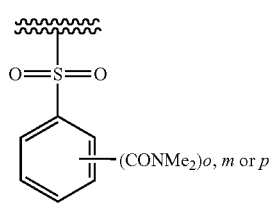
(YZj)
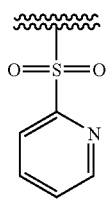
(YZk)
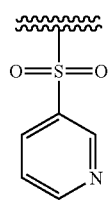
(YZl)
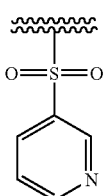
(YZm)
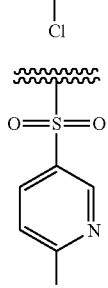
(YZn)
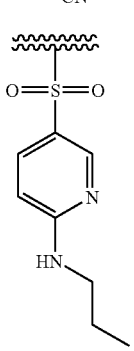
(YZo)
-continued
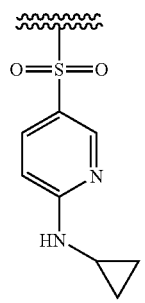
(YZp)
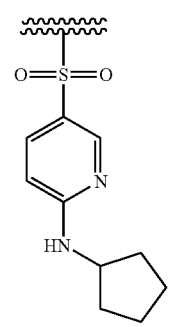
(YZq)
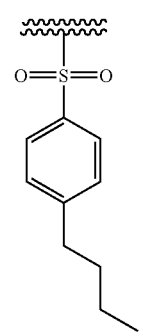
(YZr)
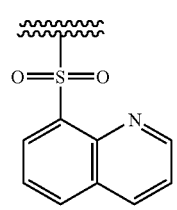
(YZs)
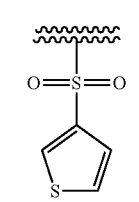
(YZt)
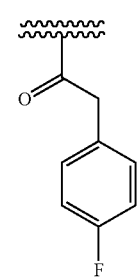
(YZu)

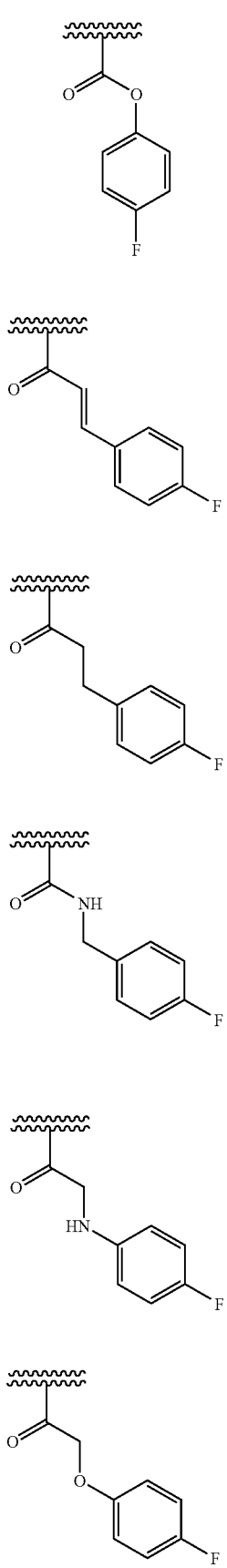
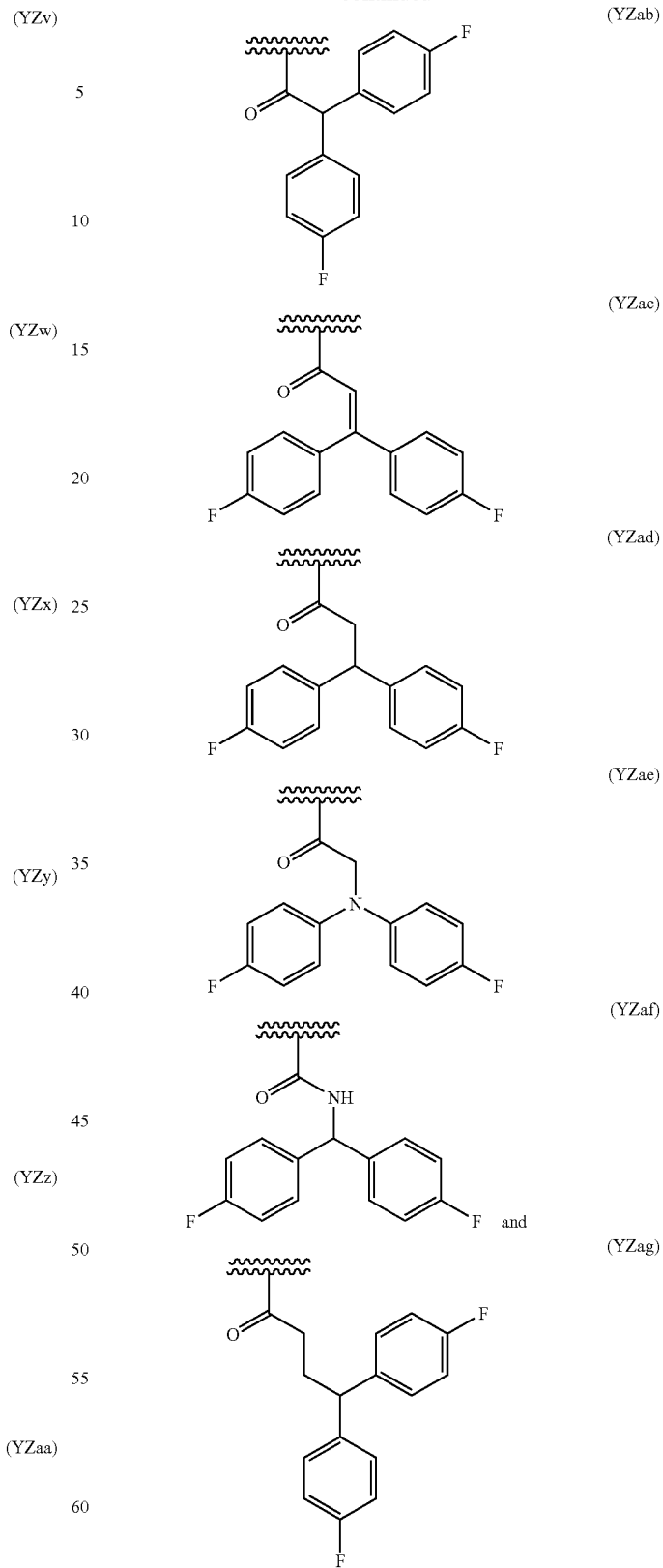
In another embodiment, useful compounds of the Formula I' include those wherein the combination of =$CR^1R^2$, Xpq, and Y—Z(=$CR^1R^2$, Xpq, Y—Z) is one of the followings:

(Ca,Ra,YZa),(Ca,Ra,YZb),(Ca,Ra,YZc),(Ca,Ra,YZd), (Ca,Ra,YZe),(Ca,Ra,YZ f),(Ca,Ra,YZg),(Ca,Ra,YZh),(Ca, Ra,YZi),(Ca,Ra,YZj),(Ca,Ra,YZk),(Ca,Ra,YZl),(Ca,Ra,YZ m) (Ca,Ra,YZn),(Ca,Ra,YZo),(Ca,Ra,YZp),(Ca,Ra,YZq), (Ca,Ra,YZr),(Ca,Ra,YZs),(Ca,Ra, YZt),(Ca,Ra,YZu),(Ca, Ra,YZv),(Ca,Ra,YZw),(Ca,Ra,YZx),(Ca,Ra,YZy),(Ca,Ra, YZz),(Ca,R a,YZaa),(Ca,Ra,YZab),(Ca,Ra,YZac),(Ca,Ra, YZad),(Ca,Ra,YZae),(Ca,Ra,YZaf),(Ca,Ra,YZ ag),(Ca,Rb, YZa),(Ca,Rb,YZb),(Ca,Rb,YZc),(Ca,Rb,YZd),(Ca,Rb, YZe),(Ca,Rb,YZf),(Ca,Rb, YZg),(Ca,Rb,YZh),(Ca,Rb, YZi),(Ca,Rb,YZj),(Ca,Rb,YZk),(Ca,Rb,YZl),(Ca,Rb, YZm),(Ca,R b,YZn),(Ca,Rb,YZo), (Ca,Rb,YZp), (Ca,Rb, YZq),(Ca,Rb,YZr),(Ca,Rb,YZs),(Ca,Rb,YZt), (Ca, Rb,YZu),(Ca,Rb,YZy),(Ca,Rb,YZw),(Ca,Rb,YZx),(Ca,Rb, YZy),(Ca,Rb,YZz),(Ca,Rb,YZaa), (Ca,Rb,YZab),(Ca,Rb, YZac),(Ca,Rb,YZad),(Ca,Rb,YZae),(Ca,Rb,YZaf),(Ca,Rb, YZag),(Ca, Rc,YZa),(Ca,Rc,YZb),(Ca,Rc,YZc),(Ca,Rc, YZd),(Ca,Rc,YZe),(Ca,Rc,YZf),(Ca,Rc,YZg),(C a,Rc, YZh),(Ca,Rc,YZi),(Ca,Rc,YZj),(Ca,Rc,YZk),(Ca,Rc,YZl), (Ca,Rc,YZm),(Ca,Rc,YZn), (Ca,Rc,YZo),(Ca,Rc,YZp),(Ca, Rc,YZq),(Ca,Rc,YZr),(Ca,Rc,YZs),(Ca,Rc,YZt),(Ca,Rc, YZu), (Ca,Rc,YZy),(Ca,Rc,YZw),(Ca,Rc,YZx),(Ca,Rc, YZy),(Ca,Rc,YZz),(Ca,Rc,YZaa),(Ca,Rc,Y Zab),(Ca,Rc, YZac),(Ca,Rc,YZad),(Ca,Rc,YZae),(Ca,Rc,YZaf),(Ca,Rc, YZag),(Ca,Rd,YZa), (Ca,Rd,YZb),(Ca,Rd,YZc),(Ca,Rd, YZd),(Ca,Rd,YZe),(Ca,Rd,YZf),(Ca,Rd,YZg),(Ca,Rd, YZh), (Ca,Rd,YZi),(Ca,Rd,YZj),(Ca,Rd,YZk),(Ca,Rd, YZl),(Ca,Rd,YZm),(Ca,Rd,YZn),(Ca,Rd,Y Zo),(Ca,Rd, YZp),(Ca,Rd,YZq),(Ca,Rd,YZr),(Ca,Rd,YZs),(Ca,Rd, YZt),(Ca,Rd,YZu),(Ca,Rd, YZy),(Ca,Rd,YZw),(Ca,Rd, YZx),(Ca,Rd,YZy),(Ca,Rd,YZz),(Ca,Rd,YZaa),(Ca,Rd, YZab),(C a,Rd,YZac),(Ca,Rd,YZad),(Ca,Rd,YZae),(Ca,Rd, YZaf),(Ca,Rd,YZag),(Ca,Re,YZa),(Ca,Re, YZb),(Ca,Re, YZc),(Ca,Re,YZd),(Ca,Re,YZe),(Ca,Re,YZf),(Ca,Re, YZg),(Ca,Re,YZh),(Ca,R e,YZi),(Ca,Re,YZj),(Ca,Re,YZk), (Ca,Re,YZl),(Ca,Re,YZm),(Ca,Re,YZn),(Ca,Re,YZo),(Ca, Re,YZp),(Ca,Re,YZq),(Ca,Re,YZr),(Ca,Re,YZs),(Ca,Re, YZt),(Ca,Re,YZu),(Ca,Re,YZy),(Ca, Re,YZw),(Ca,Re, YZx),(Ca,Re,YZy),(Ca,Re,YZz),(Ca,Re,YZaa),(Ca,Re, YZab),(Ca,Re,YZa c) (Ca,Re,YZad),(Ca,Re,YZae),(Ca,Re, YZaf),(Ca,Re,YZag),(Cb,Ra,YZa),(Cb,Ra,YZb),(Cb, Ra,YZc),(Cb,Ra,YZd),(Cb,Ra,YZe),(Cb,Ra,YZf),(Cb,Ra, YZg),(Cb,Ra,YZh),(Cb,Ra,YZi),(C b,Ra,YZj),(Cb,Ra, YZk),(Cb,Ra,YZl),(Cb,Ra,YZm),(Cb,Ra,YZn),(Cb,Ra, YZo),(Cb,Ra,YZp), (Cb,Ra,YZq),(Cb,Ra,YZr),(Cb,Ra, YZs),(Cb,Ra,YZt),(Cb,Ra,YZu),(Cb,Ra,YZy),(Cb,Ra,YZ w) (Cb,Ra,YZx),(Cb,Ra,YZy),(Cb,Ra,YZz),(Cb,Ra,YZaa), (Cb,Ra,YZab),(Cb,Ra,YZac),(Cb, Ra,YZad),(Cb,Ra,YZae), (Cb,Ra,YZaf),(Cb,Ra,YZag),(Cb,Rb,YZa),(Cb,Rb,YZb), (Cb,Rb,YZ c) (Cb,Rb,YZd),(Cb,Rb,YZe),(Cb,Rb,YZf),(Cb, Rb,YZg),(Cb,Rb,YZh),(Cb,Rb,YZi),(Cb,Rb, YZj),(Cb,Rb, YZk),(Cb,Rb,YZl),(Cb,Rb,YZm),(Cb,Rb,YZn),(Cb,Rb, YZo),(Cb,Rb,YZp),(Cb, Rb,YZq),(Cb,Rb,YZr),(Cb,Rb, YZs),(Cb,Rb,YZt),(Cb,Rb,YZu),(Cb,Rb,YZy),(Cb,Rb, YZw), (Cb,Rb,YZx),(Cb,Rb,YZy),(Cb,Rb,YZz),(Cb,Rb, YZaa),(Cb,Rb,YZab),(Cb,Rb,YZac),(Cb,Rb, YZad),(Cb, Rb,YZae),(Cb,Rb,YZaf),(Cb,Rb,YZag),(Cb,Rc,YZa),(Cb, Rc,YZb),(Cb,Rc,YZc), (Cb,Rc,YZd),(Cb,Rc,YZe),(Cb,Rc, YZf),(Cb,Rc,YZg),(Cb,Rc,YZh),(Cb,Rc,YZi),(Cb,Rc,YZj), (Cb,Rc,YZk),(Cb,Rc,YZl),(Cb,Rc,YZm),(Cb,Rc,YZn),(Cb, Rc,YZo),(Cb,Rc,YZp),(Cb,Rc,Y Zq),(Cb,Rc,YZr),(Cb,Rc, YZs),(Cb,Rc,YZt),(Cb,Rc,YZu),(Cb,Re,YZy),(Cb,Rc, YZw),(Cb,Rc, YZx),(Cb,Rc,YZy),(Cb,Rc,YZz),(Cb,Rc, YZaa),(Cb,Rc,YZab),(Cb,Rc,YZac),(Cb,Rc,YZad),(Cb,Rc, YZae),(Cb,Rc,YZaf),(Cb,Rc,YZag),(Cb,Rd,YZa),(Cb,Rd, YZb),(Cb,Rd,YZc),(Cb,Rd, YZd),(Cb,Rd,YZe),(Cb,Rd, YZf),(Cb,Rd,YZg),(Cb,Rd,YZh),(Cb,Rd,YZi),(Cb,Rd, YZj),(Cb, Rd,YZk),(Cb,Rd,YZl),(Cb,Rd,YZm),(Cb,Rd, YZn),(Cb,Rd,YZo),(Cb,Rd,YZp),(Cb,Rd,YZq), (Cb,Rd, YZr),(Cb,Rd,YZs),(Cb,Rd,YZt),(Cb,Rd,YZu),(Cb,Rd, YZy),(Cb,Rd,YZw),(Cb,Rd,Y Zx),(Cb,Rd,YZy),(Cb,Rd, YZz),(Cb,Rd,YZaa),(Cb,Rd,YZab),(Cb,Rd,YZac),(Cb,Rd, YZad), (Cb,Rd,YZae),(Cb,Rd,YZaf),(Cb,Rd,YZag),(Cb,Re, YZa),(Cb,Re,YZb),(Cb,Re,YZc),(Cb,Re, YZd),(Cb,Re, YZe),(Cb,Re,YZf),(Cb,Re,YZg),(Cb,Re,YZh),(Cb,Re, YZi),(Cb,Re,YZj),(Cb,R e,YZk),(Cb,Re,YZl),(Cb,Re, YZm),(Cb,Re,YZn),(Cb,Re,YZo),(Cb,Re,YZp),(Cb,Re, YZq),(C b,Re,YZr),(Cb,Re,YZs),(Cb,Re,YZt),(Cb,Re, YZu),(Cb,Re,YZy),(Cb,Re,YZw),(Cb,Re,YZx), (Cb,Re, YZy),(Cb,Re,YZz),(Cb,Re,YZaa),(Cb,Re,YZab),(Cb,Re, YZac),(Cb,Re,YZad),(Cb,R e,YZae),(Cb,Re,YZaf),(Cb,Re, YZag),(Cc,Ra,YZa),(Cc,Ra,YZb),(Cc,Ra,YZc),(Cc,Ra, YZd), (Cc,Ra,YZe),(Cc,Ra,YZaf),(Cc,Ra,YZg),(Cc,Ra, YZh),(Cc,Ra,YZi),(Cc,Ra,YZj),(Cc,Ra,YZk), (Cc,Ra,YZl), (Cc,Ra,YZm),(Cc,Ra,YZn),(Cc,Ra,YZo),(Cc,Ra,YZp),(Cc, Ra,YZq),(Cc,Ra,YZr), (Cc,Ra,YZs),(Cc,Ra,YZt),(Cc,Ra, YZu),(Cc,Ra,YZy),(Cc,Ra,YZw),(Cc,Ra,YZx),(Cc,Ra,Y Zy),(Cc,Ra,YZz),(Cc,Ra,YZaa),(Cc,Ra,YZab),(Cc,Ra, YZac),(Cc,Ra,YZad),(Cc,Ra,YZae),(C c,Ra,YZaf),(Cc,Ra, YZag),(Cc,Rb,YZa),(Cc,Rb,YZb),(Cc,Rb,YZc),(Cc,Rb, YZd),(Cc,Rb,YZe), (Cc,Rb,YZf),(Cc,Rb,YZg),(Cc,Rb, YZh),(Cc,Rb,YZi),(Cc,Rb,YZj),(Cc,Rb,YZk),(Cc,Rb,YZl), (Cc,Rb,YZm),(Cc,Rb,YZn),(Cc,Rb,YZo),(Cc,Rb,YZp), (Cc,Rb,YZq),(Cc,Rb,YZr),(Cc,Rb, YZs),(Cc,Rb,YZt),(Cc, Rb,YZu),(Cc,Rb,YZy),(Cc,Rb,YZw),(Cc,Rb,YZx),(Cc,Rb, YZy),(Cc, Rb,YZz),(Cc,Rb,YZaa),(Cc,Rb,YZab),(Cc,Rb, YZac),(Cc,Rb,YZad),(Cc,Rb,YZae),(Cc,Rb,Y Zaf),(Cc,Rb, YZag),(Cc,Rc,YZa),(Cc,Rc,YZb),(Cc,Rc,YZc),(Cc,Rc, Yal),(Cc,Rc,YZe),(Cc,R c,Ya),(Cc,Rc,YZg),(Cc,Rc,YZh), (Cc,Rc,YZi),(Cc,Rc,YZj),(Cc,Rc,YZk),(Cc,Rc,YZl),(Cc,R c,YZm),(Cc,Rc,YZn),(Cc,Rc,YZo),(Cc,Rc,YZp),(Cc,Rc, YZq),(Cc,Rc,YZr),(Cc,Rc,YZs),(Cc, Rc,YZt),(Cc,Rc,YZu), (Cc,Rc,YZy),(Cc,Rc,YZw),(Cc,Rc,YZx),(Cc,Rc,YZy),(Cc, Rc,YZz), (Cc,Rc,YZaa),(Cc,Rc,YZab),(Cc,Rc,YZac),(Cc, Rc,YZad),(Cc,Rc,YZae),(Cc,Rc,YZaf),(Cc,R c,YZag),(Cc, Rd,YZa),(Cc,Rd,YZb),(Cc,Rd,YZc),(Cc,Rd,YZd),(Cc,Rd, YZe),(Cc,Rd,YZf),(C c,Rd,YZg),(Cc,Rd,YZh),(Cc,Rd, YZi),(Cc,Rd,YZj),(Cc,Rd,YZk),(Cc,Rd,YZl),(Cc,Rd, YZm), (Cc,Rd,YZn),(Cc,Rd,YZo),(Cc,Rd,YZp),(Cc,Rd, YZq),(Cc,Rd,YZr),(Cc,Rd,YZs),(Cc,Rd,YZt), (Cc,Rd, YZu),(Cc,Rd,YZy),(Cc,Rd,YZw),(Cc,Rd,YZx),(Cc,Rd, YZy),(Cc,Rd,YZz),(Cc,Rd, YZaa),(Cc,Rd,YZab),(Cc,Rd, YZac),(Cc,Rd,YZad),(Cc,Rd,YZae),(Cc,Rd,YZaf),(Cc,Rd, YZa g) (Cc,Re,YZa),(Cc,Re,YZb),(Cc,Re,YZc),(Cc,Re, YZd),(Cc,Re,YZe),(Cc,Re,YZf),(Cc,Re,Y Zg),(Cc,Re, YZh),(Cc,Re,YZi),(Cc,Re,YZj),(Cc,Re,YZk),(Cc,Re,YZl), (Cc,Re,YZm),(Cc,Re, YZn),(Cc,Re,YZo),(Cc,Re,YZp),(Cc, Re,YZq),(Cc,Re,YZr),(Cc,Re,YZs),(Cc,Re,YZt),(Cc,Re, YZu),(Cc,Re,YZy),(Cc,Re,YZw),(Cc,Re,YZx),(Cc,Re, YZy),(Cc,Re,YZz),(Cc,Re,YZaa),(Cc, Re,YZab),(Cc,Re, YZac),(Cc,Re,YZad),(Cc,Re,YZae),(Cc,Re,YZaf),(Cc,Re, YZag),(Cd,Ra,Y Za),(Cd,Ra,YZb),(Cd,Ra,YZc),(Cd,Ra, YZd),(Cd,Ra,YZe),(Cd,Ra,YZf),(Cd,Ra,YZg),(Cd,Ra, YZh),(Cd,Ra,YZi),(Cd,Ra,YZj),(Cd,Ra,YZk),(Cd,Ra,YZl), (Cd,Ra,YZm),(Cd,Ra,YZn),(Cd, Ra,YZo),(Cd,Ra,YZp), (Cd,Ra,YZq),(Cd,Ra,YZr),(Cd,Ra,YZs),(Cd,Ra,YZt),(Cd, Ra,YZu),(C d,Ra,YZv),(Cd,Ra,YZw),(Cd,Ra,YZx),(Cd,Ra, YZy),(Cd,Ra,YZz),(Cd,Ra,YZaa),(Cd,Ra,YZa b) (Cd,Ra, YZac),(Cd,Ra,YZad),(Cd,Ra,YZae),(Cd,Ra,YZaf),(Cd,Ra, YZag),(Cd,Rb,YZa),(C d,Rb,YZb),(Cd,Rb,YZc),(Cd,Rb, YZd),(Cd,Rb,YZe),(Cd,Rb,YZf),(Cd,Rb,YZg),(Cd,Rb, YZh), (Cd,Rb,YZi),(Cd,Rb,YZj),(Cd,Rb,YZk),(Cd,Rb, YZl),(Cd,Rb,YZm),(Cd,Rb,YZn),(Cd,Rb,Y Zo),(Cd,Rb, YZp),(Cd,Rb,YZq),(Cd,Rb,YZr),(Cd,Rb,YZs),(Cd,Rb,

YZt),(Cd,Rb,YZu),(Cd,Rb, YZv),(Cd,Rb,YZw),(Cd,Rb, YZx),(Cd,Rb,YZy),(Cd,Rb,YZz),(Cd,Rb,YZaa),(Cd,Rb, YZab), (Cd,Rb,YZac),(Cd,Rb,YZad),(Cd,Rb,YZae),(Cd, Rb,YZaf),(Cd,Rb,YZag),(Cd,Rc,YZa),(Cd,R c,YZb),(Cd, Rc,YZc),(Cd,Rc,YZd),(Cd,Rc,YZe),(Cd,Rc,YZf),(Cd,Rc, YZg),(Cd,Rc,YZh),(Cd Rc,YZi),(Cd,Rc,YZj),(Cd,Rc, YZk),(Cd,Rc,YZl),(Cd,Rc,YZm),(Cd,Rc,YZn),(Cd,Rc, YZo), (Cd,Rc,YZp),(Cd,Rc,YZq),(Cd,Rc,YZr),(Cd,Rc, YZs),(Cd,Rc,YZt),(Cd,Rc,YZu),(Cd,Rc,YZy), (Cd,Rc, YZw),(Cd,Rc,YZx),(Cd,Rc,YZy),(Cd,Rc,YZz),(Cd,Rc, YZaa),(Cd,Rc,YZab),(Cd,Rc, YZac),(Cd,Rc,YZad),(Cd,Rc, YZae),(Cd,Rc,YZaf),(Cd,Rc,YZag),(Cd,Rd,YZa),(Cd,Rd, YZb), (Cd,Rd,YZc),(Cd,Rd,YZd),(Cd,Rd,YZe),(Cd,Rd, YZf),(Cd,Rd,YZg),(Cd,Rd,YZh),(Cd,Rd,Y Zi),(Cd,Rd, YZj),(Cd,Rd,YZk),(Cd,Rd,YZl),(Cd,Rd,YZm),(Cd,Rd, YZn),(Cd,Rd,YZo),(Cd,R d,YZp),(Cd,Rd,YZq),(Cd,Rd, YZr),(Cd,Rd,YZs),(Cd,Rd,YZt),(Cd,Rd,YZu),(Cd,Rd, YZy),(C d,Rd,YZw),(Cd,Rd,YZx),(Cd,Rd,YZy),(Cd,Rd, YZz),(Cd,Rd,YZaa),(Cd,Rd,YZab),(Cd,Rd,Y Zac),(Cd,Rd, YZad),(Cd,Rd,YZae),(Cd,Rd,YZaf),(Cd,Rd,YZag),(Cd,Re, YZa),(Cd,Re,YZb), (Cd,Re,YZc),(Cd,Re,YZd),(Cd,Re, YZe),(Cd,Re,YZf),(Cd,Re,YZg),(Cd,Re,YZh),(Cd,Re, YZi), (Cd,Re,YZj),(Cd,Re,YZk),(Cd,Re,YZl),(Cd,Re, YZm),(Cd,Re,YZn),(Cd,Re,YZo),(Cd,Re,Y Zp),(Cd,Re, YZq),(Cd,Re,YZr),(Cd,Re,YZs),(Cd,Re,Ya),(Cd,Re,YZu), (Cd,Re,YZy),(Cd,Re, YZw),(Cd,Re,YZx),(Cd,Re,YZy), (Cd,Re,YZz),(Cd,Re,YZaa),(Cd,Re,YZab),(Cd,Re,YZac), (Cd,Re,YZad),(Cd,Re,YZae),(Cd,Re,YZaf),(Cd,Re,YZag), (Ce,Ra,YZa),(Ce,Ra,YZb),(Ce,Ra, YZc),(Ce,Ra,YZd),(Ce, Ra,YZe),(Ce,Ra,YZf),(Ce,Ra,YZg),(Ce,Ra,YZh),(Ce,Ra, YZi),(Ce,Ra,YZj),(Ce,Ra,YZk),(Ce,Ra,YZl),(Ce,Ra,YZm), (Ce,Ra,YZn),(Ce,Ra,YZo),(Ce,Ra,YZp),(Ce, Ra,YZq),(Ce, Ra,YZr),(Ce,Ra,YZs),(Ce,Ra,YZt),(Ce,Ra,YZu),(Ce,Ra, YZy),(Ce,Ra,YZw),(C e,Ra,YZx),(Ce,Ra,YZy),(Ce,Ra, YZz),(Ce,Ra,YZaa),(Ce,Ra,YZab),(Ce,Ra,YZac),(Ce,Ra, YZ ad),(Ce,Ra,YZae),(Ce,Ra,YZaf),(Ce,Ra,YZag),(Ce,Rb, YZa),(Ce,Rb,YZb),(Ce,Rb,YZc),(Ce, Rb,YZd),(Ce,Rb, YZe),(Ce,Rb,YZf),(Ce,Rb,YZg),(Ce,Rb,YZh),(Ce,Rb, YZi),(Ce,Rb,YZj),(C e,Rb,YZk),(Ce,Rb,YZl),(Ce,Rb, YZm),(Ce,Rb,YZn),(Ce,Rb,YZo),(Ce,Rb,YZp),(Ce,Rb, YZq), (Ce,Rb,YZr),(Ce,Rb,YZs),(Ce,Rb,YZt),(Ce,Rb, YZu),(Ce,Rb,YZy),(Ce,Rb,YZw),(Ce,Rb,YZ x) (Ce,Rb, YZy),(Ce,Rb,YZz),(Ce,Rb,YZaa),(Ce,Rb,YZab),(Ce,Rb, YZac),(Ce,Rb,YZad),(Ce, Rb,YZae),(Ce,Rb,YZaf),(Ce,Rb, YZag),(Ce,Rc,YZa),(Ce,Rc,YZb),(Ce,Rc,YZc),(Ce,Rc, YZd), (Ce,Rc,YZe),(Ce,Rc,YZf),(Ce,Rc,YZg),(Ce,Rc, YZh),(Ce,Rc,YZi),(Ce,Rc,YZj),(Ce,Rc,YZk), (Ce,Rc,YZl), (Ce,Rc,YZm),(Ce,Rc,YZn),(Ce,Rc,YZo),(Ce,Rc,YZp),(Ce, Rc,YZq),(Ce,Rc,Y Zr),(Ce,Rc,YZs),(Ce,Rc,YZt),(Ce,Rc, YZu),(Ce,Rc,YZv),(Ce,Rc,YZw),(Ce,Rc,YZx),(Ce,Rc, YZy),(Ce,Rc,YZz),(Ce,Rc,YZaa),(Ce,Rc,YZab),(Ce,Rc, YZac),(Ce,Rc,YZad),(Ce,Rc,YZae), (Ce,Rc,YZaf),(Ce,Rc, YZag),(Ce,Rd,YZa),(Ce,Rd,YZb),(Ce,Rd,YZc),(Ce,Rd, YZd),(Ce,Rd,Y Ze),(Ce,Rd,YZf),(Ce,Rd,YZg),(Ce,Rd, YZg),(Ce,Rd,YZi),(Ce,Rd,YZj),(Ce,Rd,YZk),(Ce,Rd, YZl), (Ce,Rd,YZm),(Ce,Rd,YZn),(Ce,Rd,YZo),(Ce,Rd,YZp), (Ce,Rd,YZq),(Ce,Rd,YZr),(Ce, Rd,YZs),(Ce,Rd,YZt),(Ce, Rd,YZu),(Ce,Rd,YZy),(Ce,Rd,YZw),(Ce,Rd,YZx),(Ce,Rd, YZy), (Ce,Rd,YZz),(Ce,Rd,YZaa),(Ce,Rd,YZab),(Ce,Rd, YZac),(Ce,Rd,YZad),(Ce,Rd,YZae),(Ce,R d,YZaf),(Ce,Rd, YZag),(Ce,Re,YZa),(Ce,Re,YZb),(Ce,Re,YZc),(Ce,Re, YZd),(Ce,Re,YZe),(C e,Re,YZf),(Ce,Re,YZg),(Ce,Re,Ya), (Ce,Re,YZi),(Ce,Re,YZj),(Ce,Re,YZk),(Ce,Re,YZl),(C e,Re,YZm),(Ce,Re,YZn),(Ce,Re,YZo),(Ce,Re,YZp),(Ce, Re,YZq),(Ce,Re,YZr),(Ce,Re,YZs), (Ce,Re,YZt),(Ce,Re, YZu),(Ce,Re,YZv),(Ce,Re,YZw),(Ce,Re,YZx),(Ce,Re, YZy), (Ce,Re,YZ z) (Ce,Re,YZaa),(Ce,Re,YZab),(Ce,Re,
YZac),(Ce,Re,YZad),(Ce,Re,YZae),(Ce,Re,YZaf),(C e,Re, YZag),(Cf,Ra,YZa),(Cf,Ra,YZb),(Cf,Ra,YZc),(Cf,Ra, YZd),(Cf,Ra,YZe),(Cf,Ra,YZf), (Cf,Ra,YZg),(Cf,Ra,YZh), (Cf,Ra,YZi),(Cf,Ra,YZj),(Cf,Ra,YZk),(Cf,Ra,YZl),(Cf,Ra, YZm), (Cf,Ra,YZn),(Cf,Ra,YZo),(Cf,Ra,YZp),(Cf,Ra, YZq),(Cf,Ra,YZr),(Cf,Ra,YZs),(Cf,Ra,YZt), (Cf,Ra,YZu), (Cf,Ra,YZy),(Cf,Ra,YZw),(Cf,Ra,YZx),(Cf,Ra,YZy),(Cf, Ra,YZz),(Cf,Ra,YZaa), (Cf,Ra,YZab),(Cf,Ra,YZac),(Cf, Ra,YZad),(Cf,Ra,YZae),(Cf,Ra,YZaf),(Cf,Ra,YZag),(Cf, Rb, YZa),(Cf,Rb,YZb),(Cf,Rb,YZc),(Cf,Rb,YZd),(Cf,Rb, YZe),(Cf,Rb,YZf),(Cf,Rb,YZg),(Cf,Rb, YZh),(Cf,Rb,YZi), (Cf,Rb,YZj),(Cf,Rb,YZk),(Cf,Rb,YZl),(Cf,Rb,YZm),(Cf, Rb,YZn),(Cf,Rb, YZo),(Cf,Rb,YZp),(Cf,Rb,YZq),(Cf,Rb, YZr),(Cf,Rb,YZs),(Cf,Rb,YZt),(Cf,Rb,YZu),(Cf,Rb, YZv), (Cf,Rb,YZw),(Cf,Rb,YZx),(Cf,Rb,YZy),(Cf,Rb,YZz),(Cf, Rb,YZaa),(Cf,Rb,YZab),(Cf, Rb,YZac),(Cf,Rb,YZad),(Cf, Rb,YZae),(Cf,Rb,YZaf),(Cf,Rb,YZag),(Cf,Rc,YZa),(Cf, Rc,YZ b) (Cf,Rc,YZc),(Cf,Rc,YZd),(Cf,Rc,YZe),(Cf,Rc, YZf),(Cf,Rc,YZg),(Cf,Rc,YZh),(Cf,Rc,YZi), (Cf,Rc,YZj), (Cf,Rc,YZk),(Cf,Rc,YZl),(Cf,Rc,YZm),(Cf,Rc,YZn),(Cf, Rc,YZo),(Cf,Rc,YZp), (Cf,Rc,YZq),(Cf,Rc,YZr),(Cf,Rc, YZs),(Cf,Rc,YZt),(Cf,Rc,YZu),(Cf,Rc,YZy),(Cf,Rc,YZw), (Cf,Rc,YZx),(Cf,Rc,YZy),(Cf,Rc,YZz),(Cf,Rc,YZaa),(Cf, Rc,YZab),(Cf,Rc,YZac),(Cf,Rc,Y Zad),(Cf,Rc,YZae),(Cf, Rc,YZaf),(Cf,Rc,YZag),(Cf,Rd,YZa),(Cf,Rd,YZb),(Cf,Rd, YZc),(Cf, Rd,YZd),(Cf,Rd,YZe),(Cf,Rd,YZf),(Cf,Rd,YZg), (Cf,Rd,YZh),(Cf,Rd,YZi),(Cf,Rd,YZj),(Cf, Rd,YZk),(Cf, Rd,YZl),(Cf,Rd,YZm),(Cf,Rd,YZn),(Cf,Rd,YZo),(Cf,Rd, YZp),(Cf,Rd,YZq),(C f,Rd,YZr),(Cf,Rd,YZs),(Cf,Rd,YZt), (Cf,Rd,YZu),(Cf,Rd,YZv),(Cf,Rd,YZw),(Cf,Rd,YZx), (Cf, Rd,YZy),(Cf,Rd,YZz),(Cf,Rd,YZaa),(Cf,Rd,YZab),(Cf,Rd, YZac),(Cf,Rd,YZad),(Cf,Rd,Y Zae),(Cf,Rd,YZaf),(Cf,Rd, YZag),(Cf,Re,YZa),(Cf,Re,YZb),(Cf,Re,YZc),(Cf,Re, YZd),(Cf,R e,YZe),(Cf,Re,YZf),(Cf,Re,YZg),(Cf,Re,YZh), (Cf,Re,YZi),(Cf,Re,YZj),(Cf,Re,YZk),(Cf,Re, YZl),(Cf,Re, YZm),(Cf,Re,YZn),(Cf,Re,YZo),(Cf,Re,YZp),(Cf,Re, YZq),(Cf,Re,YZr),(Cf,Re, YZs),(Cf,Re,YZt),(Cf,Re,YZu), (Cf,Re,YZv),(Cf,Re,YZw),(Cf,Re,YZx),(Cf,Re,YZy),(Cf, Re, YZz),(Cf,Re,YZaa),(Cf,Re,YZab),(Cf,Re,YZac),(Cf, Re,YZad),(Cf,Re,YZae),(Cf,Re,YZaf), (Cf,Re,YZag),(Cg, Ra,YZa),(Cg,Ra,YZb),(Cg,Ra,YZc),(Cg,Ra,YZd),(Cg,Ra, YZe),(Cg,Ra,YZ f),(Cg,Ra,YZg),(Cg,Ra,Ya),(Cg,Ra,YZi), (Cg,Ra,YZj),(Cg,Ra,YZk),(Cg,Ra,YZl),(Cg,Ra,Y Zm),(Cg, Ra,YZn),(Cg,Ra,YZo),(Cg,Ra,YZp),(Cg,Ra,YZq),(Cg,Ra, YZr),(Cg,Ra,YZs),(Cg,R a,YZt),(Cg,Ra,YZu),(Cg,Ra, YZv),(Cg,Ra,YZw),(Cg,Ra,YZx),(Cg,Ra,YZy),(Cg,Ra, YZz),(C g,Ra,YZaa),(Cg,Ra,YZab),(Cg,Ra,YZac),(Cg,Ra, YZad),(Cg,Ra,YZae),(Cg,Ra,YZaf),(Cg,Ra, YZag),(Cg,Rb, YZa),(Cg,Rb,YZb),(Cg,Rb,YZc),(Cg,Rb,YZd),(Cg,Rb, YZe),(Cg,Rb,YZf),(Cg, Rb,YZg),(Cg,Rb,YZh),(Cg,Rb, YZi),(Cg,Rb,YZj),(Cg,Rb,YZk),(Cg,Rb,YZl),(Cg,Rb, YZm), (Cg,Rb,YZn),(Cg,Rb,YZo),(Cg,Rb,YZp),(Cg,Rb, YZq),(Cg,Rb,YZr),(Cg,Rb,YZs),(Cg,Rb,YZ t),(Cg,Rb, YZu),(Cg,Rb,YZy),(Cg,Rb,YZw),(Cg,Rb,YZx),(Cg,Rb, YZy),(Cg,Rb,YZz),(Cg,Rb, YZaa),(Cg,Rb,YZab),(Cg,Rb, YZac),(Cg,Rb,YZad),(Cg,Rb,YZae),(Cg,Rb,YZaf),(Cg,Rb, YZ ag),(Cg,Rc,YZa),(Cg,Rc,YZb),(Cg,Rc,YZc),(Cg,Rc, YZd),(Cg,Rc,YZe),(Cg,Rc,YZf),(Cg,Rc, YZg),(Cg,Rc, YZh),(Cg,Rc,YZi),(Cg,Rc,YZj),(Cg,Rc,YZk),(Cg,Rc,YZl), (Cg,Rc,YZm),(Cg,R c,YZn),(Cg,Rc,YZo),(Cg,Rc,YZp), (Cg,Rc,YZq),(Cg,Rc,YZr),(Cg,Rc,YZs),(Cg,Rc,YZt),(Cg, Rc,YZu),(Cg,Rc,YZv),(Cg,Rc,YZw),(Cg,Rc,YZx),(Cg,Rc, YZy),(Cg,Rc,YZz),(Cg,Rc,YZaa), (Cg,Rc,YZab),(Cg,Rc, YZac),(Cg,Rc,YZad),(Cg,Rc,YZae),(Cg,Rc,YZaf),(Cg,Rc, YZag),(Cg, Rd,YZa),(Cg,Rd,YZb),(Cg,Rd,YZc),(Cg,Rd, YZd),(Cg,Rd,YZe),(Cg,Rd,YZf),(Cg,Rd,YZg), (Cg,Rd, YZh),(Cg,Rd,YZi),(Cg,Rd,YZj),(Cg,Rd,YZk),(Cg,Rd,

YZl),(Cg,Rd,YZm),(Cg,Rd,YZn) (Cg,Rd,YZo),(Cg,Rd, YZp),(Cg,Rd,YZq),(Cg,Rd,YZr),(Cg,Rd,YZs),(Cg,Rd, YZt),(Cg,Rd, YZu),(Cg,Rd,YZy),(Cg,Rd,YZw),(Cg,Rd, YZx),(Cg,Rd,YZy),(Cg,Rd,YZz),(Cg,Rd,YZaa),(C g,Rd, YZab),(Cg,Rd,YZac),(Cg,Rd,YZad),(Cg,Rd,YZae),(Cg,Rd, YZaf),(Cg,Rd,YZag),(Cg,R e,YZa),(Cg,Re,YZb),(Cg,Re, YZc),(Cg,Re,YZd),(Cg,Re,YZe),(Cg,Re,YZf),(Cg,Re, YZg),(Cg, Re,YZh),(Cg,Re,YZi),(Cg,Re,YZj),(Cg,Re, YZk),(Cg,Re,YZl),(Cg,Re,YZm),(Cg,Re,YZn), (Cg,Re, YZo),(Cg,Re,YZp),(Cg,Re,YZq),(Cg,Re,YZr),(Cg,Re, YZs),(Cg,Re,YZt),(Cg,Re,YZu), (Cg,Re,YZy),(Cg,Re, YZw),(Cg,Re,YZx),(Cg,Re,YZy),(Cg,Re,YZz),(Cg,Re, YZaa),(Cg,Re, YZab),(Cg,Re,YZac),(Cg,Re,YZad),(Cg,Re, YZae),(Cg,Re,YZaf),(Cg,Re,YZag),(Ch,Ra,YZa), (Ch,Ra, YZb),(Ch,Ra,YZc),(Ch,Ra,YZd),(Ch,Ra,YZe),(Ch,Ra, YZf),(Ch,Ra,YZg),(Ch,Ra,Y Zh),(Ch,Ra,YZi),(Ch,Ra, YZj),(Ch,Ra,YZk),(Ch,Ra,YZl),(Ch,Ra,YZm),(Ch,Ra, YZn),(Ch,Ra, YZo),(Ch,Ra,YZp),(Ch,Ra,YZq),(Ch,Ra, YZr),(Ch,Ra,YZs),(Ch,Ra,YZt),(Ch,Ra,YZu),(Ch,R a,YZy),(Ch,Ra,YZw),(Ch,Ra,YZx),(Ch,Ra,YZy),(Ch,Ra, YZz),(Ch,Ra,YZaa),(Ch,Ra,YZab), (Ch,Ra,YZac),(Ch,Ra, YZad),(Ch,Ra,YZae),(Ch,Ra,YZaf),(Ch,Ra,YZag),(Ch,Rb, YZa),(Ch,R b,YZb),(Ch,Rb,YZc),(Ch,Rb,YZd),(Ch,Rb, YZe),(Ch,Rb,YZf),(Ch,Rb,YZg),(Ch,Rb,YZh),(C h,Rb, YZi),(Ch,Rb,YZj),(Ch,Rb,YZk),(Ch,Rb,YZl),(Ch,Rb, YZm),(Ch,Rb,YZn),(Ch,Rb,YZo), (Ch,Rb,YZp),(Ch,Rb, YZq),(Ch,Rb,YZr),(Ch,Rb,YZs),(Ch,Rb,YZt),(Ch,Rb, YZu),(Ch,Rb,Y Zv),(Ch,Rb,YZw),(Ch,Rb,YZx),(Ch,Rb, YZy),(Ch,Rb,YZz),(Ch,Rb,YZaa),(Ch,Rb,YZab),(C h,Rb, YZac),(Ch,Rb,YZad),(Ch,Rb,YZae),(Ch,Rb,YZaf),(Ch,Rb, YZag),(Ch,Rc,YZa),(Ch,Rc, YZb),(Ch,Rc,YZc),(Ch,Rc, YZd),(Ch,Rc,YZe),(Ch,Rc,YZf),(Ch,Rc,YZg),(Ch,Rc, YZh),(Ch, Rc,YZi),(Ch,Rc,YZj),(Ch,Rc,YZk),(Ch,Rc, YZl),(Ch,Rc,YZm),(Ch,Rc,YZn),(Ch,Rc,YZo),(C h,Rc, YZp),(Ch,Rc,YZq),(Ch,Rc,YZr),(Ch,Rc,YZs),(Ch,Rc, YZt),(Ch,Rc,YZu),(Ch,Rc,YZy), (Ch,Rc,YZw),(Ch,Rc, YZx),(Ch,Rc,YZy),(Ch,Rc,YZz),(Ch,Rc,YZaa),(Ch,Rc, YZab),(Ch,Rc, YZac),(Ch,Rc,YZad),(Ch,Rc,YZae),(Ch,Rc, YZaf),(Ch,Rc,YZag),(Ch,Rd,YZa),(Ch,Rd,YZb), (Ch,Rd, YZc),(Ch,Rd,YZd),(Ch,Rd,YZe),(Ch,Rd,YZf),(Ch,Rd, YZg),(Ch,Rd,YZh),(Ch,Rd,Y Zi),(Ch,Rd,YZj),(Ch,Rd, YZk),(Ch,Rd,YZl),(Ch,Rd,YZm),(Ch,Rd,YZn),(Ch,Rd, YZo),(Ch,R d,YZp),(Ch,Rd,YZq),(Ch,Rd,YZr),(Ch,Rd, YZs),(Ch,Rd,YZt),(Ch,Rd,YZu),(Ch,Rd,YZy),(C h,Rd, YZw),(Ch,Rd,YZx),(Ch,Rd,YZy),(Ch,Rd,YZz),(Ch,Rd, YZaa),(Ch,Rd,YZab),(Ch,Rd,Y Zac),(Ch,Rd,YZad),(Ch, Rd,YZae),(Ch,Rd,YZaf),(Ch,Rd,YZag),(Ch,Re,YZa),(Ch, Re,YZb), (Ch,Re,YZc),(Ch,Re,YZd),(Ch,Re,YZe),(Ch,Re, YZf),(Ch,Re,YZg),(Ch,Re,YZh),(Ch,Re,YZi), (Ch,Re, YZj),(Ch,Re,YZk),(Ch,Re,YZl),(Ch,Re,YZm),(Ch,Re, YZn),(Ch,Re,YZo),(Ch,Re,Y Zp),(Ch,Re,YZq),(Ch,Re, YZr),(Ch,Re,YZs),(Ch,Re,YZt),(Ch,Re,YZu),(Ch,Re, YZy),(Ch,Re, YZw),(Ch,Re,YZx),(Ch,Re,YZy),(Ch,Re, YZz),(Ch,Re,YZaa),(Ch,Re,YZab),(Ch,Re,YZac), (Ch,Re, YZad),(Ch,Re,YZae),(Ch,Re,YZaf),(Ch,Re,YZag),(Ci,Ra, YZa),(Ci,Ra,YZb),(Ci,Ra,Y Zc),(Ci,Ra,YZd),(Ci,Ra,YZe), (Ci,Ra,YZf),(Ci,Ra,YZg),(Ci,Ra,YZh),(Ci,Ra,YZi),(Ci,Ra, YZj), (Ci,Ra,YZk),(Ci,Ra,YZl),(Ci,Ra,YZm),(Ci,Ra,YZn), (Ci,Ra,YZo),(Ci,Ra,YZp),(Ci,Ra,YZq), (Ci,Ra,YZr),(Ci, Ra,YZs),(Ci,Ra,YZt),(Ci,Ra,YZu),(Ci,Ra,YZy),(Ci,Ra, YZw),(Ci,Ra,YZx), (Ci,Ra,YZy),(Ci,Ra,YZz),(Ci,Ra, YZaa),(Ci,Ra,YZab),(Ci,Ra,YZac),(Ci,Ra,YZad),(Ci,Ra, YZ ae),(Ci,Ra,YZaf),(Ci,Ra,YZag),(Ci,Rb,YZa),(Ci,Rb, YZb),(Ci,Rb,YZc),(Ci,Rb,YZd),(Ci,Rb, YZe),(Ci,Rb,Ya), (Ci,Rb,YZg),(Ci,Rb,YZh),(Ci,Rb,YZi),(Ci,Rb,YZj),(Ci,Rb, YZk),(Ci,Rb,Y Zl),(Ci,Rb,YZm),(Ci,Rb,YZn),(Ci,Rb, YZo),(Ci,Rb,YZp),(Ci,Rb,YZq),(Ci,Rb,YZr),(Ci,Rb,Y Zs), (Ci,Rb,YZt),(Ci,Rb,YZu),(Ci,Rb,YZv),(Ci,Rb,YZw),(Ci, Rb,YZx),(Ci,Rb,YZy),(Ci,Rb,Y Zz),(Ci,Rb,YZaa),(Ci,Rb, YZab),(Ci,Rb,YZac),(Ci,Rb,YZad),(Ci,Rb,YZae),(Ci,Rb, YZaf),(Ci, Rb,YZag),(Ci,Rc,YZa),(Ci,Rc,YZb),(Ci,Rc, YZc),(Ci,Rc,YZd),(Ci,Rc,YZe),(Ci,Rc,YZf),(Ci, Rc,YZg), (Ci,Rc,YZh),(Ci,Rc,YZi),(Ci,Rc,YZj),(Ci,Rc,YZk),(Ci,Rc, YZl),(Ci,Rc,YZm),(Ci,R c,YZn),(Ci,Rc,YZo),(Ci,Rc,YZp), (Ci,Rc,YZq),(Ci,Rc,YZr),(Ci,Rc,YZs),(Ci,Rc,YZt),(Ci,Rc, YZu),(Ci,Rc,YZy),(Ci,Rc,YZw),(Ci,Rc,YZx),(Ci,Rc,YZy), (Ci,Rc,YZz),(Ci,Rc,YZaa),(Ci,Rc, YZab),(Ci,Rc,YZac),(Ci, Rc,YZad),(Ci,Rc,YZae),(Ci,Rc,YZaf),(Ci,Rc,YZag),(Ci, Rd,YZa), (Ci,Rd,YZb),(Ci,Rd,YZc),(Ci,Rd,YZd),(Ci,Rd, YZe),(Ci,Rd,YZf),(Ci,Rd,YZg),(Ci,Rd,YZh), (Ci,Rd,YZi), (Ci,Rd,YZj),(Ci,Rd,YZk),(Ci,Rd,YZl),(Ci,Rd,YZm),(Ci, Rd,YZn),(Ci,Rd,YZo), (Ci,Rd,YZp),(Ci,Rd,YZq),(Ci,Rd, YZr),(Ci,Rd,YZs),(Ci,Rd,YZt),(Ci,Rd,YZu),(Ci,Rd,YZy), (Ci,Rd,YZw),(Ci,Rd,YZx),(Ci,Rd,YZy),(Ci,Rd,YZz),(Ci, Rd,YZaa),(Ci,Rd,YZab),(Ci,Rd,YZa c) (Ci,Rd,YZad),(Ci, Rd,YZae),(Ci,Rd,YZaf),(Ci,Rd,YZag),(Ci,Re,YZa),(Ci,Re, YZb),(Ci,Re, YZc),(Ci,Re,YZd),(Ci,Re,YZe),(Ci,Re,YZf), (Ci,Re,YZg),(Ci,Re,YZh),(Ci,Re,YZi),(Ci,Re,Y Zj),(Ci,Re, YZk),(Ci,Re,YZl),(Ci,Re,YZm),(Ci,Re,YZn),(Ci,Re,YZo), (Ci,Re,YZp),(Ci,Re,YZ q) (Ci,Re,YZr),(Ci,Re,YZs),(Ci,Re, YZt),(Ci,Re,YZu),(Ci,Re,YZy),(Ci,Re,YZw),(Ci,Re,YZx), (Ci,Re,YZy),(Ci,Re,YZz),(Ci,Re,YZaa),(Ci,Re,YZab),(Ci, Re,YZac),(Ci,Re,YZad),(Ci,Re, YZae),(Ci,Re,YZaf),(Ci,R- e,YZag),(Cj,Ra,YZa),(Cj,Ra,YZb),(Cj,Ra,YZc),(Cj,Ra, YZd),(Cj,R a,YZe),(Cj,Ra,YZf),(Cj,Ra,YZg),(Cj,Ra,YZh), (Cj,Ra,YZi),(Cj,Ra,YZj),(Cj,Ra,YZk),(Cj,Ra, YZl),(Cj,Ra, YZm),(Cj,Ra,YZn),(Cj,Ra,YZo),(Cj,Ra,YZp),(Cj,Ra,YZq), (Cj,Ra,YZr),(Cj,Ra, YZs),(Cj,Ra,YZt),(Cj,Ra,YZu),(Cj,Ra, YZy),(Cj,Ra,YZw),(Cj,Ra,YZx),(Cj,Ra,YZy),(Cj,Ra, YZz), (Cj,Ra,YZaa),(Cj,Ra,YZab),(Cj,Ra,YZac),(Cj,Ra,YZad), (Cj,Ra,YZae),(Cj,Ra,YZaf),(C j,Ra,YZag),(Cj,Rb,YZa),(Cj, Rb,YZb),(Cj,Rb,YZc),(Cj,Rb,YZd),(Cj,Rb,YZe),(Cj,Rb, YZf),(C j,Rb,YZg),(Cj,Rb,YZh),(Cj,Rb,YZi),(Cj,Rb,YZj), (Cj,Rb,YZk),(Cj,Rb,YZl),(Cj,Rb,YZm),(Cj, Rb,YZn),(Cj, Rb,YZo),(Cj,Rb,YZp),(Cj,Rb,YZq),(Cj,Rb,YZr),(Cj,Rb, YZs),(Cj,Rb,YZt),(Cj, Rb,YZu),(Cj,Rb,YZy),(Cj,Rb,YZw), (Cj,Rb,YZx),(Cj,Rb,YZy),(Cj,Rb,YZz),(Cj,Rb,YZaa),(C j,Rb,YZab),(Cj,Rb,YZac),(Cj,Rb,YZad),(Cj,Rb,YZae),(Cj, Rb,YZaf),(Cj,Rb,YZag),(Cj,Rc,Y Za),(Cj,Rc,YZb),(Cj,Rc, YZc),(Cj,Rc,YZd),(Cj,Rc,YZe),(Cj,Rc,YZf),(Cj,Rc,YZg), (Cj,Rc,YZ h) (Cj,Rc,YZi),(Cj,Rc,YZj),(Cj,Rc,YZ,k),(Cj,Rc, YZl),(Cj,Rc,YZm),(Cj,Rc,YZn),(Cj,Rc,YZo), (Cj,Rc,YZp), (Cj,Rc,YZq),(Cj,Rc,YZr),(Cj,Rc,YZs),(Cj,Rc,YZt),(Cj,Rc, YZu),(Cj,Rc,YZy), (Cj,Rc,YZw),(Cj,Rc,YZx),(Cj,Rc, YZy),(Cj,Rc,YZz),(Cj,Rc,YZaa),(Cj,Rc,YZab),(Cj,Rc, YZac), (Cj,Rc,YZad),(Cj,Rc,YZae),(Cj,Rc,YZaf),(Cj,Rc, YZag),(Cj,Rd,YZa),(Cj,Rd,YZb),(Cj,Rd, YZc),(Cj,Rd, YZd),(Cj,Rd,YZe),(Cj,Rd,YZf),(Cj,Rd,YZg),(Cj,Rd,YZh), (Cj,Rd,YZi),(Cj,Rd, YZj),(Cj,Rd,YZk),(Cj,Rd,YZl),(Cj,Rd, YZm),(Cj,Rd,YZn),(Cj,Rd,YZo),(Cj,Rd,YZp),(Cj,Rd, YZq),(Cj,Rd,YZr),(Cj,Rd,YZs),(Cj,Rd,YZt),(Cj,Rd,YZu), (Cj,Rd,YZy),(Cj,Rd,YZw),(Cj,Rd, YZx),(Cj,Rd,YZy),(Cj, Rd,YZz),(Cj,Rd,YZaa),(Cj,Rd,YZab),(Cj,Rd,YZac),(Cj, Rd,YZad),(Cj, Rd,YZae),(Cj,Rd,YZaf),(Cj,Rd,YZag),(Cj, Re,YZa),(Cj,Re,YZb),(Cj,Re,YZc),(Cj,Re,YZd), (Cj,Re, YZe),(Cj,Re,YZf),(Cj,Re,YZg),(Cj,Re,YZh),(Cj,Re,YZi), (Cj,Re,YZj),(Cj,Re,YZk),(Cj, Re,YZl),(Cj,Re,YZm),(Cj, Re,YZn),(Cj,Re,YZo),(Cj,Re,YZp),(Cj,Re,YZq),(Cj,Re, YZr),(Cj, Re,YZs),(Cj,Re,YZt),(Cj,Re,YZu),(Cj,Re,YZv), (Cj,Re,YZw),(Cj,Re,YZx),(Cj,Re,YZy),(Cj, Re,YZz),(Cj, Re,YZaa),(Cj,Re,YZab),(Cj,Re,YZac),(Cj,Re,YZad),(Cj, Re,YZae),(Cj,Re,YZaf), (Cj,Re,YZag),(Ck,Ra,YZa),(Ck, Ra,YZb),(Ck,Ra,YZc),(Ck,Ra,YZd),(Ck,Ra,YZe),(Ck,Ra, YZf),(Ck,Ra,YZg),(Ck,Ra,YZh),(Ck,Ra,YZi),(Ck,Ra,YZj), (Ck,Ra,YZk),(Ck,Ra,YZl),(Ck,Ra,YZm),(Ck,Ra,YZn),(Ck,Ra,YZo),(Ck,Ra,YZp),(Ck,Ra,YZq),(Ck,Ra,YZr),(Ck,Ra,YZs),(Ck,Ra,YZt),(Ck,Ra,YZu),(Ck,Ra,YZv),(Ck,Ra,YZw),(Ck,Ra,YZx),(Ck,Ra,YZy),(Ck,Ra,YZz),(Ck,Ra,YZaa),(Ck,Ra,YZab),(Ck,Ra,YZac),(Ck,Ra,YZad),(Ck,Ra,YZae),(Ck,Ra,YZaf),(Ck,R a,YZag),(Ck,Rb,YZa),(Ck,Rb,YZb),(Ck,Rb,YZc),(Ck,Rb,YZd),(Ck,Rb,YZe),(Ck,Rb,YZf), (Ck,Rb,YZg),(Ck,Rb,YZh),(Ck,Rb,YZi),(Ck,Rb,YZj),(Ck,Rb,YZk),(Ck,Rb,YZl),(Ck,Rb,YZ m) (Ck,Rb,YZn),(Ck,Rb,YZo),(Ck,Rb,YZp),(Ck,Rb,YZq),(Ck,Rb,YZr),(Ck,Rb,YZs),(Ck,Rb, YZt),(Ck,Rb,YZu),(Ck,Rb,YZY),(Ck,Rb,YZw),(Ck,Rb,YZx),(Ck,Rb,YZy),(Ck,Rb,YZz),(Ck, Rb,YZaa),(Ck,Rb,YZab),(Ck,Rb,YZac),(Ck,Rb,YZad),(Ck,Rb,YZae),(Ck,Rb,YZaf),(Ck,Rb, YZag),(Ck,Rc,YZa),(Ck,Rc,YZb),(Ck,Rc,YZc),(Ck,Rc,YZd),(Ck,Rc,YZe),(Ck,Rc,YZf),(Ck, Rc,YZg),(Ck,Rc,YZh),(Ck,Rc,YZi),(Ck,Rc,YZj),(Ck,Rc,YZk),(Ck,Rc,YZl),(Ck,Rc,YZm),(C k,Rc,YZn),(Ck,Rc,YZo),(Ck,Rc,YZp),(Ck,Rc,YZq),(Ck,Rc,YZr),(Ck,Rc,YZs),(Ck,Rc,YZt), (Ck,Rc,YZu),(Ck,Rc,YZv),(Ck,Rc,YZw),(Ck,Rc,YZx),(Ck,Rc,YZy),(Ck,Rc,YZz),(Ck,Rc,YZ aa),(Ck,Rc,YZab),(Ck,Rc,YZac),(Ck,Rc,YZad),(Ck,Rc,YZae),(Ck,Rc,YZaf),(Ck,Rc,YZag), (Ck,Rd,YZa),(Ck,Rd,YZb),(Ck,Rd,YZc),(Ck,Rd,YZd),(Ck,Rd,YZe),(Ck,Rd,YZf),(Ck,Rd,YZ g) (Ck,Rd,YZh),(Ck,Rd,YZi),(Ck,Rd,YZj),(Ck,Rd,YZk),(Ck,Rd,YZl),(Ck,Rd,YZm),(Ck,Rd, YZn),(Ck,Rd,YZo),(Ck,Rd,YZp),(Ck,Rd,YZq),(Ck,Rd,YZr),(Ck,Rd,YZs),(Ck,Rd,YZt),(Ck, Rd,YZu),(Ck,Rd,YZy),(Ck,Rd,YZw),(Ck,Rd,YZx),(Ck,Rd,YZy),(Ck,Rd,YZz),(Ck,Rd,YZaa), (Ck,Rd,YZab),(Ck,Rd,YZac),(Ck,Rd,YZad),(Ck,Rd,YZae),(Ck,Rd,YZaf),(Ck,Rd,YZag),(C k,Re,YZa),(Ck,Re,YZb),(Ck,Re,YZc),(Ck,Re,YZd),(Ck,Re,YZe),(Ck,Re,YZf),(Ck,Re,YZg), (Ck,Re,YZh),(Ck,Re,YZi),(Ck,Re,YZj),(Ck,Re,YZk),(Ck,Re,YZl),(Ck,Re,YZm),(Ck,Re,YZ n) (Ck,Re,YZo),(Ck,Re,YZp),(Ck,Re,YZq),(Ck,Re,YZr),(Ck,Re,YZs),(Ck,Re,YZt),(Ck,Re,Y Zu),(Ck,Re,YZy),(Ck,Re,YZw),(Ck,Re,YZx),(Ck,Re,YZy),(Ck,Re,YZz),(Ck,Re,YZaa),(Ck, Re,YZab),(Ck,Re,YZac),(Ck,Re,YZad),(Ck,Re,YZae),(Ck,Re,YZaf),(Ck,Re,YZag),(Ck,Ra,Y Za),(Cl,Ra,YZb),(Cl,Ra,YZc),(Cl,Ra,YZd),(Cl,Ra,YZe),(Cl,Ra,YZf),(Cl,Ra,YZg),(Cl,Ra,YZ h) (Cl,Ra,YZi),(Cl,Ra,YZj),(Cl,Ra,YZk),(Cl,Ra,YZl),(Cl,Ra,YZm),(Cl,Ra,YZn),(Cl,Ra,YZo),(Cl,Ra,YZp),(Cl,Ra,YZq),(Cl,Ra,YZr),(Cl,Ra,YZs),(Cl,Ra,YZt),(Cl,Ra,YZu),(Cl,Ra,YZY), (Cl,Ra,YZw),(Cl,Ra,YZx),(Cl,Ra,YZy),(Cl,Ra,YZz),(Cl,Ra,YZaa),(Cl,Ra,YZab),(Cl,Ra,YZac), (Cl,Ra,YZad),(Cl,Ra,YZae),(Cl,Ra,YZaf),(Cl,Ra,YZag),(Cl,Rb,YZa),(Cl,Rb,YZb),(Cl,Rb, YZc),(Cl,Rb,YZd),(Cl,Rb,YZe),(Cl,Rb,YZf),(Cl,Rb,YZg),(Cl,Rb,YZh),(Cl,Rb,YZi),(Cl,Rb,YZj),(Cl,Rb,YZk),(Cl,Rb,YZl),(Cl,Rb,YZm),(Cl,Rb,YZn),(Cl,Rb,YZo),(Cl,Rb,YZp),(Cl,Rb, YZq),(Cl,Rb,YZr),(Cl,Rb,YZs),(Cl,Rb,YZt),(Cl,Rb,YZu),(Cl,Rb,YZy),(Cl,Rb,YZw),(Cl,Rb, YZx),(Cl,Rb,YZy),(Cl,Rb,YZz),(Cl,Rb,YZaa),(Cl,Rb,YZab),(Cl,Rb,YZac),(Cl,Rb,YZad),(Cl, Rb,YZae),(Cl,Rb,YZaf),(Cl,Rb,YZag),(Cl,Rc,YZa),(Cl,Rc,YZb),(Cl,Rc,YZc),(Cl,Rc,YZd), (Cl,Rc,YZe),(Cl,Rc,YZf),(Cl,Rc,YZg),(Cl,Rc,YZh),(Cl,Rc,YZi),(Cl,Rc,YZj),(Cl,Rc,YZk),(Cl, Rc,YZl),(Cl,Rc,YZm),(Cl,Rc,YZn),(Cl,Rc,YZo),(Cl,Rc,YZp),(Cl,Rc,YZq),(Cl,Rc,YZr),(Cl, Rc,YZs),(Cl,Rc,YZt),(Cl,Rc,YZu),(Cl,Rc,YZv),(Cl,Rc,YZw),(Cl,Rc,YZx),(Cl,Rc,YZy),(Cl, Rc,YZz),(Cl,Rc,YZaa),(Cl,Rc,YZab),(Cl,Rc,YZac),(Cl,Rc,YZad),(Cl,Rc,YZae),(Cl,Rc,YZaf), (Cl,Rc,YZag),(Cl,Rd,YZa),(Cl,Rd,YZb),(Cl,Rd,YZc),(Cl,Rd,YZd),(Cl,Rd,YZe),(Cl,Rd,YZf), (Cl,Rd,YZg),(Cl,Rd,YZh),(Cl,Rd,YZi),(Cl,Rd,YZj),(Cl,Rd,YZk),(Cl,Rd,YZl),(Cl,Rd,YZm), (Cl,Rd,YZn),(Cl,Rd,YZo),(Cl,Rd,YZp),(Cl,Rd,YZq),(Cl,Rd,YZr),(Cl,Rd,YZs),(Cl,Rd,YZt), (Cl,Rd,YZu),(Cl,Rd,YZy),(Cl,Rd,YZw),(Cl,Rd,YZx),(Cl,Rd,YZy),(Cl,Rd,YZz),(Cl,Rd,YZaa), (Cl,Rd,YZab),(Cl,Rd,YZac),(Cl,Rd,YZad),(Cl,Rd,YZae),(Cl,Rd,YZaf),(Cl,Rd,YZag),(Cl,Re, YZa),(Cl,Re,YZb),(Cl,Re,YZc),(Cl,Re,YZd),(Cl,Re,YZe),(Cl,Re,YZf),(Cl,Re,YZg),(Cl,Re, YZh),(Cl,Re,YZi),(Cl,Re,YZj),(Cl,Re,YZl),(Cl,Re,YZm),(Cl,Re,YZn),(Cl,Re,Y Zo),(Cl,Re,YZp),(Cl,Re,YZq),(Cl,Re,YZr),(Cl,Re,YZs),(Cl,Re,YZt),(Cl,Re,YZu),(Cl,Re,YZ v),(Cl,Re,YZw),(Cl,Re,YZx),(Cl,Re,YZy),(Cl,Re,YZz),(Cl,Re,YZaa),(Cl,Re,YZab),(Cl,Re,Y Zac),(Cl,Re,YZad),(Cl,Re,YZae),(Cl,Re,YZaf),(Cl,Re,YZag),(Cm,Ra,YZa),(Cm,Ra,YZb),(C m,Ra,YZc),(Cm,Ra,YZd),(Cm,Ra,YZe),(Cm,Ra,YZf),(Cm,Ra,YZg),(Cm,Ra,YZh),(Cm,Ra, YZi),(Cm,Ra,YZj),(Cm,Ra,Ya),(Cm,Ra,YZl),(Cm,Ra,YZm),(Cm,Ra,YZn),(Cm,Ra,YZo), (Cm,Ra,YZp),(Cm,Ra,YZq),(Cm,Ra,YZr),(Cm,Ra,YZs),(Cm,Ra,YZt),(Cm,Ra,YZu),(Cm,Ra, YZv),(Cm,Ra,YZw),(Cm,Ra,YZx),(Cm,Ra,YZy),(Cm,Ra,YZz),(Cm,Ra,YZaa),(Cm,Ra,YZa b) (Cm,Ra,YZac),(Cm,Ra,YZad),(Cm,Ra,YZae),(Cm,Ra,YZaf),(Cm,Ra,YZag),(Cm,Rb,YZa), (Cm,Rb,YZb),(Cm,Rb,YZc),(Cm,Rb,YZd),(Cm,Rb,YZe),(Cm,Rb,YZf),(Cm,Rb,YZg),(Cm, Rb,YZh),(Cm,Rb,YZi),(Cm,Rb,YZj),(Cm,Rb,YZk),(Cm,Rb,YZl),(Cm,Rb,YZm),(Cm,Rb,YZ n) (Cm,Rb,YZo),(Cm,Rb,YZp),(Cm,Rb,YZq),(Cm,Rb,YZr),(Cm,Rb,YZs),(Cm,Rb,YZt),(Cm, Rb,YZu),(Cm,Rb,YZv),(Cm,Rb,YZw),(Cm,Rb,YZx),(Cm,Rb,YZy),(Cm,Rb,YZz),(Cm,Rb, YZaa),(Cm,Rb,YZab),(Cm,Rb,YZac),(Cm,Rb,YZad),(Cm,Rb,YZae),(Cm,Rb,YZaf),(Cm,Rb, YZag),(Cm,Rc,YZa),(Cm,Rc,YZb),(Cm,Rc,YZc),(Cm,Rc,YZd),(Cm, Rc,YZe),(Cm,Rc,YZf), (Cm,Rc,YZg),(Cm,Rc,YZh),(Cm, Rc,YZi),(Cm,Rc,YZj),(Cm,Rc,YZk),(Cm,Rc,YZl),(Cm,Rc, YZm),(Cm,Rc,YZn),(Cm,Rc,YZo),(Cm,Rc,YZp),(Cm,Rc, YZq),(Cm,Rc,YZr),(Cm,Rc,YZs), (Cm,Rc,YZt),(Cm,Rc, YZu),(Cm,Rc,YZy),(Cm,Rc,YZw),(Cm,Rc,YZx),(Cm,Rc, YZy),(Cm,R c,YZz),(Cm,Rc,YZaa),(Cm,Rc,YZab),(Cm, Rc,YZac),(Cm,Rc,YZad),(Cm,Rc,YZae),(Cm,Rc, YZaf), (Cm,Rc,YZag),(Cm,Rd,YZa),(Cm,Rd,YZb),(Cm,Rd,YZc), (Cm,Rd,YZd),(Cm,Rd,YZe), (Cm,Rd,YZf),(Cm,Rd,YZg), (Cm,Rd,YZh),(Cm,Rd,YZi),(Cm,Rd,YZj),(Cm,Rd,YZk), (Cm, Rd,YZl),(Cm,Rd,YZm),(Cm,Rd,YZn),(Cm,Rd,YZo), (Cm,Rd,YZp),(Cm,Rd,YZq),(Cm,Rd,Y Zr),(Cm,Rd,YZs), (Cm,Rd,YZt),(Cm,Rd,YZu),(Cm,Rd,YZy),(Cm,Rd,YZw), (Cm,Rd,YZx),(C m,Rd,YZy),(Cm,Rd,YZz),(Cm,Rd,YZaa), (Cm,Rd,YZab),(Cm,Rd,YZac),(Cm,Rd,YZad),(Cm, Rd,YZae),(Cm,Rd,YZaf),(Cm,Rd,YZag),(Cm,Re,YZa), (Cm,Re,YZb),(Cm,Re,YZc),(Cm,Re, YZd),(Cm,Re,YZe), (Cm,Re,YZf),(Cm,Re,YZg),(Cm,Re, YZh),(Cm,Re,YZi), (Cm,Re,YZj),(C m,Re,YZk),(Cm,Re,YZl),(Cm,Re,YZm), (Cm,Re,YZn),(Cm,Re,YZo),(Cm,Re,YZp),(Cm,Re, YZq), (Cm,Re,YZr),(Cm,Re,YZs),(Cm,Re,YZt),(Cm,Re,YZu), (Cm,Re,YZy),(Cm,Re,YZw), (Cm,Re,YZx),(Cm,Re,YZy), (Cm,Re,YZz),(Cm,Re,YZaa),(Cm,Re,YZab),(Cm,Re, YZac),(Cm, Re,YZad),(Cm,Re,YZae),(Cm,Re,YZaf),(Cm, Re,YZag),(Cn,Ra,YZa),(Cn,Ra,YZb),(Cn,Ra, YZc),(Cn,Ra, YZd),(Cn,Ra,YZe),(Cn,Ra,YZf),(Cn,Ra,YZg),(Cn,Ra, YZh),(Cn,Ra,YZi),(Cn,R a,YZj),(Cn,Ra,YZk),(Cn,Ra, YZl),(Cn,Ra,YZm),(Cn,Ra,YZn),(Cn,Ra,YZo),(Cn,Ra, YZp),(Cn, Ra,YZq),(Cn,Ra,YZr),(Cn,Ra,YZs),(Cn,Ra, YZt),(Cn,Ra,YZu),(Cn,Ra,YZy),(Cn,Ra,YZw), (Cn,Ra, YZx),(Cn,Ra,YZy),(Cn,Ra,YZz),(Cn,Ra,YZaa),(Cn,Ra, YZab),(Cn,Ra,YZac),(Cn,Ra, YZad),(Cn,Ra,YZae),(Cn,Ra, YZaf),(Cn,Ra,YZag),(Cn,Rb,YZa),(Cn,Rb,YZb),(Cn,Rb, YZc), (Cn,Rb,YZd),(Cn,Rb,YZe),(Cn,Rb,YZf),(Cn,Rb, YZg),(Cn,Rb,YZh),(Cn,Rb,YZi),(Cn,Rb,YZj), (Cn,Rb, YZk),(Cn,Rb,YZl),(Cn,Rb,YZm),(Cn,Rb,YZn),(Cn,Rb, YZo),(Cn,Rb,YZp),(Cn,Rb, YZq),(Cn,Rb,YZr),(Cn,Rb, YZs),(Cn,Rb,YZt),(Cn,Rb,YZu),(Cn,Rb,YZy),(Cn,Rb, YZw),(Cn, Rb,YZx),(Cn,Rb,YZy),(Cn,Rb,YZz),(Cn,Rb,

YZaa),(Cn,Rb,YZab),(Cn,Rb,YZac),(Cn,Rb,YZad),(Cn,Rb,YZae),(Cn,Rb,YZaf),(Cn,Rb,YZag),(Cn,Rc,YZa),(Cn,Rc,YZb),(Cn,Rc,YZc),(Cn,Rc,YZd),(Cn,Rc,YZe),(Cn,Rc,YZf),(Cn,Rc,YZg),(Cn,Rc,YZh),(Cn,Rc,YZi),(Cn,Rc,YZj),(Cn,Rc,YZk),(Cn,Rc,YZl),(Cn,Rc,YZm),(Cn,Rc,YZn),(Cn,Rc,YZo),(Cn,Rc,YZp),(Cn,Rc,YZq),(Cn,Rc,YZr),(Cn,Rc,YZs),(Cn,Rc,YZt),(Cn,Rc,YZu),(Cn,Rc,YZv),(Cn,Rc,YZw),(Cn,Rc,YZx),(Cn,Rc,YZy),(Cn,Rc,YZz),(Cn,Rc,YZaa),(Cn,Rc,YZab),(Cn,Rc,YZac),(Cn,Rc,YZad),(Cn,Rc,YZae),(Cn,Rc,YZaf),(Cn,Rc,YZag),(Cn,Rd,YZa),(Cn,Rd,YZb),(Cn,Rd,YZc),(Cn,Rd,YZd),(Cn,Rd,YZe),(Cn,Rd,YZf),(Cn,Rd,YZg),(Cn,Rd,YZh),(Cn,Rd,YZi),(Cn,Rd,YZj),(Cn,Rd,YZk),(Cn,Rd,YZl),(Cn,Rd,YZm),(Cn,Rd,YZn),(Cn,Rd,YZo),(Cn,Rd,YZp),(Cn,Rd,YZq),(Cn,Rd,YZr),(Cn,Rd,YZs),(Cn,Rd,YZt),(Cn,Rd,YZu),(Cn,Rd,YZy),(Cn,Rd,YZw),(Cn,Rd,YZx),(Cn,Rd,YZy),(Cn,Rd,YZz),(Cn,Rd,YZaa),(Cn,Rd,YZab),(Cn,Rd,YZac),(Cn,Rd,YZad),(Cn,Rd,YZae),(Cn,Rd,YZaf),(Cn,Rd,YZag),(Cn,Re,YZa),(Cn,Re,YZb),(Cn,Re,YZc),(Cn,Re,YZd),(Cn,Re,YZe),(Cn,Re,YZf),(Cn,Re,YZg),(Cn,Re,YZh),(Cn,Re,YZi),(Cn,Re,YZj),(Cn,Re,YZk),(Cn,Re,YZl),(Cn,Re,YZm),(Cn,Re,YZn),(Cn,Re,YZo),(Cn,Re,YZp),(Cn,Re,YZq),(Cn,Re,YZr),(Cn,Re,YZs),(Cn,Re,YZt),(Cn,Re,YZu),(Cn,Re,YZy),(Cn,Re,YZw),(Cn,Re,YZx),(Cn,Re,YZy),(Cn,Re,YZz),(Cn,Re,YZaa),(Cn,Re,YZab),(Cn,Re,YZac),(Cn,Re,YZad),(Cn,Re,YZae),(Cn,Re,YZaf),(Cn,Re,YZag),(Co,Ra,YZa),(Co,Ra,YZb),(Co,Ra,YZc),(Co,Ra,YZd),(Co,Ra,YZe),(Co,Ra,YZf),(Co,Ra,YZg),(Co,Ra,YZh),(Co,Ra,YZi),(Co,Ra,YZj),(Co,Ra,YZk),(Co,Ra,YZl),(Co,Ra,YZm),(Co,Ra,YZn),(Co,Ra,YZo),(Co,Ra,YZp),(Co,Ra,YZq),(Co,Ra,YZr),(Co,Ra,YZs),(Co,Ra,YZt),(Co,Ra,YZu),(Co,Ra,YZy),(Co,Ra,YZw),(Co,Ra,YZx),(Co,Ra,YZy),(Co,Ra,YZz),(Co,Ra,YZaa),(Co,Ra,YZab),(Co,Ra,YZac),(Co,Ra,YZad),(Co,Ra,YZae),(Co,Ra,YZaf),(Co,Ra,YZag),(Co,Rb,YZa),(Co,Rb,YZb),(Co,Rb,YZc),(Co,Rb,YZd),(Co,Rb,YZe),(Co,Rb,YZf),(Co,Rb,YZg),(Co,Rb,YZh),(Co,Rb,YZi),(Co,Rb,YZj),(Co,Rb,YZk),(Co,Rb,YZl),(Co,Rb,YZm),(Co,Rb,YZn),(Co,Rb,YZo),(Co,Rb,YZp),(Co,Rb,YZq),(Co,Rb,YZr),(Co,Rb,YZs),(Co,Rb,YZt),(Co,Rb,YZu),(Co,Rb,YZy),(Co,Rb,YZw),(Co,Rb,YZx),(Co,Rb,YZy),(Co,Rb,YZz),(Co,Rb,YZaa),(Co,Rb,YZab),(Co,Rb,YZac),(Co,Rb,YZad),(Co,Rb,YZae),(Co,Rb,YZaf),(Co,Rb,YZag),(Co,Rc,YZa),(Co,Rc,YZb),(Co,Rc,YZc),(Co,Rc,YZd),(Co,Rc,YZe),(Co,Rc,YZf),(Co,Rc,YZg),(Co,Rc,YZh),(Co,Rc,YZi),(Co,Rc,YZj),(Co,Rc,YZk),(Co,Rc,YZl),(Co,Rc,YZm),(Co,Rc,YZn),(Co,Rc,YZo),(Co,Rc,YZp),(Co,Rc,YZq),(Co,Rc,YZr),(Co,Rc,YZs),(Co,Rc,YZt),(Co,Rc,YZu),(Co,Rc,YZv),(Co,Rc,YZw),(Co,Rc,YZx),(Co,Rc,YZy),(Co,Rc,YZz),(Co,Rc,YZaa),(Co,Rc,YZab),(Co,Rc,YZac),(Co,Rc,YZad),(Co,Rc,YZae),(Co,Rc,YZaf),(Co,Rc,YZag),(Co,Rd,YZa),(Co,Rd,YZb),(Co,Rd,YZc),(Co,Rd,YZd),(Co,Rd,YZe),(Co,Rd,YZf),(Co,Rd,YZg),(Co,Rd,YZh),(Co,Rd,YZi),(Co,Rd,YZj),(Co,Rd,YZk),(Co,Rd,YZl),(Co,Rd,YZm),(Co,Rd,YZn),(Co,Rd,YZo),(Co,Rd,YZp),(Co,Rd,YZq),(Co,Rd,YZr),(Co,Rd,YZs),(Co,Rd,YZt),(Co,Rd,YZu),(Co,Rd,YZy),(Co,Rd,YZw),(Co,Rd,YZx),(Co,Rd,YZy),(Co,Rd,YZz),(Co,Rd,YZaa),(Co,Rd,YZab),(Co,Rd,YZac),(Co,Rd,YZad),(Co,Rd,YZae),(Co,Rd,YZaf),(Co,Rd,YZag),(Co,Re,YZa),(Co,Re,YZb),(Co,Re,YZc),(Co,Re,YZd),(Co,Re,YZe),(Co,Re,YZf),(Co,Re,YZg),(Co,Re,YZh),(Co,Re,YZi),(Co,Re,YZj),(Co,Re,YZk),(Co,Re,YZl),(Co,Re,YZm),(Co,Re,YZn),(Co,Re,YZo),(Co,Re,YZp),(Co,Re,YZq),(Co,Re,YZr),(Co,Re,YZs),(Co,Re,YZt),(Co,Re,YZu),(Co,Re,YZy),(Co,Re,YZw),(Co,Re,YZx),(Co,Re,YZy),(Co,Re,YZz),(Co,Re,YZaa),(Co,Re,YZab),(Co,Re,YZac),(Co,Re,YZad),(Co,Re,YZae),(Co,Re,YZaf),(Co,Re,YZag),(Cp,Ra,YZa),(Cp,Ra,YZb),(Cp,Ra,YZc),(Cp,Ra,YZd),(Cp,Ra,YZe),(Cp,Ra,YZf),(Cp,Ra,YZg),(Cp,Ra,YZh),(Cp,Ra,YZi),(Cp,Ra,YZj),(Cp,Ra,YZk),(Cp,Ra,YZl),(Cp,Ra,YZm),(Cp,Ra,YZn),(Cp,Ra,YZo),(Cp,Ra,YZp),(Cp,Ra,YZq),(Cp,Ra,YZr),(Cp,Ra,YZs),(Cp,Ra,YZt),(Cp,Ra,YZu),(Cp,Ra,YZy),(Cp,Ra,YZw),(Cp,Ra,YZx),(Cp,Ra,YZy),(Cp,Ra,YZz),(Cp,Ra,YZaa),(Cp,Ra,YZab),(Cp,Ra,YZac),(Cp,Ra,YZad),(Cp,Ra,YZae),(Cp,Ra,YZaf),(Cp,Ra,YZag),(Cp,Rb,YZa),(Cp,Rb,YZb),(Cp,Rb,YZc),(Cp,Rb,Yal),(Cp,Rb,YZe),(Cp,Rb,YZf),(Cp,Rb,YZg),(Cp,Rb,YZh),(Cp,Rb,YZi),(Cp,Rb,YZj),(Cp,Rb,YZk),(Cp,Rb,YZl),(Cp,Rb,YZm),(Cp,Rb,YZn),(Cp,Rb,YZo),(Cp,Rb,YZp),(Cp,Rb,YZq),(Cp,Rb,YZr),(Cp,Rb,YZs),(Cp,Rb,YZt),(Cp,Rb,YZu),(Cp,Rb,YZy),(Cp,Rb,YZw),(Cp,Rb,YZx),(Cp,Rb,YZy),(Cp,Rb,YZz),(Cp,Rb,YZaa),(Cp,Rb,YZab),(Cp,Rb,YZac),(Cp,Rb,YZad),(Cp,Rb,YZae),(Cp,Rb,YZaf),(Cp,Rb,YZag),(Cp,Rc,YZa),(Cp,Rc,YZb),(Cp,Rc,YZc),(Cp,Rc,YZd),(Cp,Rc,YZe),(Cp,Rc,YZf),(Cp,Rc,YZg),(Cp,Rc,YZh),(Cp,Rc,YZi),(Cp,Rc,YZj),(Cp,Rc,YZk),(Cp,Rc,YZl),(Cp,Rc,YZm),(Cp,Rc,YZn),(Cp,Rc,YZo),(Cp,Rc,YZp),(Cp,Rc,YZq),(Cp,Rc,YZr),(Cp,Rc,YZs),(Cp,Rc,YZt),(Cp,Rc,YZu),(Cp,Rc,YZy),(Cp,Rc,YZw),(Cp,Rc,YZx),(Cp,Rc,YZy),(Cp,Rc,YZz),(Cp,Rc,YZaa),(Cp,Rc,YZab),(Cp,Rc,YZac),(Cp,Rc,YZad),(Cp,Rc,YZae),(Cp,Rc,YZaf),(Cp,Rc,YZag),(Cp,Rd,YZa),(Cp,Rd,YZb),(Cp,Rd,YZc),(Cp,Rd,YZd),(Cp,Rd,YZe),(Cp,Rd,YZf),(Cp,Rd,YZg),(Cp,Rd,YZh),(Cp,Rd,YZi),(Cp,Rd,YZj),(Cp,Rd,YZk),(Cp,Rd,YZl),(Cp,Rd,YZm),(Cp,Rd,YZn),(Cp,Rd,YZo),(Cp,Rd,YZp),(Cp,Rd,YZq),(Cp,Rd,YZr),(Cp,Rd,YZs),(Cp,Rd,YZt),(Cp,Rd,YZu),(Cp,Rd,YZy),(Cp,Rd,YZw),(Cp,Rd,YZx),(Cp,Rd,YZy),(Cp,Rd,YZz),(Cp,Rd,YZaa),(Cp,Rd,YZab),(Cp,Rd,YZac),(Cp,Rd,YZad),(Cp,Rd,YZae),(Cp,Rd,YZaf),(Cp,Rd,YZag),(Cp,Re,YZa),(Cp,Re,YZb),(Cp,Re,YZc),(Cp,Re,YZd),(Cp,Re,YZe),(Cp,Re,YZf),(Cp,Re,YZg),(Cp,Re,YZh),(Cp,Re,YZi),(Cp,Re,YZj),(Cp,Re,YZk),(Cp,Re,YZl),(Cp,Re,YZm),(Cp,Re,YZn),(Cp,Re,YZo),(Cp,Re,YZp),(Cp,Re,YZq),(Cp,Re,YZr),(Cp,Re,YZs),(Cp,Re,YZt),(Cp,Re,YZu),(Cp,Re,YZv),(Cp,Re,YZw),(Cp,Re,YZx),(Cp,Re,YZy),(Cp,Re,YZz),(Cp,Re,YZaa),(Cp,Re,YZab),(Cp,Re,YZac),(Cp,Re,YZad),(Cp,Re,YZae),(Cp,Re,YZaf),(Cp,Re,YZag),(Cq,Ra,YZa),(Cq,Ra,YZb),(Cq,Ra,YZc),(Cq,Ra,YZd),(Cq,Ra,YZe),(Cq,Ra,YZf),(Cq,Ra,YZg),(Cq,Ra,YZh),(Cq,Ra,YZi),(Cq,Ra,YZj),(Cq,Ra,YZk),(Cq,Ra,YZl),(Cq,Ra,YZm),(Cq,Ra,YZn),(Cq,Ra,YZo),(Cq,Ra,YZp),(Cq,Ra,YZq),(Cq,Ra,YZr),(Cq,Ra,YZs),(Cq,Ra,YZt),(Cq,Ra,YZu),(Cq,Ra,YZv),(Cq,Ra,YZw),(Cq,Ra,YZx),(Cq,Ra,YZy),(Cq,Ra,YZz),(Cq,Ra,YZaa),(Cq,Ra,YZab),(Cq,Ra,YZac),(Cq,Ra,YZad),(Cq,Ra,YZae),(Cq,Ra,YZaf),(Cq,Ra,YZag),(Cq,Rb,YZa),(Cq,Rb,YZb),(Cq,Rb,YZc),(Cq,Rb,YZd),(Cq,Rb,YZe),(Cq,Rb,YZf),(Cq,Rb,YZg),(Cq,Rb,YZh),(Cq,Rb,YZi),(Cq,Rb,YZj),(Cq,Rb,Ya),(Cq,Rb,YZl),(Cq,Rb,YZm),(Cq,Rb,YZn),(Cq,Rb,YZo),(Cq,Rb,YZp),(Cq,Rb,YZq),(Cq,Rb,YZr),(Cq,Rb,YZs),(Cq,Rb,YZt),(Cq,Rb,YZu),(Cq,Rb,YZv),(Cq,Rb,YZw),(Cq,Rb,YZx),(Cq,Rb,YZy),(Cq,Rb,YZz),(Cq,Rb,YZaa),(Cq,Rb,YZab),(Cq,Rb,YZac),(Cq,Rb,YZad),(Cq,Rb,YZae),(Cq,Rb,YZaf),(Cq,Rb,YZag),(Cq,Rc,YZa),(Cq,Rc,YZb),(Cq,Rc,YZc),(Cq,Rc,YZd),(Cq,Rc,YZe),(Cq,Rc,YZf),(Cq,Rc,YZg),(Cq,Rc,YZh),(Cq,Rc,YZi),(Cq,Rc,YZj),(Cq,Rc,YZk),(Cq,Rc,YZl),(Cq,Rc,YZm),(Cq,Rc,YZn),(Cq,Rc,YZo),(Cq,Rc,YZp),(Cq,Rc,YZq),(Cq,Rc,YZr),(Cq,Rc,YZs),(Cq,Rc,YZt),(Cq,Rc,YZu),(Cq,Rc,YZv),(Cq,Rc,YZw),(Cq,Rc,YZx),(Cq,Rc,YZy),(Cq,Rc,YZz),(Cq,Rc,YZaa),(Cq,Rc,YZab),(Cq,Rc,YZac),(Cq,Rc,YZad),(Cq,Rc,YZae),(Cq,Rc,YZaf),(Cq,Rc,YZag),(Cq,Rd,YZa),(Cq,Rd,YZb),(Cq,Rd,YZc),(Cq,Rd,

YZd),(Cq,Rd,YZe),(Cq,Rd,YZf),(Cq,Rd,YZg),(Cq,Rd,YZh),(Cq,Rd,YZi),(Cq,Rd,YZj),(Cq,Rd,YZk),(Cq,Rd,YZl),(Cq,Rd,YZm),(Cq,Rd,YZn),(Cq,Rd,YZo),(Cq,Rd,YZp),(Cq,Rd,YZq),(Cq,Rd,YZr),(Cq,Rd,YZs),(Cq,Rd,YZt),(Cq,Rd,YZu),(Cq,Rd,YZv),(Cq,Rd,YZw),(Cq,Rd,YZx),(Cq,Rd,YZy),(Cq,Rd,YZz),(Cq,Rd,YZaa),(Cq,Rd,YZab),(Cq,Rd,YZac),(Cq,Rd,YZad),(Cq,Rd,YZae),(Cq,Rd,YZaf),(Cq,Rd,YZag),(Cq,Re,YZa),(Cq,Re,YZb), (Cq,Re,YZc),(Cq,Re,YZd),(Cq,Re,YZe),(Cq,Re,YZf),(Cq,Re,YZg),(Cq,Re,YZh),(Cq,Re,YZi), (Cq,Re,YZj),(Cq,Re,YZk),(Cq,Re,YZl),(Cq,Re,YZm),(Cq,Re,YZn),(Cq,Re,YZo),(Cq,Re,YZp),(Cq,Re,YZq),(Cq,Re,YZr),(Cq,Re,YZs),(Cq,Re,YZt),(Cq,Re,YZu),(Cq,Re,YZv),(Cq,Re,YZw),(Cq,Re,YZx),(Cq,Re,YZy),(Cq,Re,YZz),(Cq,Re,YZaa),(Cq,Re,YZab),(Cq,Re,YZac), (Cq,Re,YZad),(Cq,Re,YZae),(Cq,Re,YZaf),(Cq,Re,YZag),(Cr,Ra,YZa),(Cr,Ra,YZb),(Cr,Ra, YZc),(Cr,Ra,YZd),(Cr,Ra,YZe),(Cr,Ra,YZf),(Cr,Ra,YZg),(Cr,Ra,YZh),(Cr,Ra,YZi),(Cr,Ra, YZj),(Cr,Ra,Ya),(Cr,Ra,YZl),(Cr,Ra,YZm),(Cr,Ra,YZn),(Cr,Ra,YZo),(Cr,Ra,YZp),(Cr,Ra, YZq),(Cr,Ra,YZr),(Cr,Ra,YZs),(Cr,Ra,YZt),(Cr,Ra,YZu),(Cr,Ra,YZv),(Cr,Ra,YZw),(Cr,Ra, YZx),(Cr,Ra,YZy),(Cr,Ra,YZz),(Cr,Ra,YZaa),(Cr,Ra,YZab),(Cr,Ra,YZac),(Cr,Ra,YZad),(Cr, Ra,YZae),(Cr,Ra,YZaf),(Cr,Ra,YZag),(Cr,Rb,YZa),(Cr,Rb,YZb),(Cr,Rb,YZc),(Cr,Rb,YZd), (Cr,Rb,YZe),(Cr,Rb,YZf),(Cr,Rb,YZg),(Cr,Rb,YZh),(Cr,Rb,YZi),(Cr,Rb,YZj),(Cr,Rb,YZk), (Cr,Rb,YZl),(Cr,Rb,YZm),(Cr,Rb,YZn),(Cr,Rb,YZo),(Cr,Rb,YZp),(Cr,Rb,YZq),(Cr,Rb,YZr), (Cr,Rb,YZs),(Cr,Rb,YZt),(Cr,Rb,YZu),(Cr,Rb,YZy),(Cr,Rb,YZw),(Cr,Rb,YZx),(Cr,Rb,YZy), (Cr,Rb,YZz),(Cr,Rb,YZaa),(Cr,Rb,YZab),(Cr,Rb,YZac),(Cr,Rb,YZad),(Cr,Rb,YZae),(Cr,Rb, YZaf),(Cr,Rb,YZag),(Cr,Rc,YZa),(Cr,Rc,YZb),(Cr,Rc,YZc),(Cr,Rc,YZd),(Cr,Rc,YZe),(Cr, Rc,YZf),(Cr,Rc,YZg),(Cr,Rc,YZh),(Cr,Rc,YZi),(Cr,Rc,YZj),(Cr,Rc,YZk),(Cr,Rc,YZl),(Cr,Rc,YZm),(Cr,Rc,YZn),(Cr,Rc,YZo),(Cr,Rc,YZp),(Cr,Rc,YZq),(Cr,Rc,YZr),(Cr,Rc,YZs),(Cr,Rc,YZt),(Cr,Rc,YZu),(Cr,Rc,YZy),(Cr,Rc,YZw),(Cr,Rc,YZx),(Cr,Rc,YZy),(Cr,Rc,YZz),(Cr,Rc,YZaa),(Cr,Rc,YZab),(Cr,Rc,YZac),(Cr,Rc,YZad),(Cr,Rc,YZae),(Cr,Rc,YZaf),(Cr,Rc,YZag), (Cr,Rd,YZa),(Cr,Rd,YZb),(Cr,Rd,YZc),(Cr,Rd,YZd),(Cr,Rd,YZe),(Cr,Rd,YZf),(Cr,Rd,YZg), (Cr,Rd,YZh),(Cr,Rd,YZi),(Cr,Rd,YZj),(Cr,Rd,YZk),(Cr,Rd,YZl),(Cr,Rd,YZm),(Cr,Rd,YZn), (Cr,Rd,YZo),(Cr,Rd,YZp),(Cr,Rd,YZq),(Cr,Rd,YZr),(Cr,Rd,YZs),(Cr,Rd,YZt),(Cr,Rd,YZu), (Cr,Rd,YZy),(Cr,Rd,YZw),(Cr,Rd,YZx),(Cr,Rd,YZy),(Cr,Rd,YZz),(Cr,Rd,YZaa),(Cr,Rd,YZab),(Cr,Rd,YZac),(Cr,Rd,YZad),(Cr,Rd,YZae),(Cr,Rd,YZaf),(Cr,Rd,YZag),(Cr,Re,YZa),(Cr,Re,YZb),(Cr,Re,YZc),(Cr,Re,YZd),(Cr,Re,YZe),(Cr,Re,YZf),(Cr,Re,YZg),(Cr,Re,YZh),(Cr,Re,YZi),(Cr,Re,YZj),(Cr,Re,YZk),(Cr,Re,YZl),(Cr,Re,YZm),(Cr,Re,YZn),(Cr,Re,YZo),(Cr,Re,YZp),(Cr,Re,YZq),(Cr,Re,YZr),(Cr,Re,YZs),(Cr,Re,YZt),(Cr,Re,YZu),(Cr,Re,YZy),(Cr,Re,YZw),(Cr,Re,YZx),(Cr,Re,YZy),(Cr,Re,YZz),(Cr,Re,YZaa),(Cr,Re,YZab),(Cr,Re,YZac), (Cr,Re,YZad),(Cr,Re,YZae),(Cr,Re,YZaf),(Cr,Re,YZag),(Cs,Ra,YZa),(Cs,Ra,YZb),(Cs,Ra,YZc),(Cs,Ra,YZd),(Cs,Ra,YZe),(Cs,Ra,YZf),(Cs,Ra,YZg),(Cs,Ra,Ya),(Cs,Ra,YZi),(Cs,Ra,YZj),(Cs,Ra,YZk),(Cs,Ra,YZl),(Cs,Ra,YZm),(Cs,Ra,YZn),(Cs,Ra,YZo),(Cs,Ra,YZp),(Cs,Ra,YZq),(Cs,Ra,YZr),(Cs,Ra,YZs),(Cs,Ra,YZt),(Cs,Ra,YZu),(Cs,Ra,YZy),(Cs,Ra,YZw),(Cs,Ra,YZx),(Cs,Ra,YZy),(Cs,Ra,YZz),(Cs,Ra,YZaa),(Cs,Ra,YZab),(Cs,Ra,YZac),(Cs,Ra,YZad), (Cs,Ra,YZae),(Cs,Ra,YZaf),(Cs,Ra,YZag),(Cs,Rb,YZa),(Cs,Rb,YZb),(Cs,Rb,YZc),(Cs,Rb,YZd),(Cs,Rb,YZe),(Cs,Rb,YZf),(Cs,Rb,YZg),(Cs,Rb,YZh),(Cs,Rb,YZi),(Cs,Rb,YZj),(Cs,Rb,YZk),(Cs,Rb,YZl),(Cs,Rb,YZm),(Cs,Rb,YZn),(Cs,Rb,YZo),(Cs,Rb,YZp),(Cs,Rb,YZq),(Cs,Rb,YZr),(Cs,Rb,YZs),(Cs,Rb,YZt),(Cs,Rb,YZu),(Cs,Rb,YZy),(Cs,Rb,YZw),(Cs,Rb,YZx),(Cs,Rb,YZy),(Cs,Rb,YZz),(Cs,Rb,YZaa),(Cs,Rb,YZab),(Cs,Rb,YZac),(Cs,Rb,YZad),(Cs,Rb,YZae),(Cs,Rb,YZaf),(Cs,Rb,YZag),(Cs,Rc,YZa),(Cs,Rc,YZb),(Cs,Rc,YZc),(Cs,Rc,YZd),(Cs,Rc,YZe),(Cs,Rc,YZf),(Cs,Rc,YZg),(Cs,Rc,Ya),(Cs,Rc,YZi),(Cs,Rc,YZj),(Cs,Rc,YZk),(Cs,Rc,YZl),(Cs,Rc,YZm),(Cs,Rc,YZn),(Cs,Rc,YZo),(Cs,Rc,YZp),(Cs,Rc,YZq),(Cs,Rc,YZr),(Cs,Rc,YZs),(Cs,Rc,YZt),(Cs,Rc,YZu),(Cs,Rc,YZy),(Cs,Rc,YZw),(Cs,Rc,YZx),(Cs,Rc,YZy),(Cs,Rc,YZz),(Cs,Rc,YZaa),(Cs,Rc,YZab),(Cs,Rc,YZac),(Cs,Rc,YZad),(Cs,Rc,YZae),(Cs,Rc,YZaf), (Cs,Rc,YZag),(Cs,Rd,YZa),(Cs,Rd,YZb),(Cs,Rd,YZc),(Cs,Rd,YZd),(Cs,Rd,YZe),(Cs,Rd,YZf),(Cs,Rd,YZg),(Cs,Rd,YZh),(Cs,Rd,YZi),(Cs,Rd,YZj),(Cs,Rd,YZk),(Cs,Rd,YZl),(Cs,Rd,YZm),(Cs,Rd,YZn),(Cs,Rd,YZo),(Cs,Rd,YZp),(Cs,Rd,YZq),(Cs,Rd,YZr),(Cs,Rd,YZs),(Cs,Rd,YZt),(Cs,Rd,YZu),(Cs,Rd,YZy),(Cs,Rd,YZw),(Cs,Rd,YZx),(Cs,Rd,YZy),(Cs,Rd,YZz),(Cs,Rd,YZaa),(Cs,Rd,YZab),(Cs,Rd,YZac),(Cs,Rd,YZad),(Cs,Rd,YZae),(Cs,Rd,YZaf),(Cs,Rd,YZag),(Cs,Re,YZa),(Cs,Re,YZb),(Cs,Re,YZc),(Cs,Re,YZd),(Cs,Re,YZe),(Cs,Re,YZf),(Cs,Re,YZg),(Cs,Re,YZh),(Cs,Re,YZi),(Cs,Re,YZj),(Cs,Re,YZk),(Cs,Re,YZl),(Cs,Re,YZm),(Cs,Re,YZn),(Cs,Re,YZo),(Cs,Re,YZp),(Cs,Re,YZq),(Cs,Re,YZr),(Cs,Re,YZs),(Cs,Re,YZt),(Cs,Re,YZu),(Cs,Re,YZy),(Cs,Re,YZw),(Cs,Re,YZx),(Cs,Re,YZy),(Cs,Re,YZz),(Cs,Re,YZaa),(Cs,Re,YZab),(Cs,Re,YZac),(Cs,Re,YZad),(Cs,Re,YZae),(Cs,Re,YZaf),(Cs,Re,YZag),(Ct,Ra,YZa),(Ct,Ra,YZb),(Ct,Ra,YZc),(Ct,Ra,YZd),(Ct,Ra,YZe),(Ct,Ra,YZf),(Ct,Ra,YZg),(Ct,Ra,YZh),(Ct,Ra,YZi),(Ct,Ra,YZj),(Ct,Ra,YZk),(Ct,Ra,YZl),(Ct,Ra,YZm),(Ct,Ra,YZn),(Ct,Ra,YZo),(Ct,Ra,YZp),(Ct,Ra,YZq),(Ct,Ra,YZr),(Ct,Ra,YZs),(Ct,Ra,YZt),(Ct,Ra,YZu),(Ct,Ra,YZy),(Ct,Ra,YZw),(Ct,Ra,YZx),(Ct,Ra,YZy),(Ct,Ra,YZz),(Ct,Ra,YZaa),(Ct,Ra,YZab),(Ct,Ra,YZac),(Ct,Ra,YZad),(Ct,Ra,YZae),(Ct,Ra,YZaf),(Ct,Ra,YZag),(Ct,Rb,YZa),(Ct,Rb,YZb),(Ct,Rb,YZc),(Ct,Rb,YZd),(Ct,Rb,YZe),(Ct,Rb,YZf),(Ct,Rb,YZg),(Ct,Rb,Yh),(Ct,Rb,YZi),(Ct,Rb,YZj), (Ct,Rb,YZk),(Ct,Rb,YZl),(Ct,Rb,YZm),(Ct,Rb,YZn),(Ct,Rb,YZo),(Ct,Rb,YZp),(Ct,Rb,YZq), (Ct,Rb,YZr),(Ct,Rb,YZs),(Ct,Rb,YZt),(Ct,Rb,YZu),(Ct,Rb,YZy),(Ct,Rb,YZw),(Ct,Rb,YZx), (Ct,Rb,YZy),(Ct,Rb,YZz),(Ct,Rb,YZaa),(Ct,Rb,YZab),(Ct,Rb,YZac),(Ct,Rb,YZad),(Ct,Rb,YZae),(Ct,Rb,YZaf),(Ct,Rb,YZag),(Ct,Rc,YZa),(Ct,Rc,YZb),(Ct,Rc,YZc),(Ct,Rc,YZd),(Ct,Rc,YZe),(Ct,Rc,YZf),(Ct,Rc,YZg),(Ct,Rc,YZh),(Ct,Rc,YZi),(Ct,Rc,YZj),(Ct,Rc,YZk),(Ct,Rc,YZl),(Ct,Rc,YZm),(Ct,Rc,YZn),(Ct,Rc,YZo),(Ct,Rc,YZp),(Ct,Rc,YZq),(Ct,Rc,YZr),(Ct,Rc,YZs),(Ct,Rc,YZt),(Ct,Rc,YZu),(Ct,Rc,YZy),(Ct,Rc,YZw),(Ct,Rc,YZx),(Ct,Rc,YZy),(Ct,Rc,YZz),(Ct,Rc,YZaa),(Ct,Rc,YZab),(Ct,Rc,YZac),(Ct,Rc,YZad),(Ct,Rc,YZae),(Ct,Rc,YZaf),(Ct,Rc,YZag),(Ct,Rd,YZa),(Ct,Rd,YZb),(Ct,Rd,YZc),(Ct,Rd,YZd),(Ct,Rd,YZe),(Ct,Rd,YZf),(Ct,Rd,YZg),(Ct,Rd,YZh),(Ct,Rd,YZi),(Ct,Rd,YZj),(Ct,Rd,YZk),(Ct,Rd,YZl),(Ct,Rd,YZm),(Ct,Rd,YZn),(Ct,Rd,YZo),(Ct,Rd,YZp),(Ct,Rd,YZq),(Ct,Rd,YZr),(Ct,Rd,YZs),(Ct,Rd,YZt),(Ct,Rd,YZu),(Ct,Rd,YZy),(Ct,Rd,YZw),(Ct,Rd,YZx),(Ct,Rd,YZy),(Ct,Rd,YZz),(Ct,Rd,YZaa),(Ct,Rd,YZab),(Ct,Rd,YZac),(Ct,Rd,YZad),(Ct,Rd,YZae),(Ct,Rd,YZaf),(Ct,Rd,YZag),(Ct,Re,YZa),(Ct,Re,YZb),(Ct,Re,YZc),(Ct,Re,YZd),(Ct,Re,YZe),(Ct,Re,Ya),(Ct,Re,YZg),(Ct,Re,YZh),(Ct,Re,YZi),(Ct,Re,YZj),(Ct,Re,YZl),(Ct,Re,YZl),(Ct,Re,YZm),(Ct,Re,YZn),(Ct,Re,YZo),(Ct,Re,YZp),(Ct,Re,YZq),(Ct,Re,YZr),(Ct,Re,YZs),(Ct,Re,YZt),(Ct,Re,YZu),(Ct,Re,YZy),(Ct,Re,YZw),(Ct,Re,YZx),(Ct,Re,YZy),(Ct,Re,YZz),(Ct,Re,YZaa),(Ct,Re,YZab),(Ct,Re,YZac),(Ct,Re,YZad),(Ct,Re,YZae),(Ct,Re,YZaf),(Ct,Re,YZag),(Cu,Ra,YZa),(Cu,Ra,YZb),(Cu,Ra,YZc),(Cu,Ra,YZd),(Cu,Ra,YZe),(Cu,Ra,YZf),(Cu,Ra,YZg),(Cu,Ra,

YZl),(Cu,Ra,YZi),(Cu,Ra,YZj),(Cu,Ra,YZk),(Cu,Ra,YZl),(Cu,Ra,YZm),(Cu,Ra,YZn),(Cu,Ra,YZo),(Cu,Ra,YZp),(Cu,Ra,YZq),(Cu,Ra,YZr),(Cu,Ra,YZs),(Cu,Ra,YZt),(Cu,Ra,YZu),(Cu,Ra,YZv),(Cu,Ra,YZw),(Cu,Ra,YZx),(Cu,Ra,YZy),(Cu,Ra,YZz),(Cu,Ra,YZaa),(Cu,Ra,YZab),(Cu,Ra,YZac),(Cu,Ra,YZad),(Cu,Ra,YZae),(Cu,Ra,YZaf),(Cu,Ra,YZag),(Cu,Rb,YZa),(Cu,Rb,YZb),(Cu,Rb,YZc),(Cu,Rb,YZd),(Cu,Rb,YZe),(Cu,Rb,YZf),(Cu,Rb,YZg),(Cu,Rb,YZh),(Cu,Rb,YZi),(Cu,Rb,YZj),(Cu,Rb,YZk),(Cu,Rb,YZl),(Cu,Rb,YZm),(Cu,Rb,YZn),(Cu,Rb,YZo),(Cu,Rb,YZp),(Cu,Rb,YZq),(Cu,Rb,YZr),(Cu,Rb,YZs),(Cu,Rb,YZt),(Cu,Rb,YZu),(Cu,Rb,YZv),(Cu,Rb,YZw),(Cu,Rb,YZx),(Cu,Rb,YZy),(Cu,Rb,YZz),(Cu,Rb,YZaa),(Cu,Rb,YZab),(Cu,Rb,YZac),(Cu,Rb,YZad),(Cu,Rb,YZae),(Cu,Rb,YZaf),(Cu,Rb,YZag),(Cu,Rc,YZa),(Cu,Rc,YZb),(Cu,Rc,YZc),(Cu,Rc,Yal),(Cu,Rc,YZe),(Cu,Rc,YZf),(Cu,Rc,YZg),(Cu,Rc,YZh),(Cu,Rc,YZi),(Cu,Rc,YZj),(Cu,Rc,YZk),(Cu,Rc,YZl),(Cu,Rc,YZm),(Cu,Rc,YZn),(Cu,Rc,YZo),(Cu,Rc,YZp),(Cu,Rc,YZq),(Cu,Rc,YZr),(Cu,Rc,YZs),(Cu,Rc,YZt),(Cu,Rc,YZu),(Cu,Rc,YZv),(Cu,Rc,YZw),(Cu,Rc,YZx)(Cu,Rc,YZy),(Cu,Rc,YZz),(Cu,Rc,YZaa),(Cu,Rc,YZab),(Cu,Rc,YZac),(Cu,Rc,YZad),(Cu,Rc,YZae),(Cu,Rc,YZaf),(Cu,Rc,YZag),(Cu,Rd,YZa),(Cu,Rd,YZb),(Cu,Rd,YZc),(Cu,Rd,YZd),(Cu,Rd,YZe),(Cu,Rd,YZf),(Cu,Rd,YZg),(Cu,Rd,YZh),(Cu,Rd,YZi),(Cu,Rd,YZj),(Cu,Rd,YZk),(Cu,Rd,YZl),(Cu,Rd,YZm),(Cu,Rd,YZn),(Cu,Rd,YZo),(Cu,Rd,YZp),(Cu,Rd,YZq),(Cu,Rd,YZr),(Cu,Rd,YZs),(Cu,Rd,YZt),(Cu,Rd,YZu),(Cu,Rd,YZv),(Cu,Rd,YZw),(Cu,Rd,YZx),(Cu,Rd,YZy),(Cu,Rd,YZz),(Cu,Rd,YZaa),(Cu,Rd,YZab),(Cu,Rd,YZac),(Cu,Rd,YZad),(Cu,Rd,YZae),(Cu,Rd,YZaf),(Cu,Rd,YZag),(Cu,Re,YZa),(Cu,Re,YZb),(Cu,Re,YZc),(Cu,Re,YZd),(Cu,Re,YZe),(Cu,Re,YZf),(Cu,Re,YZg),(Cu,Re,YZh),(Cu,Re,YZi),(Cu,Re,YZj),(Cu,Re,YZk),(Cu,Re,YZl),(Cu,Re,YZm),(Cu,Re,YZn),(Cu,Re,YZo),(Cu,Re,YZp),(Cu,Re,YZq),(Cu,Re,YZr),(Cu,Re,YZs),(Cu,Re,YZt),(Cu,Re,YZu),(Cu,Re,YZv),(Cu,Re,YZw),(Cu,Re,YZx),(Cu,Re,YZy),(Cu,Re,YZz),(Cu,Re,YZaa),(Cu,Re,YZab),(Cu,Re,YZac),(Cu,Re,YZad),(Cu,Re,YZae),(Cu,Re,YZaf),(Cu,Re,YZag),(Cv,Ra,YZa),(Cv,Ra,YZb),(Cv,Ra,YZc),(Cv,Ra,YZd),(Cv,Ra,YZe),(Cv,Ra,YZf),(Cv,Ra,YZg),(Cv,Ra,YZh),(Cv,Ra,YZi),(Cv,Ra,YZj),(Cv,Ra,YZk),(Cv,Ra,YZl),(Cv,Ra,YZm),(Cv,Ra,YZn),(Cv,Ra,YZo),(Cv,Ra,YZp),(Cv,Ra,YZq),(Cv,Ra,YZr),(Cv,Ra,YZs),(Cv,Ra,YZt),(Cv,Ra,YZu),(Cv,Ra,YZv),(Cv,Ra,YZw),(Cv,Ra,YZx),(Cv,Ra,YZy)(Cv,Ra,YZz),(Cv,Ra,YZaa),(Cv,Ra,YZab),(Cv,Ra,YZac),(Cv,Ra,YZad),(Cv,Ra,YZae),(Cv,Ra,YZaf),(Cv,Ra,YZag),(Cv,Rb,YZa),(Cv,Rb,YZb),(Cv,Rb,YZc),(Cv,Rb,YZd),(Cv,Rb,YZe)(Cv,Rb,YZf),(Cv,Rb,YZg),(Cv,Rb,YZh),(Cv,Rb,YZi),(Cv,Rb,YZj),(Cv,Rb,YZk),(Cv,Rb,YZl),(Cv,Rb,YZm),(Cv,Rb,YZn),(Cv,Rb,YZo),(Cv,Rb,YZp),(Cv,Rb,YZq),(Cv,Rb,YZr),(Cv,Rb,YZs),(Cv,Rb,YZt),(Cv,Rb,YZu),(Cv,Rb,YZv),(Cv,Rb,YZw),(Cv,Rb,YZx),(Cv,Rb,YZy),(Cv,Rb,YZz),(Cv,Rb,YZaa),(Cv,Rb,YZab),(Cv,Rb,YZac),(Cv,Rb,YZad),(Cv,Rb,YZae),(Cv,Rb,YZaf),(Cv,Rb,YZag),(Cv,Rc,YZa),(Cv,Rc,YZb),(Cv,Rc,YZc),(Cv,Rc,YZd),(Cv,Rc,YZe),(Cv,Rc,YZf),(Cv,Rc,YZg),(Cv,Rc,YZh),(Cv,Rc,YZi),(Cv,Rc,YZj),(Cv,Rc,YZk),(Cv,Rc,YZl),(Cv,Rc,YZm),(Cv,Rc,YZn),(Cv,Rc,YZo),(Cv,Rc,YZp),(Cv,Rc,YZq),(Cv,Rc,YZr),(Cv,Rc,YZs),(Cv,Rc,YZt),(Cv,Rc,YZu),(Cv,Rc,YZv),(Cv,Rc,YZw),(Cv,Rc,YZx),(Cv,Rc,YZy),(Cv,Rc,YZz),(Cv,Rc,YZaa),(Cv,Rc,YZab),(Cv,Rc,YZac),(Cv,Rc,YZad),(Cv,Rc,YZae),(Cv,Rc,YZaf),(Cv,Rc,YZag),(Cv,Rd,YZa),(Cv,Rd,YZb),(Cv,Rd,YZc),(Cv,Rd,YZd),(Cv,Rd,YZe),(Cv,Rd,YZf),(Cv,Rd,YZg),(Cv,Rd,YZh),(Cv,Rd,YZi),(Cv,Rd,YZj),(Cv,Rd,YZk),(Cv,Rd,YZl),(Cv,Rd,YZm),(Cv,Rd,YZn),(Cv,Rd,YZo),(Cv,Rd,YZp),(Cv,Rd,YZq),(Cv,Rd,YZr),(Cv,Rd,YZs),(Cv,Rd,YZt),(Cv,Rd,YZu),(Cv,Rd,YZv),(Cv,Rd,YZw),(Cv,Rd,YZx),(Cv,Rd,YZy),(Cv,Rd,YZz),(Cv,Rd,YZaa),(Cv,Rd,YZab),(Cv,Rd,YZac),(Cv,Rd,YZad),(Cv,Rd,YZae),(Cv,Rd,YZaf),(Cv,Rd,YZag),(Cv,Re,YZa),(Cv,Re,YZb),(Cv,Re,YZc),(Cv,Re,YZd),(Cv,Re,YZe),(Cv,Re,YZf),(Cv,Re,YZg),(Cv,Re,YZh),(Cv,Re,YZi),(Cv,Re,YZj),(Cv,Re,YZk),(Cv,Re,YZl),(Cv,Re,YZm),(Cv,Re,YZn),(Cv,Re,YZo),(Cv,Re,YZp),(Cv,Re,YZq),(Cv,Re,YZr),(Cv,Re,YZs),(Cv,Re,YZt),(Cv,Re,YZu),(Cv,Re,YZv),(Cv,Re,YZw),(Cv,Re,YZx),(Cv,Re,YZy),(Cv,Re,YZz),(Cv,Re,YZaa),(Cv,Re,YZab),(Cv,Re,YZac),(Cv,Re,YZad),(Cv,Re,YZae),(Cv,Re,YZaf),(Cv,Re,YZag),(Cw,Ra,YZa),(Cw,Ra,YZb),(Cw,Ra,YZc),(Cw,Ra,YZd),(Cw,Ra,YZe),(Cw,Ra,YZf),(Cw,Ra,YZg),(Cw,Ra,YZh),(Cw,Ra,YZi),(Cw,Ra,YZj),(Cw,Ra,YZk),(Cw,Ra,YZl),(Cw,Ra,YZm),(Cw,Ra,YZn),(Cw,Ra,YZo),(Cw,Ra,YZp),(Cw,Ra,YZq),(Cw,Ra,YZr),(Cw,Ra,YZs),(Cw,Ra,YZt),(Cw,Ra,YZu),(Cw,Ra,YZv),(Cw,Ra,YZw),(Cw,Ra,YZx),(Cw,Ra,YZy),(Cw,Ra,YZz),(Cw,Ra,YZaa),(Cw,Ra,YZab),(Cw,Ra,YZac),(Cw,Ra,YZad),(Cw,Ra,YZae),(Cw,Ra,YZaf),(Cw,Ra,YZag),(Cw,Rb,YZa),(Cw,Rb,YZb),(Cw,Rb,YZc),(Cw,Rb,YZd),(Cw,Rb,YZe),(Cw,Rb,YZf),(Cw,Rb,YZg),(Cw,Rb,YZh),(Cw,Rb,YZi),(Cw,Rb,YZj),(Cw,Rb,YZk),(Cw,Rb,YZl),(Cw,Rb,YZm),(Cw,Rb,YZn),(Cw,Rb,YZo),(Cw,Rb,YZp),(Cw,Rb,YZq),(Cw,Rb,YZr),(Cw,Rb,YZs),(Cw,Rb,YZt),(Cw,Rb,YZu),(Cw,Rb,YZv),(Cw,Rb,YZw),(Cw,Rb,YZx),(Cw,Rb,YZy),(Cw,Rb,YZz),(Cw,Rb,YZaa),(Cw,Rb,YZab),(Cw,Rb,YZac),(Cw,Rb,YZad),(Cw,Rb,YZae),(Cw,Rb,YZaf),(Cw,Rb,YZag),(Cw,Rc,YZa),(Cw,Rc,YZb),(Cw,Rc,YZc),(Cw,Rc,YZd),(Cw,Rc,YZe),(Cw,Rc,YZf),(Cw,Rc,YZg),(Cw,Rc,YZh),(Cw,Rc,YZi),(Cw,Rc,YZj),(Cw,Rc,YZk),(Cw,Rc,YZl),(Cw,Rc,YZm),(Cw,Rc,YZn),(Cw,Rc,YZo),(Cw,Rc,YZp),(Cw,Rc,YZq),(Cw,Rc,YZr),(Cw,Rc,YZs),(Cw,Rc,YZt),(Cw,Rc,YZu),(Cw,Rc,YZv),(Cw,Rc,YZw),(Cw,Rc,YZx),(Cw,Rc,YZy),(Cw,Rc,YZz),(Cw,Rc,YZaa),(Cw,Rc,YZab),(Cw,Rc,YZac),(Cw,Rc,YZad)(Cw,Rc,YZae),(Cw,Rc,YZaf),(Cw,Rc,YZag),(Cw,Rd,YZa),(Cw,Rd,YZb),(Cw,Rd,YZc),(Cw,Rd,YZd),(Cw,Rd,YZe),(Cw,Rd,YZf),(Cw,Rd,YZg),(Cw,Rd,YZh),(Cw,Rd,YZi),(Cw,Rd,YZj),(Cw,Rd,YZk),(Cw,Rd,YZl),(Cw,Rd,YZm),(Cw,Rd,YZn),(Cw,Rd,YZo),(Cw,Rd,YZp),(Cw,Rd,YZq),(Cw,Rd,YZr),(Cw,Rd,YZs),(Cw,Rd,YZt),(Cw,Rd,YZu),(Cw,Rd,YZv),(Cw,Rd,YZw),(Cw,Rd,YZx),(Cw,Rd,YZy),(Cw,Rd,YZz),(Cw,Rd,YZaa),(Cw,Rd,YZab),(Cw,Rd,YZac)(Cw,Rd,YZad),(Cw,Rd,YZae),(Cw,Rd,YZaf),(Cw,Rd,YZag),(Cw,Re,YZa),(Cw,Re,YZb),(Cw,Re,YZc),(Cw,Re,YZd),(Cw,Re,YZe),(Cw,Re,YZf),(Cw,Re,YZg),(Cw,Re,YZh),(Cw,Re,YZi),(Cw,Re,YZj),(Cw,Re,YZk),(Cw,Re,YZl),(Cw,Re,YZm),(Cw,Re,YZn),(Cw,Re,YZo),(Cw,Re,YZp),(Cw,Re,YZq),(Cw,Re,YZr),(Cw,Re,YZs),(Cw,Re,YZt),(Cw,Re,YZu),(Cw,Re,YZv),(Cw,Re,YZw),(Cw,Re,YZx),(Cw,Re,YZy),(Cw,Re,YZz),(Cw,Re,YZaa),(Cw,Re,YZab),(Cw,Re,YZac),(Cw,Re,YZad),(Cw,Re,YZae),(Cw,Re,YZaf),(Cw,Re,YZag),(Cx,Ra,YZa),(Cx,Ra,YZb),(Cx,Ra,YZc),(Cx,Ra,YZd),(Cx,Ra,YZe),(Cx,Ra,YZf),(Cx,Ra,YZg),(Cx,Ra,YZh),(Cx,Ra,YZi),(Cx,Ra,YZj),(Cx,Ra,YZk),(Cx,Ra,YZl),(Cx,Ra,YZm),(Cx,Ra,YZn),(Cx,Ra,YZo),(Cx,Ra,YZp),(Cx,Ra,YZq),(Cx,Ra,YZr),(Cx,Ra,YZs),(Cx,Ra,YZt),(Cx,Ra,YZu),(Cx,Ra,YZv),(Cx,Ra,YZw),(Cx,Ra,YZx),(Cx,Ra,YZy),(Cx,Ra,YZz),(Cx,Ra,YZaa),(Cx,Ra,YZab),(Cx,Ra,YZac),(Cx,Ra,YZad),(Cx,Ra,YZae),(Cx,Ra,YZaf),(Cx,Ra,YZag),(Cx,Rb,YZa),(Cx,Rb,YZb),(Cx,Rb,YZc),(Cx,Rb,YZd),(Cx,Rb,YZe),(Cx,Rb,YZf),(Cx,Rb,YZg),(Cx,Rb,YZh),(Cx,Rb,YZi),(Cx,Rb,YZj),(Cx,Rb,YZk),(Cx,Rb,YZl),(Cx,Rb,YZm),(Cx,Rb,YZn),(Cx,Rb,YZo),(Cx,Rb,YZp),(Cx,Rb,YZq),(Cx,Rb,YZr),(Cx,Rb,YZs),(Cx,Rb,YZt),(Cx,Rb,YZu),(Cx,Rb,

YZv), (Cx,Rb,YZw),(Cx,Rb,YZx),(Cx,Rb,YZy),(Cx,Rb,YZz),(Cx,Rb,YZaa),(Cx,Rb,YZab),(Cx,Rb, YZac),(Cx,Rb,YZad),(Cx,Rb,YZae),(Cx,Rb,YZaf),(Cx,Rb,YZag),(Cx,Rc,YZa),(Cx,Rc,YZb), (Cx,Rc,YZc),(Cx,Rc,YZd),(Cx,Rc,YZe),(Cx,Rc,YZf),(Cx,Rc,YZg),(Cx,Rc,YZh),(Cx,Rc,YZi),(Cx,Rc,YZj),(Cx,Rc,Ya),(Cx,Rc,YZl),(Cx,Rc,YZm),(Cx,Rc,YZn),(Cx,Rc,YZo),(Cx,Rc, YZp),(Cx,Rc,YZq),(Cx,Rc,YZr),(Cx,Rc,YZs),(Cx,Rc,YZt),(Cx,Rc,YZu),(Cx,Rc,YZv),(Cx,Rc,YZw),(Cx,Rc,YZx),(Cx,Rc,YZy),(Cx,Rc,YZz),(Cx,Rc,YZaa),(Cx,Rc,YZab),(Cx,Rc,YZac), (Cx,Rc,YZad),(Cx,Rc,YZae),(Cx,Rc,YZaf),(Cx,Rc,YZag),(Cx,Rd,YZa),(Cx,Rd,YZb),(Cx,Rd,YZc),(Cx,Rd,YZd),(Cx,Rd,YZe),(Cx,Rd,YZf),(Cx,Rd,YZg),(Cx,Rd,YZh),(Cx,Rd,YZi),(Cx,Rd,YZj),(Cx,Rd,YZk),(Cx,Rd,YZl),(Cx,Rd,YZm),(Cx,Rd,YZn),(Cx,Rd,YZo),(Cx,Rd,YZp), (Cx,Rd,YZq),(Cx,Rd,YZr),(Cx,Rd,YZs),(Cx,Rd,YZt),(Cx,Rd,YZu),(Cx,Rd,YZv),(Cx,Rd,YZw),(Cx,Rd,YZx),(Cx,Rd,YZy),(Cx,Rd,YZz),(Cx,Rd,YZaa),(Cx,Rd,YZab),(Cx,Rd,YZac),(Cx,Rd,YZad),(Cx,Rd,YZae),(Cx,Rd,YZaf),(Cx,Rd,YZag),(Cx,Re,YZa),(Cx,Re,YZb),(Cx,Re, YZc),(Cx,Re,YZd),(Cx,Re,YZe),(Cx,Re,YZf),(Cx,Re,YZg),(Cx,Re,YZh),(Cx,Re,YZi),(Cx,Re,YZj),(Cx,Re,YZk),(Cx,Re,YZl),(Cx,Re,YZm),(Cx,Re,YZn),(Cx,Re,YZo),(Cx,Re,YZp),(Cx,Re,YZq),(Cx,Re,YZr),(Cx,Re,YZs),(Cx,Re,YZt),(Cx,Re,YZu),(Cx,Re,YZy),(Cx,Re,YZw), (Cx,Re,YZx),(Cx,Re,YZy),(Cx,Re,YZz),(Cx,Re,YZaa),(Cx,Re,YZab),(Cx,Re,YZac),(Cx,Re, YZad),(Cx,Re,YZae),(Cx,Re,YZaf),(Cx,Re,YZag),(Cy,Ra,YZa),(Cy,Ra,YZb),(Cy,Ra,YZc), (Cy,Ra,YZd),(Cy,Ra,YZe),(Cy,Ra,YZf),(Cy,Ra,YZg),(Cy,Ra,YZh),(Cy,Ra,YZi),(Cy,Ra,YZj), (Cy,Ra,YZk),(Cy,Ra,YZl),(Cy,Ra,YZm),(Cy,Ra,YZn),(Cy,Ra,YZo),(Cy,Ra,YZp),(Cy,Ra,YZq),(Cy,Ra,YZr),(Cy,Ra,YZs),(Cy,Ra,YZt),(Cy,Ra,YZu),(Cy,Ra,YZv),(Cy,Ra,YZw),(Cy,Ra,YZx),(Cy,Ra,YZy),(Cy,Ra,YZz),(Cy,Ra,YZaa),(Cy,Ra,YZab),(Cy,Ra,YZac),(Cy,Ra,YZad), (Cy,Ra,YZae),(Cy,Ra,YZaf),(Cy,Ra,YZag),(Cy,Rb,YZa),(Cy,Rb,YZb),(Cy,Rb,YZc),(Cy,Rb, YZd),(Cy,Rb,YZe),(Cy,Rb,YZf),(Cy,Rb,YZg),(Cy,Rb,YZh),(Cy,Rb,YZi),(Cy,Rb,YZj),(Cy,Rb,YZk),(Cy,Rb,YZl),(Cy,Rb,YZm),(Cy,Rb,YZn),(Cy,Rb,YZo),(Cy,Rb,YZp),(Cy,Rb,YZq), (Cy,Rb,YZr),(Cy,Rb,YZs),(Cy,Rb,YZt),(Cy,Rb,YZu),(Cy,Rb,YZv),(Cy,Rb,YZw),(Cy,Rb,YZx),(Cy,Rb,YZy),(Cy,Rb,YZz),(Cy,Rb,YZaa),(Cy,Rb,YZab),(Cy,Rb,YZac),(Cy,Rb,YZad), (Cy,Rb,YZae),(Cy,Rb,YZaf),(Cy,Rb,YZag),(Cy,Rc,YZa),(Cy,Rc,YZb),(Cy,Rc,YZc),(Cy,Rc, YZd),(Cy,Rc,YZe),(Cy,Rc,YZf),(Cy,Rc,YZg),(Cy,Rc,YZh),(Cy,Rc,YZi),(Cy,Rc,YZj),(Cy,Rc,YZk),(Cy,Rc,YZl),(Cy,Rc,YZm),(Cy,Rc,YZn),(Cy,Rc,YZo),(Cy,Rc,YZp),(Cy,Rc,YZq),(Cy,Rc,YZr),(Cy,Rc,YZs),(Cy,Rc,YZt),(Cy,Rc,YZu),(Cy,Rc,YZv),(Cy,Rc,YZw),(Cy,Rc,YZx), (Cy,Rc,YZy),(Cy,Rc,YZz),(Cy,Rc,YZaa),(Cy,Rc,YZab),(Cy,Rc,YZac),(Cy,Rc,YZad),(Cy,Rc,YZae),(Cy,Rc,YZaf),(Cy,Rc,YZag),(Cy,Rd,YZa),(Cy,Rd,YZb),(Cy,Rd,YZc),(Cy,Rd,YZd), (Cy,Rd,YZe),(Cy,Rd,YZf),(Cy,Rd,YZg),(Cy,Rd,YZh),(Cy,Rd,YZi),(Cy,Rd,YZj),(Cy,Rd,YZk),(Cy,Rd,YZl),(Cy,Rd,YZm),(Cy,Rd,YZn),(Cy,Rd,YZo),(Cy,Rd,YZp),(Cy,Rd,YZq),(Cy,Rd,YZr),(Cy,Rd,YZs),(Cy,Rd,YZt),(Cy,Rd,YZu),(Cy,Rd,YZv),(Cy,Rd,YZw),(Cy,Rd,YZx),(Cy,Rd,YZy),(Cy,Rd,YZz),(Cy,Rd,YZaa),(Cy,Rd,YZab),(Cy,Rd,YZac),(Cy,Rd,YZad),(Cy,Rd,YZae),(Cy,Rd,YZaf),(Cy,Rd,YZag),(Cy,Re,YZa),(Cy,Re,YZb),(Cy,Re,YZc),(Cy,Re,YZd),(Cy, Re,YZe),(Cy,Re,YZf),(Cy,Re,YZg),(Cy,Re,YZh),(Cy,Re,YZi),(Cy,Re,YZj),(Cy,Re,YZk),(Cy,Re,YZl),(Cy,Re,YZm),(Cy,Re,YZn),(Cy,Re,YZo),(Cy,Re,YZp),(Cy,Re,YZq),(Cy,Re,YZr), (Cy,Re,YZs),(Cy,Re,YZt),(Cy,Re,YZu),(Cy,Re,YZy),(Cy,Re,YZw),(Cy,Re,YZx),(Cy,Re,YZy) (Cy,Re,YZz),(Cy,Re,YZaa),(Cy,Re,YZab),(Cy,Re,YZac),(Cy,Re,YZad),(Cy,Re,YZae),(Cy,Re,YZaf),(Cy,Re,YZag),(Cz,Ra,YZa),(Cz,Ra,YZb),(Cz,Ra,YZc),(Cz,Ra,YZd),(Cz,Ra,YZe), (Cz,Ra,YZf),(Cz,Ra,YZg),(Cz,Ra,YZh),(Cz,Ra,YZi),(Cz,Ra,YZj),(Cz,Ra,YZk),(Cz,Ra,YZl), (Cz,Ra,YZm),(Cz,Ra,YZn),(Cz,Ra,YZo),(Cz,Ra,YZp),(Cz,Ra,YZq),(Cz,Ra,YZr),(Cz,Ra,YZs),(Cz,Ra,YZt),(Cz,Ra,YZu),(Cz,Ra,YZy),(Cz,Ra,YZw),(Cz,Ra,YZx),(Cz,Ra,YZy),(Cz,Ra,YZz),(Cz,Ra,YZaa),(Cz,Ra,YZab),(Cz,Ra,YZac),(Cz,Ra,YZad),(Cz,Ra,YZae),(Cz,Ra,YZaf), (Cz,Ra,YZag),(Cz,Rb,YZa),(Cz,Rb,YZb),(Cz,Rb,YZc),(Cz,Rb,YZd),(Cz,Rb,YZe),(Cz,Rb,YZf),(Cz,Rb,YZg),(Cz,Rb,YZh),(Cz,Rb,YZi),(Cz,Rb,YZj),(Cz,Rb,Ya),(Cz,Rb,YZl),(Cz,Rb,YZm),(Cz,Rb,YZn),(Cz,Rb,YZo),(Cz,Rb,YZp),(Cz,Rb,YZq),(Cz,Rb,YZr),(Cz,Rb,YZs),(Cz,Rb,YZt),(Cz,Rb,YZu),(Cz,Rb,YZy),(Cz,Rb,YZw),(Cz,Rb,YZx),(Cz,Rb,YZy),(Cz,Rb,YZz), (Cz,Rb,YZaa),(Cz,Rb,YZab),(Cz,Rb,YZac),(Cz,Rb,YZad),(Cz,Rb,YZae),(Cz,Rb,YZaf),(Cz,Rb,YZag),(Cz,Rc,YZa),(Cz,Rc,YZb),(Cz,Rc,YZc),(Cz,Rc,YZd),(Cz,Rc,YZe),(Cz,Rc,YZf),(Cz,Rc,YZg),(Cz,Rc,YZl),(Cz,Rc,YZi),(Cz,Rc,YZj),(Cz,Rc,YZk),(Cz,Rc,YZl),(Cz,Rc,YZm),(Cz,Rc,YZn),(Cz,Rc,YZo),(Cz,Rc,YZp),(Cz,Rc,YZq),(Cz,Rc,YZr),(Cz,Rc,YZs),(Cz,Rc,YZt), (Cz,Rc,YZu),(Cz,Rc,YZy),(Cz,Rc,YZw),(Cz,Rc,YZx),(Cz,Rc,YZy),(Cz,Rc,YZz),(Cz,Rc,YZaa) (Cz,Rc,YZab),(Cz,Rc,YZac),(Cz,Rc,YZad),(Cz,Rc,YZae),(Cz,Rc,YZaf),(Cz,Rc,YZag),(Cz,Rd,YZa),(Cz,Rd,YZb),(Cz,Rd,YZc),(Cz,Rd,YZd),(Cz,Rd,YZe),(Cz,Rd,YZf),(Cz,Rd,YZg), (Cz,Rd,YZh),(Cz,Rd,YZi),(Cz,Rd,YZj),(Cz,Rd,YZk),(Cz,Rd,YZl),(Cz,Rd,YZm),(Cz,Rd,YZn) (Cz,Rd,YZo),(Cz,Rd,YZp),(Cz,Rd,YZq),(Cz,Rd,YZr),(Cz,Rd,YZs),(Cz,Rd,YZt),(Cz,Rd,YZu),(Cz,Rd,YZv),(Cz,Rd,YZw),(Cz,Rd,YZx),(Cz,Rd,YZy),(Cz,Rd,YZz),(Cz,Rd,YZaa),(Cz,Rd,YZab),(Cz,Rd,YZac),(Cz,Rd,YZad),(Cz,Rd,YZae),(Cz,Rd,YZaf),(Cz,Rd,YZag),(Cz,Re, YZa),(Cz,Re,YZb),(Cz,Re,YZc),(Cz,Re,YZd),(Cz,Re,YZe),(Cz,Re,YZf),(Cz,Re,YZg),(Cz,Re,YZh),(Cz,Re,YZi),(Cz,Re,YZj),(Cz,Re,YZk),(Cz,Re,YZl),(Cz,Re,YZm),(Cz,Re,YZn),(Cz,Re,YZo),(Cz,Re,YZp),(Cz,Re,YZq),(Cz,Re,YZr),(Cz,Re,YZs),(Cz,Re,YZt),(Cz,Re,YZu),(Cz,Re,YZv),(Cz,Re,YZw),(Cz,Re,YZx),(Cz,Re,YZy),(Cz,Re,YZz),(Cz,Re,YZaa),(Cz,Re,YZab), (Cz,Re,YZac),(Cz,Re,YZad),(Cz,Re,YZae),(Cz,Re,YZaf),(Cz,Re,YZag),(Caa,Ra,YZa),(Caa,Ra,YZb),(Caa,Ra,YZc),(Caa,Ra,YZd),(Caa,Ra,YZe),(Caa,Ra,YZf),(Caa,Ra,YZg),(Caa,Ra,YZh),(Caa,Ra,YZi),(Caa,Ra,YZj),(Caa,Ra,YZk),(Caa,Ra,YZl),(Caa,Ra,YZm),(Caa,Ra,YZn), (Caa,Ra,YZo),(Caa,Ra,YZp),(Caa,Ra,YZq),(Caa,Ra,YZr),(Caa,Ra,YZs),(Caa,Ra,YZt),(Caa,Ra,YZu),(Caa,Ra,YZy),(Caa,Ra,YZw),(Caa,Ra,YZx),(Caa,Ra,YZy),(Caa,Ra,YZz),(Caa,Ra,YZaa),(Caa,Ra,YZab),(Caa,Ra,YZac),(Caa,Ra,YZad),(Caa,Ra,YZae),(Caa,Ra,YZaf),(Caa,Ra,YZag),(Caa,Rb,YZa),(Caa,Rb,YZb),(Caa,Rb,YZc),(Caa,Rb,YZd),(Caa,Rb,YZe),(Caa,Rb,YZf) (Caa,Rb,YZg),(Caa,Rb,YZh),(Caa,Rb,YZi),(Caa,Rb,YZj),(Caa,Rb,YZk),(Caa,Rb,YZl),(Caa,Rb,YZm),(Caa,Rb,YZn),(Caa,Rb,YZo),(Caa,Rb,YZp),(Caa,Rb,YZq),(Caa,Rb,YZr),(Caa,Rb,YZs),(Caa,Rb,YZt),(Caa,Rb,YZu),(Caa,Rb,YZy),(Caa,Rb,YZw),(Caa,Rb,YZx),(Caa,Rb,YZy),(Caa,Rb,YZz),(Caa,Rb,YZaa),(Caa,Rb,YZab),(Caa,Rb,YZac),(Caa,Rb,YZad),(Caa,Rb,YZae),(Caa,Rb,YZaf),(Caa,Rb,YZag),(Caa,Rc,YZa),(Caa,Rc,YZb),(Caa,Rc,YZc),(Caa,Rc,YZd) (Caa,Rc,YZe),(Caa,Rc,YZf),(Caa,Rc,YZg),(Caa,Rc,YZh),(Caa,Rc,YZi),(Caa,Rc,YZj),(Caa,Rc,YZk),(Caa,Rc,YZl),(Caa,Rc,YZm),(Caa,Rc,YZn),(Caa,Rc,YZo),(Caa,Rc,YZp),(Caa,Rc,YZq),(Caa,Rc,YZr),(Caa,Rc,YZs),(Caa,Rc,YZt),(Caa,Rc,YZu),(Caa,Rc,YZy),(Caa,Rc,YZy),(Caa,Rc,YZw), (Caa,Rc,YZx),(Caa,Rc,YZy),(Caa,Rc,YZz),(Caa,Rc,YZaa),(Caa,Rc,YZab), (Caa,Rc,YZac), (Caa,Rc,YZad),(Caa,Rc,YZae),(Caa,Rc,YZaf),(Caa,Rc,YZag),(Caa,Rd,YZa),(Caa,Rd,YZb), (Caa,

Rd,YZc),(Caa,Rd,YZd),(Caa,Rd,YZe),(Caa,Rd,YZf),(Caa,Rd,YZg),(Caa,Rd,YZh),(Caa, Rd,YZi),(Caa,Rd,YZj),(Caa,Rd,YZk),(Caa,Rd,YZl),(Caa,Rd,YZm),(Caa,Rd,YZn),(Caa,Rd,Y Zo),(Caa,Rd,YZp),(Caa,Rd,YZq),(Caa,Rd,YZr),(Caa,Rd,YZs),(Caa,Rd,YZt),(Caa,Rd,YZu), (Caa,Rd,YZy),(Caa,Rd,YZw),(Caa,Rd,YZx),(Caa,Rd,YZy),(Caa,Rd,YZz), (Caa,Rd,YZaa),(Ca a,Rd,YZab),(Caa,Rd,YZac),(Caa,Rd,YZad),(Caa,Rd,YZae),(Caa,Rd,YZaf),(Caa,Rd,YZag), (Caa,Re,YZa),(Caa,Re,YZb),(Caa,Re,YZc),(Caa,Re,YZd), (Caa,Re,YZe),(Caa,Re,YZf),(Caa, Re,YZg),(Caa,Re,YZh), (Caa,Re,YZi),(Caa,Re,YZj),(Caa,Re,YZk),(Caa,Re,YZl), (Caa,Re,YZ m) (Caa,Re,YZn),(Caa,Re,YZo),(Caa,Re,YZp), (Caa,Re,YZq),(Caa,Re,YZr),(Caa,Re,YZs),(C aa,Re,YZt), (Caa,Re,YZu),(Caa,Re,YZv),(Caa,Re,YZw),(Caa,Re,YZx), (Caa,Re,YZy),(Caa,R e,YZz),(Caa,Re,YZaa),(Caa,Re, YZab),(Caa,Re,YZac),(Caa,Re,YZad),(Caa,Re,YZae), (Caa,R e,YZaf),(Caa,Re,YZag),(Cab,Ra,YZa),(Cab,Ra, YZb),(Cab,Ra,YZc),(Cab,Ra,YZd),(Cab,Ra, YZe),(Cab,Ra, YZf),(Cab,Ra,YZg),(Cab,Ra,YZh),(Cab,Ra,YZi),(Cab,Ra, YZj),(Cab,Ra,YZk), (Cab,Ra,YZl),(Cab,Ra,YZm),(Cab,Ra, YZn),(Cab,Ra,YZo),(Cab,Ra,YZp),(Cab,Ra,YZq),(Ca b,Ra,YZr),(Cab,Ra,YZs),(Cab,Ra,YZt),(Cab,Ra,YZu), (Cab,Ra,YZy),(Cab,Ra,YZw),(Cab,Ra, YZx),(Cab,Ra, YZy),(Cab,Ra,YZz),(Cab,Ra,YZaa),(Cab,Ra,YZab),(Cab, Ra,YZac),(Cab,Ra, YZad),(Cab,Ra,YZae),(Cab,Ra,YZaf), (Cab,Ra,YZag),(Cab,Rb,YZa),(Cab,Rb,YZb),(Cab,Rb, YZc),(Cab,Rb,YZd),(Cab,Rb,YZe),(Cab,Rb,YZf),(Cab,Rb, YZg),(Cab,Rb,YZh),(Cab,Rb,YZi), (Cab,Rb,YZj),(Cab,Rb, YZk),(Cab,Rb,YZl),(Cab,Rb,YZm),(Cab,Rb,YZn),(Cab, Rb,YZo),(C ab,Rb,YZp),(Cab,Rb,YZq),(Cab,Rb,YZr), (Cab,Rb,YZs),(Cab,Rb,YZt),(Cab,Rb,YZu),(Cab,R b,YZv), (Cab,Rb,YZw),(Cab,Rb,YZx),(Cab,Rb,YZy),(Cab,Rb, YZz),(Cab,Rb,YZaa),(Cab,Rb, YZab),(Cab,Rb,YZac),(Cab, Rb,YZad),(Cab,Rb,YZae),(Cab,Rb,YZaf),(Cab,Rb,YZag), (Cab, Rc,YZa),(Cab,Rc,YZb),(Cab,Rc,YZc),(Cab,Rc,YZd), (Cab,Rc,YZe),(Cab,Rc,YZf),(Cab,Rc,Y Zg),(Cab,Rc,YZh), (Cab,Rc,YZi),(Cab,Rc,YZj),(Cab,Rc,YZk),(Cab,Rc,YZl), (Cab,Rc,YZm), (Cab,Rc,YZn),(Cab,Rc,YZo),(Cab,Rc, YZp),(Cab,Rc,YZq),(Cab,Rc,YZr),(Cab,Rc,YZs),(Cab, Rc,YZt),(Cab,Rc,YZu),(Cab,Rc,YZy),(Cab,Rc,YZw),(Cab, Rc,YZx),(Cab,Rc,YZy),(Cab,Rc, YZz),(Cab,Rc,YZaa),(Ca- b,Rc,YZab),(Cab,Rc,YZac),(Cab,Rc,YZad),(Cab,Rc, YZae),(Cab,Rc, YZaf),(Cab,Rc,YZag),(Cab,Rd,YZa),(Cab, Rd,YZb),(Cab,Rd,YZc),(Cab,Rd,YZd),(Cab,Rd, YZe), (Cab,Rd,YZf),(Cab,Rd,YZg),(Cab,Rd,YZh),(Cab,Rd,YZi), (Cab,Rd,YZj),(Cab,Rd,YZk), (Cab,Rd,YZl),(Cab,Rd, YZm),(Cab,Rd,YZn),(Cab,Rd,YZo),(Cab,Rd,YZp),(Cab, Rd,YZq), (Cab,Rd,YZr),(Cab,Rd,YZs),(Cab,Rd,YZt),(Cab, Rd,YZu),(Cab,Rd,YZy),(Cab,Rd,YZw),(Cab, Rd,YZx), (Cab,Rd,YZy),(Cab,Rd,YZz),(Cab,Rd,YZaa),(Cab,Rd, YZab),(Cab,Rd,YZac),(Cab, Rd,YZad),(Cab,Rd,YZae), (Cab,Rd,YZaf),(Cab,Rd,YZag),(Cab,Re,YZa),(Cab,Re, YZb),(Cab, Re,YZc),(Cab,Re,YZd),(Cab,Re,YZe),(Cab,Re, YZf),(Cab,Re,YZg),(Cab,Re,YZh),(Cab,Re, YZi),(Cab,Re, YZj),(Cab,Re,YZk),(Cab,Re,YZl),(Cab,Re,YZm),(Cab,Re, YZn),(Cab,Re,YZo), (Cab,Re,YZp),(Cab,Re,YZq),(Cab, Re,YZr),(Cab,Re,YZs),(Cab,Re,YZt),(Cab,Re,YZu),(Cab, Re,YZy),(Cab,Re,YZw),(Cab,Re,YZx),(Cab,Re,YZy), (Cab,Re,YZz),(Cab,Re,YZaa),(Cab,R e,YZab),(Cab,Re, YZac),(Cab,Re,YZad),(Cab,Re,YZae),(Cab,Re,YZaf), (Cab,Re,YZag),(Cac, Ra,YZa),(Cac,Ra,YZb),(Cac,Ra, YZc),(Cac,Ra,YZd),(Cac,Ra,YZe),(Cac,Ra,YZf),(Cac, Ra,Y Zg),(Cac,Ra,YZh),(Cac,Ra,YZi),(Cac,Ra,YZj),(Cac, Ra,YZk),(Cac,Ra,YZl),(Cac,Ra,YZm), (Cac,Ra,YZn),(Cac, Ra,YZo),(Cac,Ra,YZp),(Cac,Ra,YZq),(Cac,Ra,YZr),(Cac, Ra,YZs),(Cac, Ra,YZt),(Cac,Ra,YZu),(Cac,Ra,YZv),(Cac, Ra,YZw),(Cac,Ra,YZx),(Cac,Ra,YZy),(Cac,Ra,Y Zz),(Cac, Ra,YZaa),(Cac,Ra,YZab),(Cac,Ra,YZac),(Cac,Ra,YZad), (Cac,Ra,YZae),(Cac,Ra,Y Zaf),(Cac,Ra,YZag),(Cac,Rb, YZa),(Cac,Rb,YZb),(Cac,Rb,YZc),(Cac,Rb,YZd),(Cac,Rb, YZe), (Cac,Rb,YZf),(Cac,Rb,YZg),(Cac,Rb,YZh),(Cac,Rb, YZi),(Cac,Rb,YZj),(Cac,Rb,YZk),(Ca c,Rb,YZl),(Cac,Rb, YZm),(Cac,Rb,YZn),(Cac,Rb,YZo),(Cac,Rb,YZp),(Cac, Rb,YZq),(Cac,R b,YZr),(Cac,Rb,YZs),(Cac,Rb,YZt),(Cac, Rb,YZu),(Cac,Rb,YZy),(Cac,Rb,YZw),(Cac,Rb,Y Zx), (Cac,Rb,YZy),(Cac,Rb,YZz),(Cac,Rb,YZaa),(Cac,Rb, YZab),(Cac,Rb,YZac),(Cac,Rb,YZ ad),(Cac,Rb,YZae), (Cac,Rb,YZaf),(Cac,Rb,YZag),(Cac,Rc,YZa),(Cac,Rc, YZb),(Cac,Rc,YZc), (Cac,Rc,YZd),(Cac,Rc,YZe),(Cac,Rc, YZf),(Cac,Rc,YZg),(Cac,Rc,YZh),(Cac,Rc,YZi),(Cac, Rc,YZj),(Cac,Rc,YZk),(Cac,Rc,YZl),(Cac,Rc,YZm),(Cac, Rc,YZn),(Cac,Rc,YZo),(Cac,Rc, YZp),(Cac,Rc,YZq),(Cac, Rc,YZr),(Cac,Rc,YZs),(Cac,Rc,YZt),(Cac,Rc,YZu),(Cac, Rc,YZv), (Cac,Rc,YZw),(Cac,Rc,YZx),(Cac,Rc,YZy), (Cac,Rc,YZz),(Cac,Rc,YZaa),(Cac,Rc,YZab),(C ac,Rc, YZac),(Cac,Rc,YZad),(Cac,Rc,YZae),(Cac,Rc,YZaf),(Cac, Rc,YZag),(Cac,Rd,YZa),(C ac,Rd,YZb),(Cac,Rd,YZc), (Cac,Rd,YZd),(Cac,Rd,YZe),(Cac,Rd,YZf),(Cac,Rd,YZg), (Cac,R d,YZh),(Cac,Rd,YZi),(Cac,Rd,YZj),(Cac,Rd,YZk), (Cac,Rd,YZl),(Cac,Rd,YZm),(Cac,Rd,YZ n) (Cac,Rd,YZo), (Cac,Rd,YZp),(Cac,Rd,YZq),(Cac,Rd,YZr),(Cac,Rd,YZs), (Cac,Rd,YZt),(C ac,Rd,YZu),(Cac,Rd,YZy),(Cac,Rd, YZw),(Cac,Rd,YZx),(Cac,Rd,YZy),(Cac,Rd,YZz),(Cac, Rd,YZaa),(Cac,Rd,YZab),(Cac,Rd,YZac),(Cac,Rd,YZad), (Cac,Rd,YZae),(Cac,Rd,YZaf),(Ca c,Rd,YZag),(Cac,Re, YZa),(Cac,Re,YZb),(Cac,Re,YZc),(Cac,Re,YZd),(Cac,Re, YZe),(Cac,R e,YZl),(Cac,Re,YZg),(Cac,Re,YZh),(Cac,Re, YZi),(Cac,Re,YZj),(Cac,Re,YZk),(Cac,Re,YZl), (Cac,Re, YZm),(Cac,Re,YZn),(Cac,Re,YZo),(Cac,Re,YZp),(Cac,Re, YZq),(Cac,Re,YZr),(Ca c,Re,YZs),(Cac,Re,YZt),(Cac,Re, YZu),(Cac,Re,YZy),(Cac,Re,YZw),(Cac,Re,YZx),(Cac,Re, YZy),(Cac,Re,YZz),(Cac,Re,YZaa),(Cac,Re,YZab),(Cac, Re,YZac),(Cac,Re,YZad),(Cac,Re, YZae),(Cac,Re,YZaf), (Cac,Re,YZag),(Cad,Ra,YZa),(Cad,Ra,YZb),(Cad,Ra, YZc),(Cad,Ra,Y Zd),(Cad,Ra,YZe),(Cad,Ra,YZf),(Cad,Ra, YZg),(Cad,Ra,YZh),(Cad,Ra,YZi),(Cad,Ra,YZj), (Cad,Ra, YZk),(Cad,Ra,YZl),(Cad,Ra,YZm),(Cad,Ra,YZn),(Cad,Ra, YZo),(Cad,Ra,YZp),(Cad, Ra,YZq),(Cad,Ra,YZr),(Cad,Ra, YZs),(Cad,Ra,YZt),(Cad,Ra,YZu),(Cad,Ra,YZy),(Cad,Ra, YZw),(Cad,Ra,YZx),(Cad,Ra,YZy),(Cad,Ra,YZz),(Cad, Ra,YZaa),(Cad,Ra,YZab),(Cad,Ra,Y Zac),(Cad,Ra,YZad), (Cad,Ra,YZae),(Cad,Ra,YZaf),(Cad,Ra,YZag),(Cad,Rb, YZa),(Cad,Rb, YZb),(Cad,Rb,YZc),(Cad,Rb,YZd),(Cad, Rb,YZe),(Cad,Rb,Ya),(Cad,Rb,YZg),(Cad,Rb,YZ h) (Cad, Rb,YZi),(Cad,Rb,YZj),(Cad,Rb,YZk),(Cad,Rb,YZl),(Cad, Rb,YZm),(Cad,Rb,YZn), (Cad,Rb,YZo),(Cad,Rb,YZp), (Cad,Rb,YZq),(Cad,Rb,YZr),(Cad,Rb,YZs),(Cad,Rb,YZt), (Cad, Rb,YZu),(Cad,Rb,YZv),(Cad,Rb,YZw),(Cad,Rb, YZx),(Cad,Rb,YZy),(Cad,Rb,YZz),(Cad,Rb, YZaa),(Cad, Rb,YZab),(Cad,Rb,YZac),(Cad,Rb,YZad),(Cad,Rb,YZae), (Cad,Rb,YZaf),(Cad, Rb,YZag),(Cad,Rc,YZa),(Cad,Rc, YZb),(Cad,Rc,YZc),(Cad,Rc,YZd),(Cad,Rc,YZe),(Cad,Rc, YZf),(Cad,Rc,YZg),(Cad,Rc,YZh),(Cad,Rc,YZi),(Cad,Rc, YZj),(Cad,Rc,YZk),(Cad,Rc,YZl), (Cad,Rc,YZm),(Cad,Rc, YZn),(Cad,Rc,YZo),(Cad,Rc,YZp),(Cad,Rc,YZq),(Cad,Rc, YZr),(Ca d,Rc,YZs),(Cad,Rc,YZt),(Cad,Rc,YZu),(Cad,Rc, YZy),(Cad,Rc,YZw),(Cad,Rc,YZx),(Cad,Rc, YZy),(Cad, Rc,YZz),(Cad,Rc,YZaa),(Cad,Rc,YZab),(Cad,Rc,YZac), (Cad,Rc,YZad),(Cad,Rc, YZae),(Cad,Rc,YZaf),(Cad,Rc, YZag),(Cad,Rd,YZa),(Cad,Rd,YZb),(Cad,Rd,YZc),(Cad, Rd,YZd),(Cad,Rd,YZe),(Cad,Rd,YZf),(Cad,Rd,YZg),(Cad, Rd,YZh),(Cad,Rd,YZi),(Cad,Rd,YZj), (Cad,Rd,Ya),(Cad, Rd,YZl),(Cad,Rd,YZm),(Cad,Rd,YZn),(Cad,Rd,YZo), (Cad,Rd,YZp), (Cad,Rd,YZq),(Cad,Rd,YZr),(Cad,Rd,YZs), (Cad,Rd,YZt),(Cad,Rd,YZu),(Cad,Rd,YZy),(Cad,Rd,YZw),(Cad,Rd,YZx),(Cad,Rd,YZy),(Cad,Rd,YZz),(Cad,Rd,YZaa),(Cad,Rd,YZab),(Cad,Rd,YZac),(Cad,Rd,YZad),(Cad,Rd,YZae),(Cad,Rd,YZaf),(Cad,Rd,YZag),(Cad,Re,YZa),(Cad,Re,YZb),(Cad,Re,YZc),(Cad,Re,Yal),(Cad,Re,YZe),(Cad,Re,YZf),(Cad,Re,YZg),(Cad,Re,YZh),(Cad,Re,YZi),(Cad,Re,YZj),(Cad,Re,YZk),(Cad,Re,YZl),(Cad,Re,YZm),(Cad,Re,YZn),(Cad,Re,YZo),(Cad,Re,YZp),(Cad,Re,YZq),(Cad,Re,YZr),(Cad,Re,YZs),(Cad,Re,YZt),(Cad,Re,YZu),(Cad,Re,YZy),(Cad,Re,YZw),(Cad,Re,YZx),(Cad,Re,YZy),(Cad,Re,YZz),(Cad,Re,YZaa),(Cad,Re,YZab),(Cad,Re,YZac),(Cad,Re,YZad),(Cad,Re,YZae),(Cad,Re,YZaf),(Cad,Re,YZag),(Cae,Ra,YZa),(Cae,Ra,YZb),(Cae,Ra,YZc),(Cae,Ra,YZd),(Cae,Ra,YZe),(Cae,Ra,YZf),(Cae,Ra,YZg),(Cae,Ra,YZh),(Cae,Ra,YZi),(Cae,Ra,YZj),(Cae,Ra,YZk),(Cae,Ra,YZl),(Cae,Ra,YZm),(Cae,Ra,YZn),(Cae,Ra,YZo),(Cae,Ra,YZp),(Cae,Ra,YZq),(Cae,Ra,YZr),(Cae,Ra,YZs),(Cae,Ra,YZt),(Cae,Ra,YZu),(Cae,Ra,YZy),(Cae,Ra,YZw),(Cae,Ra,YZx),(Cae,Ra,YZy),(Cae,Ra,YZz),(Cae,Ra,YZaa),(Cae,Ra,YZab),(Cae,Ra,YZac),(Cae,Ra,YZad),(Cae,Ra,YZae),(Cae,Ra,YZaf),(Cae,Ra,YZag),(Cae,Rb,YZa),(Cae,Rb,YZb),(Cae,Rb,YZc),(Cae,Rb,YZd),(Cae,Rb,YZe),(Cae,Rb,YZf),(Cae,Rb,YZg),(Cae,Rb,Ya),(Cae,Rb,YZi),(Cae,Rb,YZj),(Cae,Rb,YZk),(Cae,Rb,YZl),(Cae,Rb,YZm),(Cae,Rb,YZn),(Cae,Rb,YZo),(Cae,Rb,YZp),(Cae,Rb,YZq),(Cae,Rb,YZr),(Cae,Rb,YZs),(Cae,Rb,YZt),(Cae,Rb,YZu),(Cae,Rb,YZv),(Cae,Rb,YZw),(Cae,Rb,YZx),(Cae,Rb,YZy),(Cae,Rb,YZz),(Cae,Rb,YZaa),(Cae,Rb,YZab),(Cae,Rb,YZac),(Cae,Rb,YZad),(Cae,Rb,YZae),(Cae,Rb,YZaf),(Cae,Rb,YZag),(Cae,Rc,YZa),(Cae,Rc,YZb),(Cae,Rc,YZc),(Cae,Rc,YZd),(Cae,Rc,YZe),(Cae,Rc,YZf),(Cae,Rc,YZg),(Cae,Rc,YZh),(Cae,Rc,YZi),(Cae,Rc,YZj),(Cae,Rc,YZk),(Cae,Rc,YZl),(Cae,Rc,YZm),(Cae,Rc,YZn),(Cae,Rc,YZo),(Cae,Rc,YZp),(Cae,Rc,YZq),(Cae,Rc,YZr),(Cae,Rc,YZs),(Cae,Rc,YZt),(Cae,Rc,YZu),(Cae,Rc,YZv),(Cae,Rc,YZw),(Cae,Rc,YZx),(Cae,Rc,YZy),(Cae,Rc,YZz),(Cae,Rc,YZaa),(Cae,Rc,YZab),(Cae,Rc,YZac),(Cae,Rc,YZad),(Cae,Rc,YZae),(Cae,Rc,YZaf),(Cae,Rc,YZag),(Cae,Rd,YZa),(Cae,Rd,YZb),(Cae,Rd,YZc),(Cae,Rd,YZd),(Cae,Rd,YZe),(Cae,Rd,YZf),(Cae,Rd,YZg),(Cae,Rd,Ya),(Cae,Rd,YZi),(Cae,Rd,YZj),(Cae,Rd,YZk),(Cae,Rd,YZl),(Cae,Rd,YZm),(Cae,Rd,YZn),(Cae,Rd,YZo),(Cae,Rd,YZp),(Cae,Rd,YZq),(Cae,Rd,YZr),(Cae,Rd,YZs),(Cae,Rd,YZt),(Cae,Rd,YZu),(Cae,Rd,YZy),(Cae,Rd,YZz),(Cae,Rd,YZaa),(Cae,Rd,YZab),(Cae,Rd,YZac),(Cae,Rd,YZad),(Cae,Rd,YZae),(Cae,Rd,YZaf),(Cae,Rd,YZag),(Cae,Re,YZa),(Cae,Re,YZb),(Cae,Re,YZc),(Cae,Re,YZA),(Cae,Re,YZe),(Cae,Re,YZf),(Cae,Re,YZg),(Cae,Re,YZh),(Cae,Re,YZi),(Cae,Re,YZj),(Cae,Re,Ya),(Cae,Re,YZl),(Cae,Re,YZm),(Cae,Re,YZn),(Cae,Re,YZo),(Cae,Re,YZp),(Cae,Re,YZq),(Cae,Re,YZr),(Cae,Re,YZs),(Cae,Re,YZt),(Cae,Re,YZu),(Cae,Re,YZv),(Cae,Re,YZw),(Cae,Re,YZx),(Cae,Re,YZy),(Cae,Re,YZz),(Cae,Re,YZaa),(Cae,Re,YZab),(Cae,Re,YZac),(Cae,Re,YZad),(Cae,Re,YZae),(Cae,Re,YZaf),(Cae,Re,YZag),(Caf,Ra,YZa),(Caf,Ra,YZb),(Caf,Ra,YZc),(Caf,Ra,YZd),(Caf,Ra,YZe),(Caf,Ra,YZf),(Caf,Ra,YZg),(Caf,Ra,YZh),(Caf,Ra,YZi),(Caf,Ra,YZj),(Caf,Ra,YZk),(Caf,Ra,YZl),(Caf,Ra,YZm),(Caf,Ra,YZn),(Caf,Ra,YZo),(Caf,Ra,YZp),(Caf,Ra,YZq),(Caf,Ra,YZr),(Caf,Ra,YZs),(Caf,Ra,YZt),(Caf,Ra,YZu),(Caf,Ra,YZy),(Caf,Ra,YZw),(Caf,Ra,YZx),(Caf,Ra,YZy),(Caf,Ra,YZz),(Caf,Ra,YZaa),(Caf,Ra,YZab),(Caf,Ra,YZac),(Caf,Ra,YZad),(Caf,Ra,YZae),(Caf,Ra,YZaf),(Caf,Ra,YZag),(Caf,Rb,YZa),(Caf,Rb,YZb),(Caf,Rb,YZc),(Caf,Rb,YZd),(Caf,Rb,YZe),(Caf,Rb,YZf),(Caf,Rb,YZg),(Caf,Rb,YZh),(Caf,Rb,YZi),(Caf,Rb,YZj),(Caf,Rb,YZk),(Caf,Rb,YZl),(Caf,Rb,YZm),(Caf,Rb,YZn),(Caf,Rb,YZo),(Caf,Rb,YZp),(Caf,Rb,YZq),(Caf,Rb,YZr),(Caf,Rb,YZs),(Caf,Rb,YZt),(Caf,Rb,YZu),(Caf,Rb,YZy),(Caf,Rb,YZw),(Caf,Rb,YZx),(Caf,Rb,YZy),(Caf,Rb,YZz),(Caf,Rb,YZaa),(Caf,Rb,YZab),(Caf,Rb,YZac),(Caf,Rb,YZad),(Caf,Rb,YZae),(Caf,Rb,YZaf),(Caf,Rb,YZag),(Caf,Rc,YZa),(Caf,Rc,YZb),(Caf,Rc,YZc),(Caf,Rc,YZd),(Caf,Rc,YZe),(Caf,Rc,YZf),(Caf,Rc,YZg),(Caf,Rc,YZh),(Caf,Rc,YZi),(Caf,Rc,YZj),(Caf,Rc,YZk),(Caf,Rc,YZl),(Caf,Rc,YZm),(Caf,Rc,YZn),(Caf,Rc,YZo),(Caf,Rc,YZp),(Caf,Rc,YZq),(Caf,Rc,YZr),(Caf,Rc,YZs),(Caf,Rc,YZt),(Caf,Rc,YZu),(Caf,Rc,YZy),(Caf,Rc,YZw),(Caf,Rc,YZx),(Caf,Rc,YZy),(Caf,Rc,YZz),(Caf,Rc,YZaa),(Caf,Rc,YZab),(Caf,Rc,YZac),(Caf,Rc,YZad),(Caf,Rc,YZae),(Caf,Rc,YZaf),(Caf,Rc,YZag),(Caf,Rd,YZa),(Caf,Rd,YZb),(Caf,Rd,YZc),(Caf,Rd,YZd),(Caf,Rd,YZe),(Caf,Rd,YZf),(Caf,Rd,YZg),(Caf,Rd,YZh),(Caf,Rd,YZi),(Caf,Rd,YZj),(Caf,Rd,YZk),(Caf,Rd,YZl),(Caf,Rd,YZm),(Caf,Rd,YZn),(Caf,Rd,YZo),(Caf,Rd,YZp),(Caf,Rd,YZq),(Caf,Rd,YZr),(Caf,Rd,YZs),(Caf,Rd,YZt),(Caf,Rd,YZu),(Caf,Rd,YZv),(Caf,Rd,YZw),(Caf,Rd,YZx),(Caf,Rd,YZy),(Caf,Rd,YZz),(Caf,Rd,YZaa),(Caf,Rd,YZab),(Caf,Rd,YZac),(Caf,Rd,YZad),(Caf,Rd,YZae),(Caf,Rd,YZaf),(Caf,Rd,YZag),(Caf,Re,YZa),(Caf,Re,YZb),(Caf,Re,YZc),(Caf,Re,YZd),(Caf,Re,YZe),(Caf,Re,YZf),(Caf,Re,YZg),(Caf,Re,YZh),(Caf,Re,YZi),(Caf,Re,YZj),(Caf,Re,YZk),(Caf,Re,YZl),(Caf,Re,YZm),(Caf,Re,YZn),(Caf,Re,YZo),(Caf,Re,YZp),(Caf,Re,YZq),(Caf,Re,YZr),(Caf,Re,YZs),(Caf,Re,YZt),(Caf,Re,YZu),(Caf,Re,YZy),(Caf,Re,YZw),(Caf,Re,YZx),(Caf,Re,YZy),(Caf,Re,YZz),(Caf,Re,YZaa),(Caf,Re,YZab),(Caf,Re,YZac),(Caf,Re,YZad),(Caf,Re,YZae),(Caf,Re,YZaf),(Caf,Re,YZag),(Cag,Ra,YZa),(Cag,Ra,YZb),(Cag,Ra,YZc),(Cag,Ra,YZd),(Cag,Ra,YZe),(Cag,Ra,YZf),(Cag,Ra,YZg),(Cag,Ra,YZh),(Cag,Ra,YZi),(Cag,Ra,YZj),(Cag,Ra,YZk),(Cag,Ra,YZl),(Cag,Ra,YZm),(Cag,Ra,YZn),(Cag,Ra,YZo),(Cag,Ra,YZp),(Cag,Ra,YZq),(Cag,Ra,YZr),(Cag,Ra,YZs),(Cag,Ra,YZt),(Cag,Ra,YZu),(Cag,Ra,YZv),(Cag,Ra,YZw),(Cag,Ra,YZx),(Cag,Ra,YZy),(Cag,Ra,YZz),(Cag,Ra,YZaa),(Cag,Ra,YZab),(Cag,Ra,YZac),(Cag,Ra,YZad),(Cag,Ra,YZae),(Cag,Ra,YZaf),(Cag,Ra,YZag),(Cag,Rb,YZa),(Cag,Rb,YZb),(Cag,Rb,YZc),(Cag,Rb,YZd),(Cag,Rb,YZe),(Cag,Rb,YZf),(Cag,Rb,YZg),(Cag,Rb,YZh),(Cag,Rb,YZi),(Cag,Rb,YZj),(Cag,Rb,YZk),(Cag,Rb,YZl),(Cag,Rb,YZm),(Cag,Rb,YZn),(Cag,Rb,YZo),(Cag,Rb,YZp),(Cag,Rb,YZq),(Cag,Rb,YZr),(Cag,Rb,YZs),(Cag,Rb,YZt),(Cag,Rb,YZu),(Cag,Rb,YZv),(Cag,Rb,YZw),(Cag,Rb,YZx),(Cag,Rb,YZy),(Cag,Rb,YZz),(Cag,Rb,YZaa),(Cag,Rb,YZab),(Cag,Rb,YZac),(Cag,Rb,YZad),(Cag,Rb,YZae),(Cag,Rb,YZaf),(Cag,Rb,YZag),(Cag,Rc,YZa),(Cag,Rc,YZb),(Cag,Rc,YZc),(Cag,Rc,YZd),(Cag,Rc,YZe),(Cag,Rc,YZf),(Cag,Rc,YZg),(Cag,Rc,YZh),(Cag,Rc,YZi),(Cag,Rc,YZj),(Cag,Rc,YZk),(Cag,Rc,YZl),(Cag,Rc,YZm),(Cag,Rc,YZn),(Cag,Rc,YZo),(Cag,Rc,YZp),(Cag,Rc,YZq),(Cag,Rc,YZr),(Cag,Rc,YZs),(Cag,Rc,YZt),(Cag,Rc,YZu),(Cag,Rc,YZv),(Cag,Rc,YZw),(Cag,Rc,YZx),(Cag,Rc,YZy),(Cag,Rc,YZz),(Cag,Rc,YZaa),(Cag,Rc,YZab),(Cag,Rc,YZac),(Cag,Rc,YZad),(Cag,Rc,YZae),(Cag,Rc,YZaf),(Cag,Rc,YZag),(Cag,Rd,YZa),(Cag,Rd,YZb),(Cag,Rd,YZc),(Cag,Rd,YZd),(Cag,Rd,YZe),(Cag,Rd,YZf),(Cag,Rd,YZg),(Cag,Rd,YZh),(Cag,Rd,YZi),(Cag,Rd,YZj),(Cag,Rd,YZk),(Cag,Rd,YZl),(Cag,Rd,YZm),(Cag,Rd,YZn),(Cag,Rd,YZo),(Cag,Rd,YZp),(Cag,Rd,YZq),(Cag,Rd,YZr),(Cag,Rd,YZs),(Cag,Rd,YZt),(Cag,Rd,YZu),(Cag,Rd,YZv),(Cag,Rd,YZw),(Cag,Rd,YZx),(Cag,Rd,YZy),(Cag,Rd,YZz),(Cag,Rd,YZaa),(Cag,Rd,YZab),(Cag,Rd,YZac),(Cag,Rd,YZad),(Cag,Rd,YZae),(Cag,Rd,YZaf),(Cag,Rd,YZag),(Cag,Re,YZa),(Cag,Re,YZb),(Cag,Re,YZc),(Cag,Re,YZd),(Cag,Re,

YZe),(Cag,Re,YZf),(Cag,Re,YZg), (Cag,Re,YZh),(Cag,Re, YZi),(Cag,Re,YZj),(Cag,Re,YZk),(Cag,Re,YZl),(Cag,Re, YZm),(Cag,Re,YZn),(Cag,Re,YZo),(Cag,Re,YZp),(Cag, Re,YZq),(Cag,Re,YZr),(Cag,Re,YZs),(Cag,Re, YZt),(Cag, Re,YZu),(Cag,Re,YZv),(Cag,Re,YZw),(Cag,Re,YZx), (Cag,Re,YZy),(Cag,Re,YZ z) (Cag,Re,YZaa),(Cag,Re, YZab),(Cag,Re,YZac),(Cag,Re,YZad),(Cag,Re,YZae), (Cag,Re,Y Zaf),(Cag,Re,YZag),(Cah,Ra,YZa),(Cah,Ra, YZb),(Cah,Ra,YZc),(Cah,Ra,YZd),(Cah,Ra,YZe), (Cah,Ra, YZf),(Cah,Ra,YZg),(Cah,Ra,YZh),(Cah,Ra,YZi),(Cah,Ra, YZj),(Cah,Ra,YZk),(Ca h,Ra,YZl),(Cah,Ra,YZm),(Cah,Ra, YZn),(Cah,Ra,YZo),(Cah,Ra,YZp),(Cah,Ra,YZq),(Cah,R a,YZr),(Cah,Ra,YZs),(Cah,Ra,YZt),(Cah,Ra,YZu),(Cah, Ra,YZv),(Cah,Ra,YZw),(Cah,Ra,YZ x) (Cah,Ra,YZy), (Cah,Ra,YZz),(Cah,Ra,YZaa),(Cah,Ra,YZab),(Cah,Ra, YZac),(Cah,Ra,YZa d) (Cah,Ra,YZae),(Cah,Ra,YZaf), (Cah,Ra,YZag),(Cah,Rb,YZa),(Cah,Rb,YZb),(Cah,Rb, YZc, (Cah,Rb,YZd),(Cah,Rb,YZe),(Cah,Rb,YZf),(Cah,Rb, YZg),(Cah,Rb,YZh),(Cah,Rb,YZi),(C ah,Rb,YZj),(Cah,Rb, YZk),(Cah,Rb,YZl),(Cah,Rb,YZm),(Cah,Rb,YZn),(Cah, Rb,YZo),(Cah, Rb,YZp),(Cah,Rb,YZq),(Cah,Rb,YZr), (Cah,Rb,YZs),(Cah,Rb,YZt),(Cah,Rb,YZu),(Cah,Rb, YZy), (Cah,Rb,YZw),(Cah,Rb,YZx),(Cah,Rb,YZy),(Cah,Rb, YZz),(Cah,Rb,YZaa),(Cah,Rb,Y Zab),(Cah,Rb,YZac),(Cah, Rb,YZad),(Cah,Rb,YZae),(Cah,Rb,YZaf),(Cah,Rb,YZag), (Cah,Rc, YZa),(Cah,Rc,YZb),(Cah,Rc,YZc),(Cah,Rc,YZd), (Cah,Rc,YZe),(Cah,Rc,YZf),(Cah,Rc,YZg), (Cah,Rc,Ya), (Cah,Rc,YZi),(Cah,Rc,YZj),(Cah,Rc,YZk),(Cah,Rc,YZl), (Cah,Rc,YZm),(Ca h,Rc,YZn),(Cah,Rc,YZo),(Cah,Rc, YZp),(Cah,Rc,YZq),(Cah,Rc,YZr),(Cah,Rc,YZs),(Cah,Rc, YZt),(Cah,Rc,YZu),(Cah,Rc,YZv),(Cah,Rc,YZw),(Cah,Rc, YZx),(Cah,Rc,YZy),(Cah,Rc,YZ z) (Cah,Rc,YZaa),(Cah,R- c,YZab),(Cah,Rc,YZac),(Cah,Rc,YZad),(Cah,Rc,YZae), (Cah,Rc,Y Zaf),(Cah,Rc,YZag),(Cah,Rd,YZa),(Cah,Rd, YZb),(Cah,Rd,YZc),(Cah,Rd,YZd),(Cah,Rd,YZ e) (Cah, Rd,YZf),(Cah,Rd,YZg),(Cah,Rd,YZh),(Cah,Rd,YZi),(Cah, Rd,YZj),(Cah,Rd,YZk),(C ah,Rd,YZl),(Cah,Rd,YZm), (Cah,Rd,YZn),(Cah,Rd,YZo),(Cah,Rd,YZp),(Cah,Rd, YZq),(Cah, Rd,YZr),(Cah,Rd,YZs),(Cah,Rd,YZt),(Cah,Rd, YZu),(Cah,Rd,YZy),(Cah,Rd,YZw),(Cah,Rd, YZx),(Cah, Rd,YZy),(Cah,Rd,YZz),(Cah,Rd,YZaa),(Cah,Rd,YZab), (Cah,Rd,YZac),(Cah,Rd, YZad),(Cah,Rd,YZae),(Cah,Rd, YZaf),(Cah,Rd,YZag),(Cah,Re,YZa),(Cah,Re,YZb),(Cah, Re, YZc),(Cah,Re,YZd),(Cah,Re,YZe),(Cah,Re,YZf),(Cah, Re,YZg),(Cah,Re,YZh),(Cah,Re,YZi), (Cah,Re,YZj),(Cah, Re,YZk),(Cah,Re,YZl),(Cah,Re,YZm),(Cah,Re,YZn),(Cah, Re,YZo),(Ca h,Re,YZp),(Cah,Re,YZq),(Cah,Re,YZr),(Cah, Re,YZs),(Cah,Re,YZt),(Cah,Re,YZu),(Cah,Re, YZv),(Cah, Re,YZw),(Cah,Re,YZx),(Cah,Re,YZy),(Cah,Re,YZz), (Cah,Re,YZaa),(Cah,Re,Y Zab),(Cah,Re,YZac),(Cah,Re, YZad),(Cah,Re,YZae),(Cah,Re,YZaf),(Cah,Re,YZag),(Cai, Ra, YZa),(Cai,Ra,YZb),(Cai,Ra,YZc),(Cai,Ra,YZd),(Cai, Ra,YZe),(Cai,Ra,YZf),(Cai,Ra,YZg),(C ai,Ra,YZh),(Cai, Ra,YZi),(Cai,Ra,YZj),(Cai,Ra,YZk),(Cai,Ra,YZl),(Cai,Ra, YZm),(Cai,Ra,Y Zn),(Cai,Ra,YZo),(Cai,Ra,YZp),(Cai,Ra, YZq),(Cai,Ra,YZr),(Cai,Ra,YZs),(Cai,Ra,YZt),(Cai, Ra,YZu),(Cai,Ra,YZy),(Cai,Ra,YZw),(Cai,Ra,YZx),(Cai, Ra,YZy),(Cai,Ra,YZz),(Cai,Ra,YZ aa),(Cai,Ra,YZab),(Cai, Ra,YZac),(Cai,Ra,YZad),(Cai,Ra,YZae),(Cai,Ra,YZaf), (Cai,Ra,YZa g) (Cai,Rb,YZa),(Cai,Rb,YZb),(Cai,Rb,YZc), (Cai,Rb,YZd),(Cai,Rb,YZe),(Cai,Rb,YZf),(Cai, Rb,YZg), (Cai,Rb,YZh),(Cai,Rb,YZi),(Cai,Rb,YZj),(Cai,Rb,YZk), (Cai,Rb,YZl),(Cai,Rb,YZ m) (Cai,Rb,YZn),(Cai,Rb,YZo), (Cai,Rb,YZp),(Cai,Rb,YZq),(Cai,Rb,YZr),(Cai,Rb,YZs), (Ca i,Rb,YZt),(Cai,Rb,YZu),(Cai,Rb,YZy),(Cai,Rb,YZw), (Cai,Rb,YZx),(Cai,Rb,YZy),(Cai,Rb,Y Zz),(Cai,Rb,YZaa), (Cai,Rb,YZab),(Cai,Rb,YZac),(Cai,Rb,YZad),(Cai,Rb,

YZae),(Cai,Rb,YZ af),(Cai,Rb,YZag),(Cai,Rc,YZa),(Cai, Rc,YZb),(Cai,Rc,YZc),(Cai,Rc,YZd),(Cai,Rc,YZe),(C ai,Rc,YZf),(Cai,Rc,YZg),(Cai,Rc,Ya),(Cai,Rc,YZi),(Cai, Rc,YZj),(Cai,Rc,YZk),(Cai,Rc,YZl), (Cai,Rc,YZm),(Cai,R- c,YZn),(Cai,Rc,YZo),(Cai,Rc,YZp),(Cai,Rc,YZq),(Cai,Rc, YZr),(Cai, Rc,YZs),(Cai,Rc,YZt),(Cai,Rc,YZu),(Cai,Rc, YZy),(Cai,Rc,YZw),(Cai,Rc,YZx),(Cai,Rc,YZy), (Cai,Rc, YZz),(Cai,Rc,YZaa),(Cai,Rc,YZab),(Cai,Rc,YZac),(Cai, Rc,YZad),(Cai,Rc,YZae), (Cai,Rc,YZaf),(Cai,Rc,YZag), (Cai,Rd,YZa),(Cai,Rd,YZb),(Cai,Rd,YZc),(Cai,Rd,YZd), (Cai, Rd,YZe),(Cai,Rd,YZf),(Cai,Rd,YZg),(Cai,Rd,YZh), (Cai,Rd,YZi),(Cai,Rd,YZj),(Cai,Rd,YZk), (Cai,Rd,YZl), (Cai,Rd,YZm),(Cai,Rd,YZn),(Cai,Rd,YZo),(Cai,Rd,YZp), (Cai,Rd,YZq),(Cai, Rd,YZr),(Cai,Rd,YZs),(Cai,Rd,YZt), (Cai,Rd,YZu),(Cai,Rd,YZy),(Cai,Rd,YZw),(Cai,Rd,YZ x) (Cai,Rd,YZy),(Cai,Rd,YZz),(Cai,Rd,YZaa),(Cai,Rd,YZab), (Cai,Rd,YZac),(Cai,Rd,YZad), (Cai,Rd,YZae),(Cai,Rd,YZ- af),(Cai,Rd,YZag),(Cai,Re,YZa),(Cai,Re,YZb),(Cai,Re, YZc),(Cai, Re,YZd),(Cai,Re,YZe),(Cai,Re,YZf),(Cai,Re, YZg),(Cai,Re,YZh),(Cai,Re,YZi),(Cai,Re,YZj), (Cai,Re, YZk),(Cai,Re,YZl),(Cai,Re,YZm),(Cai,Re,YZn),(Cai,Re, YZo),(Cai,Re,YZp),(Cai,R e,YZq),(Cai,Re,YZr),(Cai,Re, YZs),(Cai,Re,YZt),(Cai,Re,YZu),(Cai,Re,YZy),(Cai,Re, YZw), (Cai,Re,YZx),(Cai,Re,YZy),(Cai,Re,YZz),(Cai,Re, YZaa),(Cai,Re,YZab),(Cai,Re,YZac),(Cai, Re,YZad),(Cai, Re,YZae),(Cai,Re,YZaf),(Cai,Re,YZag),(Caj,Ra,YZa), (Caj,Ra,YZb),(Caj,Ra, YZc),(Caj,Ra,YZd),(Caj,Ra,YZe), (Caj,Ra,YZf),(Caj,Ra,YZg),(Caj,Ra,YZh),(Caj,Ra,YZi),(C aj,Ra,YZj),(Caj,Ra,YZk),(Caj,Ra,YZl),(Caj,Ra,YZm),(Caj, Ra,YZn),(Caj,Ra,YZo),(Caj,Ra,Y Zp),(Caj,Ra,YZq),(Caj, Ra,YZr),(Caj,Ra,YZs),(Caj,Ra,YZt),(Caj,Ra,YZu),(Caj,Ra, YZv),(Caj, Ra,YZw),(Caj,Ra,YZx),(Caj,Ra,YZy),(Caj,Ra, YZz),(Caj,Ra,YZaa),(Caj,Ra,YZab),(Caj,Ra, YZac),(Caj, Ra,YZad),(Caj,Ra,YZae),(Caj,Ra,YZaf),(Caj,Ra,YZag), (Caj,Rb,YZa),(Caj,Rb,Y Zb),(Caj,Rb,YZc),(Caj,Rb,Yal), (Caj,Rb,YZe),(Caj,Rb,YZf),(Caj,Rb,YZg),(Caj,Rb,YZh),(C aj,Rb,YZi),(Caj,Rb,YZj),(Caj,Rb,YZk),(Caj,Rb,YZl),(Caj, Rb,YZm),(Caj,Rb,YZn),(Caj,Rb,Y Zo),(Caj,Rb,YZp),(Caj, Rb,YZq),(Caj,Rb,YZr),(Caj,Rb,YZs),(Caj,Rb,YZt),(Caj, Rb,YZu),(Ca j,Rb,YZy),(Caj,Rb,YZw),(Caj,Rb,YZx),(Caj, Rb,YZy),(Caj,Rb,YZz),(Caj,Rb,YZaa),(Caj,Rb, YZab), (Caj,Rb,YZac),(Caj,Rb,YZad),(Caj,Rb,YZae),(Caj,Rb, YZaf),(Caj,Rb,YZag),(Caj,Rc, YZa),(Caj,Rc,YZb),(Caj,Rc, YZc),(Caj,Rc,YZd),(Caj,Rc,YZe),(Caj,Rc,YZf),(Caj,Rc, YZg),(C aj,Rc,YZh),(Caj,Rc,YZi),(Caj,Rc,YZj),(Caj,Rc, YZk),(Caj,Rc,YZl),(Caj,Rc,YZm),(Caj,Rc,Y Zn),(Caj,Rc, YZo),(Caj,Rc,YZp),(Caj,Rc,YZq),(Caj,Rc,YZr),(Caj,Rc, YZs),(Caj,Rc,YZt),(Caj, Rc,YZu),(Caj,Rc,YZv),(Caj,Rc, YZw),(Caj,Rc,YZx),(Caj,Rc,YZy),(Caj,Rc,YZz),(Caj,Rc, YZ aa),(Caj,Rc,YZab),(Caj,Rc,YZac),(Caj,Rc,YZad),(Caj, Rc,YZae),(Caj,Rc,YZaf),(Caj,Rc,YZa g) (Caj,Rd,YZa), (Caj,Rd,YZb),(Caj,Rd,YZc),(Caj,Rd,YZd),(Caj,Rd,YZe), (Caj,Rd,YZf),(Caj, Rd,YZg),(Caj,Rd,Ya),(Caj,Rd,YZi), (Caj,Rd,YZj),(Caj,Rd,YZk),(Caj,Rd,YZl),(Caj,Rd,YZ m) (Caj,Rd,YZn),(Caj,Rd,YZo),(Caj,Rd,YZp),(Caj,Rd,YZq), (Caj,Rd,YZr),(Caj,Rd,YZs),(Ca j,Rd,YZt),(Caj,Rd,YZu), (Caj,Rd,YZy),(Caj,Rd,YZw),(Caj,Rd,YZx),(Caj,Rd,YZy), (Caj,Rd,Y Zz),(Caj,Rd,YZaa),(Caj,Rd,YZab),(Caj,Rd, YZac),(Caj,Rd,YZad),(Caj,Rd,YZae),(Caj,Rd,YZ af),(Caj, Rd,YZag),(Caj,Re,YZa),(Caj,Re,YZb),(Caj,Re,YZc),(Caj, Re,YZd),(Caj,Re,YZe),(C aj,Re,YZf),(Caj,Re,YZg),(Caj, Re,Ya),(Caj,Re,YZi),(Caj,Re,YZj),(Caj,Re,YZk),(Caj,Re, YZl), (Caj,Re,YZm),(Caj,Re,YZn),(Caj,Re,YZo),(Caj,Re, YZp),(Caj,Re,YZq),(Caj,Re,YZr),(Caj, Re,YZs),(Caj,Re, YZt),(Caj,Re,YZu),(Caj,Re,YZy),(Caj,Re,YZw),(Caj,Re, YZx),(Caj,Re,YZy), (Caj,Re,YZz),(Caj,Re,YZaa),(Caj,Re, YZab),(Caj,Re,YZac),(Caj,Re,YZad),(Caj,Re,YZae), (Caj,

Re,YZaf),(Caj,Re,YZag),(Cak,Ra,YZa),(Cak,Ra,YZb), (Cak,Ra,YZc),(Cak,Ra,YZd),(Cak, Ra,YZe),(Cak,Ra,YZf), (Cak,Ra,YZg),(Cak,Ra,YZh),(Cak,Ra,YZi),(Cak,Ra,YZj), (Cak,Ra,Y Th),(Cak,Ra,YZl),(Cak,Ra,YZm),(Cak,Ra, YZn),(Cak,Ra,YZo),(Cak,Ra,YZp),(Cak,Ra,YZq), (Cak, Ra,YZr),(Cak,Ra,YZs),(Cak,Ra,YZt),(Cak,Ra,YZu),(Cak, Ra,YZy),(Cak,Ra,YZw),(Cak, Ra,YZx),(Cak,Ra,YZy), (Cak,Ra,YZz),(Cak,Ra,YZaa),(Cak,Ra,YZab),(Cak,Ra, YZac),(Cak, Ra,YZad),(Cak,Ra,YZae),(Cak,Ra,YZaf), (Cak,Ra,YZag),(Cak,Rb,YZa),(Cak,Rb,YZb),(Cak, Rb,YZc),(Cak,Rb,YZd),(Cak,Rb,YZe),(Cak,Rb,YZf),(Cak, Rb,YZg),(Cak,Rb,YZh),(Cak,Rb, YZi),(Cak,Rb,YZj),(Cak, Rb,YZk),(Cak,Rb,YZl),(Cak,Rb,YZm),(Cak,Rb,YZn), (Cak,Rb,YZo), (Cak,Rb,YZp),(Cak,Rb,YZq),(Cak,Rb, YZr),(Cak,Rb,YZs),(Cak,Rb,YZt),(Cak,Rb,YZu),(C ak,Rb, YZv),(Cak,Rb,YZw),(Cak,Rb,YZx),(Cak,Rb,YZy),(Cak, Rb,YZz),(Cak,Rb,YZaa),(Ca k,Rb,YZab),(Cak,Rb,YZac), (Cak,Rb,YZad),(Cak,Rb,YZae),(Cak,Rb,YZaf),(Cak,Rb, YZag), (Cak,Rc,YZa),(Cak,Rc,YZb),(Cak,Rc,YZc),(Cak, Rc,YZd),(Cak,Rc,YZe),(Cak,Rc,YZf),(Cak, Rc,YZg),(Cak, Rc,YZh),(Cak,Rc,YZi),(Cak,Rc,YZj),(Cak,Rc,YZl),(Cak, Rc,YZl),(Cak,Rc,Y Zm),(Cak,Rc,YZn),(Cak,Rc,YZo), (Cak,Rc,YZp),(Cak,Rc,YZq),(Cak,Rc,YZr),(Cak,Rc,YZs), (Cak,Rc,YZt),(Cak,Rc,YZu),(Cak,Rc,YZy),(Cak,Rc,YZw), (Cak,Rc,YZx),(Cak,Rc,YZy),(Ca k,Rc,YZz),(Cak,Rc, YZaa),(Cak,Rc,YZab),(Cak,Rc,YZac),(Cak,Rc,YZad), (Cak,Rc,YZae),(C ak,Rc,YZaf),(Cak,Rc,YZag),(Cak,Rd, YZa),(Cak,Rd,YZb),(Cak,Rd,YZc),(Cak,Rd,YZd),(Cak, Rd,YZe),(Cak,Rd,YZf),(Cak,Rd,YZg),(Cak,Rd,YZh),(Cak, Rd,YZi),(Cak,Rd,YZj),(Cak,Rd, YZk),(Cak,Rd,YZl),(Cak, Rd,YZm),(Cak,Rd,YZn),(Cak,Rd,YZo),(Cak,Rd,YZp), (Cak,Rd,YZ q) (Cak,Rd,YZr),(Cak,Rd,YZs),(Cak,Rd,YZt), (Cak,Rd,YZu),(Cak,Rd,YZy),(Cak,Rd,YZw), (Cak,Rd, YZx),(Cak,Rd,YZy),(Cak,Rd,YZz),(Cak,Rd,YZaa),(Cak, Rd,YZab),(Cak,Rd,YZac), (Cak,Rd,YZad),(Cak,Rd,YZae), (Cak,Rd,YZaf),(Cak,Rd,YZag),(Cak,Re,YZa),(Cak,Re, YZb), (Cak,Re,YZc),(Cak,Re,YZd),(Cak,Re,YZe),(Cak,Re, YZf),(Cak,Re,YZg),(Cak,Re,Ya),(Cak, Re,YZi),(Cak,Re, YZj),(Cak,Re,YZk),(Cak,Re,YZl),(Cak,Re,YZm),(Cak,Re, YZn),(Cak,Re,Y Zo),(Cak,Re,YZp),(Cak,Re,YZq),(Cak, Re,YZr),(Cak,Re,YZs),(Cak,Re,YZt),(Cak,Re,YZu), (Cak, Re,YZv),(Cak,Re,YZw),(Cak,Re,YZx),(Cak,Re,YZy), (Cak,Re,YZz),(Cak,Re,YZaa),(Ca k,Re,YZab),(Cak,Re, YZac),(Cak,Re,YZad),(Cak,Re,YZae),(Cak,Re,YZaf), (Cak,Re,YZag), (Cal,Ra,YZa),(Cal,Ra,YZb),(Cal,Ra,YZc), (Cal,Ra,YZd),(Cal,Ra,YZe),(Cal,Ra,YZf),(Cal,Ra, YZg), (Cal,Ra,YZh),(Cal,Ra,YZi),(Cal,Ra,YZj),(Cal,Ra,YZk), (Cal,Ra,YZl),(Cal,Ra,YZm),(C al, Ra,YZn),(Cal,Ra,YZo), (Cal,Ra,YZp),(Cal,Ra,YZq),(Cal,Ra,YZr),(Cal,Ra,YZs), (Cal,Ra,Y Zt),(Cal,Ra,YZu),(Cal,Ra,YZy),(Cal,Ra,YZw), (Cal,Ra,YZx),(Cal,Ra,YZy),(Cal,Ra,YZz),(Ca l,Ra,YZaa), (Cal,Ra,YZab),(Cal,Ra,YZac),(Cal,Ra,YZad),(Cal,Ra, YZae),(Cal,Ra,YZaf),(Cal, Ra,YZag),(Cal,Rb,YZa),(Cal, Rb,YZb),(Cal,Rb,YZc),(Cal,Rb,YZd),(Cal,Rb,YZe),(Cal, Rb,Y Zf),(Cal,Rb,YZg),(Cal,Rb,YZl),(Cal,Rb,YZi),(Cal, Rb,YZj),(Cal,Rb,YZk),(Cal,Rb,YZl),(Cal, Rb,YZm),(Cal, Rb,YZn),(Cal,Rb,YZo),(Cal,Rb,YZp),(Cal,Rb,YZq),(Cal, Rb,YZr),(Cal,Rb,Y Zs),(Cal,Rb,YZt),(Cal,Rb,YZu),(Cal, Rb,YZy),(Cal,Rb,YZw),(Cal,Rb,YZx),(Cal,Rb,YZy),(C al, Rb,YZz),(Cal,Rb,YZaa),(Cal,Rb,YZab),(Cal,Rb,YZac), (Cal,Rb,YZad),(Cal,Rb,YZae),(Cal, Rb,YZaf),(Cal,Rb, YZag),(Cal,Rc,YZa),(Cal,Rc,YZb),(Cal,Rc,YZc),(Cal,Rc, YZd),(Cal,Rc,Y Ze),(Cal,Rc,YZf),(Cal,Rc,YZg),(Cal,Rc, YZh),(Cal,Rc,YZi),(Cal,Rc,YZj),(Cal,Rc,YZk),(Cal, Rc,YZl),(Cal,Rc,YZm),(Cal,Rc,YZn),(Cal,Rc,YZo),(Cal, Rc,YZp),(Cal,Rc,YZq),(Cal,Rc,YZr), (Cal,Rc,YZs),(Cal,R- c,YZt),(Cal,Rc,YZu),(Cal,Rc,YZy),(Cal,Rc,YZw),(Cal,Rc, YZx),(Cal,R c,YZy),(Cal,Rc,YZz),(Cal,Rc,YZaa),(Cal,Rc, YZab),(Cal,Rc,YZac),(Cal,Rc,YZad),(Cal,Rc,Y Zae),(Cal, Rc,YZaf),(Cal,Rc,YZag),(Cal,Rd,YZa),(Cal,Rd,YZb),(Cal, Rd,YZc),(Cal,Rd,YZd), (Cal,Rd,YZe),(Cal,Rd,YZf),(Cal, Rd,YZg),(Cal,Rd,YZh),(Cal,Rd,YZi),(Cal,Rd,YZj),(Cal, Rd,Ya),(Cal,Rd,YZl),(Cal,Rd,YZm),(Cal,Rd,YZn),(Cal,Rd, YZo),(Cal,Rd,YZp),(Cal,Rd,YZq), (Cal,Rd,YZr),(Cal,Rd, YZs),(Cal,Rd,YZt),(Cal,Rd,YZu),(Cal,Rd,YZy),(Cal,Rd, YZw),(Cal,R d,YZx),(Cal,Rd,YZy),(Cal,Rd,YZz),(Cal,Rd, YZaa),(Cal,Rd,YZab),(Cal,Rd,YZac),(Cal,Rd,Y Zad),(Cal, Rd,YZae),(Cal,Rd,YZaf),(Cal,Rd,YZag),(Cal,Re,YZa), (Cal,Re,YZb),(Cal,Re,YZc), (Cal,Re,YZd),(Cal,Re,YZe), (Cal,Re,YZf),(Cal,Re,YZg),(Cal,Re,YZh),(Cal,Re,YZi), (Cal,Re, YZj),(Cal,Re,YZk),(Cal,Re,YZl),(Cal,Re,YZm), (Cal,Re,YZn),(Cal,Re,YZo),(Cal,Re,YZp), (Cal,Re,YZq), (Cal,Re,YZr),(Cal,Re,YZs),(Cal,Re,YZt),(Cal,Re,YZu), (Cal,Re,YZv),(Cal,Re, YZw),(Cal,Re,YZx),(Cal,Re,YZy), (Cal,Re,YZz),(Cal,Re,YZaa),(Cal,Re,YZab),(Cal,Re,YZa c) (Cal,Re,YZad),(Cal,Re,YZae),(Cal,Re,YZaf),(Cal,Re, YZag),(Cam,Ra,YZa),(Cam,Ra,YZb), (Cam,Ra,YZc), (Cam,Ra,YZd),(Cam,Ra,YZe),(Cam,Ra,YZf),(Cam,Ra, YZg),(Cam,Ra,YZh), (Cam,Ra,YZi),(Cam,Ra,YZj),(Cam, Ra,YZk),(Cam,Ra,YZl),(Cam,Ra,YZm),(Cam,Ra,YZn), (Cam,Ra,YZo),(Cam,Ra,YZp),(Cam,Ra,YZq),(Cam,Ra, YZr),(Cam,Ra,YZs),(Cam,Ra,YZt), (Cam,Ra,YZu),(Cam, Ra,YZy),(Cam,Ra,YZw),(Cam,Ra,YZx),(Cam,Ra,YZy), (Cam,Ra,YZz), (Cam,Ra,YZaa),(Cam,Ra,YZab),(Cam,Ra, YZac),(Cam,Ra,YZad),(Cam,Ra,YZae),(Cam,Ra, YZaf), (Cam,Ra,YZag),(Cam,Rb,YZa),(Cam,Rb,YZb),(Cam,Rb, YZc),(Cam,Rb,YZd),(Cam, Rb,YZe),(Cam,Rb,YZf),(Cam, Rb,YZg),(Cam,Rb,YZh),(Cam,Rb,YZi),(Cam,Rb,YZj), (Cam, Rb,YZk),(Cam,Rb,YZl),(Cam,Rb,YZm),(Cam,Rb, YZn),(Cam,Rb,YZo),(Cam,Rb,YZp),(Ca m,Rb,YZq),(Cam, Rb,YZr),(Cam,Rb,YZs),(Cam,Rb,YZt),(Cam,Rb,YZu), (Cam,Rb,YZy),(Ca m,Rb,YZw),(Cam,Rb,YZx),(Cam,Rb, YZy),(Cam,Rb,YZz),(Cam,Rb,YZaa),(Cam,Rb,YZab), (Cam,Rb,YZac),(Cam,Rb,YZad),(Cam,Rb,YZae),(Cam, Rb,YZaf),(Cam,Rb,YZag),(Cam,Rc, YZa),(Cam,Rc,YZb), (Cam,Rc,YZc),(Cam,Rc,YZd),(Cam,Rc,YZe),(Cam,Rc, YZf),(Cam,Rc, YZg),(Cam,Rc,YZh),(Cam,Rc,YZi),(Cam, Rc,YZj),(Cam,Rc,YZk),(Cam,Rc,YZl),(Cam,Rc,Y Zm), (Cam,Rc,YZn),(Cam,Rc,YZo),(Cam,Rc,YZp),(Cam,Rc, YZq),(Cam,Rc,YZr),(Cam,Rc,Y Zs),(Cam,Rc,YZt),(Cam, Rc,YZu),(Cam,Rc,YZy),(Cam,Rc,YZw),(Cam,Rc,YZx), (Cam,Rc,Y Zy),(Cam,Rc,YZz),(Cam,Rc,YZaa),(Cam,Rc, YZab),(Cam,Rc,YZac),(Cam,Rc,YZad),(Cam, Rc,YZae), (Cam,Rc,YZaf),(Cam,Rc,YZag),(Cam,Rd,YZa),(Cam,Rd, YZb),(Cam,Rd,YZc),(C am,Rd,YZd),(Cam,Rd,YZe),(Cam, Rd,YZf),(Cam,Rd,YZg),(Cam,Rd,YZh),(Cam,Rd,YZi),(C am,Rd,YZj),(Cam,Rd,YZk),(Cam,Rd,YZl),(Cam,Rd, YZm),(Cam,Rd,YZn),(Cam,Rd,YZo), (Cam,Rd,YZp), (Cam,Rd,YZq),(Cam,Rd,YZr),(Cam,Rd,YZs),(Cam,Rd, YZt),(Cam,Rd,YZu), (Cam,Rd,YZv),(Cam,Rd,YZw),(Cam, Rd,YZx),(Cam,Rd,YZy),(Cam,Rd,YZz),(Cam,Rd,YZaa), (Cam,Rd,YZab),(Cam,Rd,YZac),(Cam,Rd,YZad),(Cam, Rd,YZae),(Cam,Rd,YZaf),(Cam,R d,YZag),(Cam,Re,YZa), (Cam,Re,YZb),(Cam,Re,YZc),(Cam,Re,YZd),(Cam,Re, YZe),(Cam, Re,YZf),(Cam,Re,YZg),(Cam,Re,YZh),(Cam, Re,YZi),(Cam,Re,YZj),(Cam,Re,YZk),(Cam,R e,YZl), (Cam,Re,YZm),(Cam,Re,YZn),(Cam,Re,YZo),(Cam,Re, YZp),(Cam,Re,YZq),(Cam,R e,YZr),(Cam,Re,YZs),(Cam, Re,YZt),(Cam,Re,YZu),(Cam,Re,YZy),(Cam,Re,YZw), (Cam,R e,YZx),(Cam,Re,YZy),(Cam,Re,YZz),(Cam,Re, YZaa),(Cam,Re,YZab),(Cam,Re,YZac),(Ca m,Re,YZad), (Cam,Re,YZae),(Cam,Re,YZaf),(Cam,Re,YZag),(Can,Ra, YZa),(Can,Ra,YZb), (Can,Ra,YZc),(Can,Ra,YZd),(Can,Ra, YZe),(Can,Ra,YZf),(Can,Ra,YZg),(Can,Ra,YZh),(Can,

Ra,YZi),(Can,Ra,YZj),(Can,Ra,YZk),(Can,Ra,YZl),(Can,Ra,YZm),(Can,Ra,YZn),(Can,Ra,YZo),(Can,Ra,YZp),(Can,Ra,YZq),(Can,Ra,YZr),(Can,Ra,YZs),(Can,Ra,YZt),(Can,Ra,YZu), (Can,Ra,YZv),(Can,Ra,YZw),(Can,Ra,YZx),(Can,Ra,YZy),(Can,Ra,YZz),(Can,Ra,YZaa),(Can,Ra,YZab),(Can,Ra,YZac),(Can,Ra,YZad),(Can,Ra,YZae),(Can,Ra,YZaf),(Can,Ra,YZag), (Can,Rb,YZa),(Can,Rb,YZb),(Can,Rb,YZc),(Can,Rb,YZd),(Can,Rb,YZe),(Can,Rb,YZf),(Can,Rb,YZg),(Can,Rb,YZh),(Can,Rb,YZi),(Can,Rb,YZj),(Can,Rb,YZk),(Can,Rb,YZl),(Can,Rb,YZm),(Can,Rb,YZn),(Can,Rb,YZo),(Can,Rb,YZp),(Can,Rb,YZq),(Can,Rb,YZr),(Can,Rb,YZs) (Can,Rb,YZt),(Can,Rb,YZu),(Can,Rb,YZy),(Can,Rb,YZw),(Can,Rb,YZx),(Can,Rb,YZy), (Can,Rb,YZz),(Can,Rb,YZaa),(Can,Rb,YZab),(Can,Rb,YZac),(Can,Rb,YZad),(Can,Rb,YZae), (Can,Rb,YZaf),(Can,Rb,YZag),(Can,Rc,YZa),(Can,Rc,YZb),(Can,Rc,YZc),(Can,Rc,YZd), (Can,Rc,YZe),(Can,Rc,YZf),(Can,Rc,YZg),(Can,Rc,YZh),(Can,Rc,YZi),(Can,Rc,YZj),(Can,Rc,YZk),(Can,Rc,YZl),(Can,Rc,YZm),(Can,Rc,YZn),(Can,Rc,YZo),(Can,Rc,YZp),(Can,Rc, YZq),(Can,Rc,YZr),(Can,Rc,YZs),(Can,Rc,YZt),(Can,Rc,YZu),(Can,Rc,YZy),(Can,Rc,YZw), (Can,Rc,YZx),(Can,Rc,YZy),(Can,Rc,YZz),(Can,Rc,YZaa),(Can,Rc,YZab),(Can,Rc,YZac), (Can,Rc,YZad),(Can,Rc,YZae),(Can,Rc,YZaf),(Can,Rc,YZag),(Can,Rd,YZa),(Can,Rd,YZb), (Can,Rd,YZc),(Can,Rd,YZd),(Can,Rd,YZe),(Can,Rd,YZf),(Can,Rd,YZg),(Can,Rd,YZh),(Can,Rd,YZi),(Can,Rd,YZj),(Can,Rd,YZk),(Can,Rd,YZl),(Can,Rd,YZm),(Can,Rd,YZn),(Can,Rd,YZo),(Can,Rd,YZp),(Can,Rd,YZq),(Can,Rd,YZr),(Can,Rd,YZs),(Can,Rd,YZt),(Can,Rd,YZu),(Can,Rd,YZy),(Can,Rd,YZw), (Can,Rd,YZx),(Can,Rd,YZy),(Can,Rd,YZz),(Can,Rd,YZaa) (Can,Rd,YZab),(Can,Rd,YZac),(Can,Rd,YZad),(Can,Rd,YZae),(Can,Rd,YZaf),(Can,Rd,YZag),(Can,Re,YZa),(Can,Re,YZb),(Can,Re,YZc),(Can,Re,YZd),(Can,Re,YZe),(Can,Re,YZD, (Can,Re,YZg),(Can,Re,YZh),(Can,Re,YZi),(Can,Re,YZj),(Can,Re,YZk),(Can,Re,YZl),(Can, Re,YZm),(Can,Re,YZn),(Can,Re,YZo),(Can,Re,YZp),(Can,Re,YZq),(Can,Re,YZr),(Can,Re, YZs),(Can,Re,YZt),(Can,Re,YZu),(Can,Re,YZy),(Can,Re,YZw),(Can,Re,YZx),(Can,Re,YZy), (Can,Re,YZz),(Can,Re,YZaa),(Can,Re,YZab),(Can,Re,YZac),(Can,Re,YZad),(Can,Re,YZae),(Can,Re,YZaf), (Can,Re,YZag),(Cao,Ra,YZa),(Cao,Ra,YZb),(Cao,Ra,YZc),(Cao,Ra,YZd), (Cao,Ra,YZe),(Cao,Ra,YZf),(Cao,Ra,YZg),(Cao,Ra,YZh),(Cao,Ra,YZi),(Cao,Ra,YZj),(Cao,Ra,YZk),(Cao,Ra,YZl),(Cao,Ra,YZm),(Cao,Ra,YZn),(Cao,Ra,YZo),(Cao,Ra,YZp),(Cao,Ra, YZq),(Cao,Ra,YZr),(Cao,Ra,YZs),(Cao,Ra,YZt),(Cao,Ra,YZu),(Cao,Ra,YZy),(Cao,Ra,YZw), (Cao,Ra,YZx),(Cao,Ra,YZy),(Cao,Ra,YZz),(Cao,Ra,YZaa),(Cao,Ra,YZab),(Cao,Ra,YZac), (Cao,Ra,YZad),(Cao,Ra,YZae),(Cao,Ra,YZaf),(Cao,Ra,YZag), (Cao,Rb,YZa),(Cao,Rb,YZb), (Cao,Rb,YZc),(Cao,Rb,YZd),(Cao,Rb,YZe),(Cao,Rb,YZf),(Cao,Rb,YZg),(Cao,Rb,YZh),(Cao,Rb,YZi),(Cao,Rb,YZj),(Cao,Rb,YZk),(Cao,Rb,YZl),(Cao,Rb,YZm),(Cao,Rb,YZn),(Cao,Rb,YZo),(Cao,Rb,YZp),(Cao,Rb,YZq),(Cao,Rb,YZr),(Cao,Rb,YZs),(Cao,Rb,YZt),(Cao,Rb,YZu),(Cao,Rb,YZy),(Cao,Rb,YZw),(Cao,Rb,YZx),(Cao,Rb,YZy),(Cao,Rb,YZz),(Cao,Rb,YZaa) (Cao,Rb,YZab),(Cao,Rb,YZac),(Cao,Rb,YZad),(Cao,Rb,YZae),(Cao,Rb,YZaf),(Cao,Rb,YZag),(Cao,Rc,YZa),(Cao,Rc,YZb),(Cao,Rc,YZc),(Cao,Rc,YZd),(Cao,Rc,YZe),(Cao,Rc,YZf), (Cao,Rc,YZg),(Cao,Rc,YZh),(Cao,Rc,YZi),(Cao,Rc,YZj),(Cao,Rc,YZk),(Cao,Rc,YZl),(Cao, Rc,YZm),(Cao,Rc,YZn),(Cao,Rc,YZo),(Cao,Rc,YZp),(Cao,Rc,YZq),(Cao,Rc,YZr),(Cao,Rc,YZs),(Cao,Rc,YZt),(Cao,Rc,YZu),(Cao,Rc,YZy),(Cao,Rc,YZw),(Cao,Rc,YZx),(Cao,Rc,YZy), (Cao,Rc,YZz),(Cao,Rc,YZaa),(Cao,Rc,YZab),(Cao,Rc,YZac),(Cao,Rc,YZad),(Cao,Rc,YZae),(Cao,Rc,YZaf),(Cao,Rc,YZag),(Cao,Rd,YZa),(Cao,Rd,YZb),(Cao,Rd,YZc), (Cao,Rd,YaI), (Cao,Rd,YZe),(Cao,Rd,YZf),(Cao,Rd,YZg), (Cao,Rd,YZh),(Cao,Rd,YZi),(Cao,Rd,YZj),(Cao,Rd,YZk), (Cao,Rd,YZl),(Cao,Rd,YZm),(Cao,Rd,YZn),(Cao,Rd, YZo),(Cao,Rd,YZp),(Cao, Rd,YZq),(Cao,Rd,YZr),(Cao,Rd,YZs),(Cao,Rd,YZt),(Cao,Rd,YZu),(Cao,Rd,YZy),(Cao,Rd, YZw),(Cao,Rd,YZx),(Cao,Rd,YZy),(Cao,Rd,YZz), (Cao,Rd,YZaa),(Cao,Rd,YZab),(Cao,Rd, YZac),(Cao,Rd,YZad),(Cao,Rd,YZae),(Cao,Rd,YZaf),(Cao,Rd,YZag), (Cao,Re,YZa),(Cao,Re,YZb),(Cao,Re,YZc),(Cao,Re,YZd), (Cao,Re,YZe),(Cao,Re,YZf),(Cao,Re,YZg),(Cao,Re,YZh) (Cao,Re,YZi),(Cao,Re,YZj),(Cao,Re,YZk),(Cao,Re,YZl), (Cao,Re,YZm),(Cao,Re,YZn),(Cao,Re,YZo),(Cao,Re, YZp),(Cao,Re,YZq),(Cao,Re,YZr),(Cao,Re,YZs),(Cao,Re, YZt),(Cao,Re,YZu),(Cao,Re,YZv),(Cao,Re,YZw),(Cao, Re,YZx),(Cao,Re,YZy),(Cao,Re,YZz),(Cao,Re,Y Zaa), (Cao,Re,YZab),(Cao,Re,YZac),(Cao,Re,YZad),(Cao,Re, YZae),(Cao,Re,YZaf),(Cao,Re, YZag),(Cap,Ra,YZa),(Cap, Ra,YZb),(Cap,Ra,YZc),(Cap,Ra,YZd),(Cap,Ra,YZe),(Cap, Ra,YZf) (Cap,Ra,YZg),(Cap,Ra,Ya),(Cap,Ra,YZi),(Cap,Ra,YZj),(Cap,Ra,YZk),(Cap,Ra,YZl),(Cap,Ra,YZm),(Cap,Ra,YZn),(Cap,Ra,YZo),(Cap,Ra,YZp),(Cap,Ra,YZq),(Cap,Ra,YZr),(Cap,Ra,YZs),(Cap,Ra,YZt),(Cap,Ra,YZu),(Cap,Ra,YZv),(Cap,Ra,YZw),(Cap,Ra,YZx),(Cap,Ra,Y Zy), (Cap,Ra,YZz),(Cap,Ra,YZaa),(Cap,Ra,YZab),(Cap,Ra,YZac),(Cap,Ra,YZad),(Cap,Ra,Y Zae),(Cap,Ra,YZaf),(Cap,Ra,YZag),(Cap,Rb,YZa),(Cap,Rb,YZb),(Cap,Rb,YZc),(Cap,Rb,YZd),(Cap,Rb,YZe),(Cap,Rb,YZf),(Cap,Rb,YZg),(Cap,Rb,YZh),(Cap,Rb,YZi),(Cap,Rb,YZj), (Cap,Rb,YZk), (Cap,Rb,YZl), (Cap,Rb,YZm),(Cap,Rb,YZn), (Cap,Rb,YZo), (Cap,Rb,YZp), (Cap,Rb,YZq),(Cap,Rb,YZr), (Cap,Rb,YZs),(Cap,Rb,YZt),(Cap,Rb,YZu),(Cap,Rb,YZv), (Cap,Rb, YZw),(Cap,Rb,YZx),(Cap,Rb,YZy),(Cap,Rb, YZz),(Cap,Rb,YZaa),(Cap,Rb,YZab),(Cap,Rb, YZac),(Cap, Rb,YZad),(Cap,Rb,YZae),(Cap,Rb,YZaf),(Cap,Rb,YZag), (Cap,Rc,YZa),(Cap,Rc,YZb),(Cap,Rc,YZc),(Cap,Rc,YZd), (Cap,Rc,YZe),(Cap,Rc,YZf),(Cap,Rc,YZg),(Cap,Rc,YZh) (Cap,Rc,YZi),(Cap,Rc,YZj),(Cap,Rc,YZk),(Cap,Rc,YZl), (Cap,Rc,YZm),(Cap,Rc,YZn),(Cap,Rc,YZo),(Cap,Rc, YZp),(Cap,Rc,YZq),(Cap,Rc,YZr),(Cap,Rc,YZs),(Cap,Rc, YZt),(Cap,Rc,YZu),(Cap,Rc,YZv),(Cap,Rc,YZw),(Cap, Rc,YZx),(Cap,Rc,YZy),(Cap,Rc,YZz),(Cap,Rc,Y Zaa), (Cap,Rc,YZab),(Cap,Rc,YZac),(Cap,Rc,YZad),(Cap,Rc, YZae),(Cap,Rc,YZaf),(Cap,Rc, YZag),(Cap,Rd,YZa),(Cap, Rd,YZb),(Cap,Rd,YZc),(Cap,Rd,YZd),(Cap,Rd,YZe),(Cap, Rd,Y Zf),(Cap,Rd,YZg),(Cap,Rd,YZl),(Cap,Rd,YZi),(Cap, Rd,YZj),(Cap,Rd,YZk),(Cap,Rd,YZl), (Cap,Rd,YZm), (Cap,Rd,YZn),(Cap,Rd,YZo),(Cap,Rd,YZp),(Cap,Rd, YZq),(Cap,Rd,YZr),(Cap,Rd,YZs),(Cap,Rd,YZt),(Cap,Rd, YZu),(Cap,Rd,YZv),(Cap,Rd,YZw),(Cap,Rd,YZx),(Cap,Rd,YZy),(Cap,Rd,YZz),(Cap,Rd,YZaa),(Cap,Rd,YZab), (Cap,Rd,YZac),(Cap,Rd,YZad),(Cap, Rd,YZae),(Cap,Rd, YZaf),(Cap,Rd,YZag),(Cap,Re,YZa),(Cap,Re,YZb),(Cap, Re,YZc),(Cap, Re,YZd),(Cap,Re,YZe),(Cap,Re,YZf),(Cap, Re,YZg),(Cap,Re,YZh),(Cap,Re,YZi),(Cap,Re,Y Zj),(Cap, Re,YZk),(Cap,Re,YZl),(Cap,Re,YZm),(Cap,Re,YZn),(Cap, Re,YZo),(Cap,Re,YZp), (Cap,Re,YZq),(Cap,Re,YZr),(Cap, Re,YZs),(Cap,Re,YZt),(Cap,Re,YZu),(Cap,Re,YZv), (Cap,Re,YZw),(Cap,Re,YZx),(Cap,Re,YZy),(Cap,Re,YZz), (Cap,Re,YZaa),(Cap,Re,YZab),(Cap,Re,YZac),(Cap,Re, YZad),(Cap,Re,YZae),(Cap,Re,YZaf), and (Cap,Re,YZag).

Exemplary preferred compounds useful in the present invention include:

(E)-3-((1-(4-(trifluoromethoxy)phenylsulfonyl)piperidin-4-yloxyimino)methyl)benzonitrile;

3-(cyclopropyl(1-(4-(trifluoromethoxy)phenylsulfonyl)piperidin-4-yloxyimino)methyl)benzonitrile;

bis(4-fluorophenyl)methanone O-1-(4-(trifluoromethoxy) phenylsulfonyl)piperidin-4-yl oxime; and (E)-3-(1-(4-(trifluoromethoxy)phenylsulfonyl)piperidin-4-yloxyimino)ethyl)benzonitrile.

The invention disclosed herein is also meant to encompass prodrugs of the disclosed compounds. Prodrugs are considered to be any covalently bonded carriers that release the active parent drug in vivo. Non-limiting examples of prodrugs include esters or amides of compounds of Formula I, I', or I" having hydroxy or amino as a substituent, and these can be prepared by reacting such compounds with anhydrides such as succinic anhydride.

The invention disclosed herein is also meant to encompass the disclosed compounds being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively, and preferably $^3H$, $^{11}C$, and $^{14}C$. Isotopically-labeled compounds of the present invention can be prepared by methods known in the art.

The present invention is also directed specifically to $^3H$, $^{11}C$, and $^{14}C$ radiolabeled compounds of Formula I, I', or I" as well as their pharmaceutically acceptable salts, prodrugs and solvates, and the use of any such compounds as radioligands for their binding site on the calcium channel. For example, one use of the labeled compounds of the present invention is the characterization of specific receptor binding. Another use of the labeled compounds of the present invention is an alternative to animal testing for the evaluation of structure-activity relationships. For example, the receptor assay may be performed at a fixed concentration of a labeled compound of Formula I, I' or I" and at increasing concentrations of a test compound in a competition assay. For example, tritiated compounds of any of Formula I, I' or I" can be prepared by introducing tritium into the particular compound of Formula I, I' or I'", for example, by catalytic dehalogenation with tritium. This method may include reacting a suitably halogen-substituted precursor of a compound of Formula I, I' or I" with tritium gas in the presence of a suitable catalyst, for example, Pd/C, in the presence or absence of a base. Other suitable methods for preparing tritiated compounds can be found in Filer, *Isotopes in the Physical and Biomedical Sciences, Vol. 1, Labeled Compounds (Part A)*, Chapter 6 (1987). $^{14}C$-labeled compounds can be prepared by employing starting materials having a $^{14}C$ carbon.

Some of the compounds disclosed herein may contain one or more asymmetric centers and may thus give rise to enantiomers, diastereomers, and other stereoisomeric forms. The present invention is meant to encompass the uses of all such possible forms, as well as their racemic and resolved forms and mixtures thereof. The individual enantiomers may be separated according to methods known to those of ordinary skill in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

The invention disclosed herein also encompasses the use of all salts of the disclosed compounds, including all non-toxic pharmaceutically acceptable salts thereof of the disclosed compounds. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, hydrofluoride, phosphate, sulfate, nitrate and the like; organic acid salts such as citrate, lactate, tartrate, maleate, fumarate, mandelate, acetate, dichloroacetate, trifluoroacetate, oxalate, formate, succinate, and the like; sulfonates such as methanesulfonate, benzenesulfonate, p-toluenesulfonate and the like; and amino acid salts such as arginate, asparginate, glutamate and he like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts can be formed by mixing a solution of the particular compound of the present invention with a solution of a pharmaceutically acceptable non-toxic base such as sodium hydroxide, potassium hydroxide, choline hydroxide, sodium carbonate and the like.

The invention disclosed herein is also meant to encompass solvates of the disclosed compounds. One type of solvate is a hydrate. Solvates typically do not contribute significantly to the physiological activity or toxicity of the compounds and as such can function as pharmacological equivalents.

Some compounds of the present invention may have one or more of the following characteristics:

high affinity for calcium ($Ca^{2+}$) channels, especially N-type calcium channels, high selectivity to calcium ($Ca^{2+}$) channels, especially N-type calcium channels versus other channels, reduced side effect, high stability high oral absorbability, high bioavailability, low clearance, easily transfers to brain long half-life, long efficacy of a medicine and/or high protein-unbound fraction.

These compounds are considered useful as blockers of calcium($Ca^{2+}$) channels, especially N-type calcium channels.

Since compounds of Formula I, I' or I" are blockers of calcium ($Ca^{2+}$) channels, a number of diseases and conditions mediated by calcium ion influx can be treated by employing these compounds. Therefore, the present invention provides a method of treating, preventing or ameliorating stroke, neuronal damage resulting from head trauma, epilepsy, pain (e.g., acute pain, chronic pain, which includes but is not limited to, neuropathic pain and inflammatory pain or surgical pain), migraine, a mood disorder, schizophrenia, a neurodegenerative disorder (e.g., Alzheimer's disease, amyotrophic lateral sclerosis (ALS), or Parkinson's disease), depression, anxiety, a psychosis, hypertension, or cardiac arrhythmia. In one embodiment, the invention provides a method of treating pain. In another embodiment, the type of pain treated is chronic pain. In another embodiment, the type of pain treated is neuropathic pain. In another embodiment, the type of pain treated is inflammatory pain. In another embodiment, the type of pain treated is acute pain. In each instance, such method of treatment, prevention, or amelioration require administering to an animal in need of such treatment, prevention or amelioration an amount of a compound of the present invention that is therapeutically effective in achieving said treatment, prevention or amelioration. In one embodiment, the amount of such compound is the amount that is effective as to block calcium channels in vivo.

Chronic pain includes, but is not limited to, neuropathic pain, inflammatory pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

Chronic somatic pain generally results from inflammatory responses to tissue injury such as nerve entrapment, surgical procedures, cancer or arthritis (Brower, *Nature Biotechnology* 2000; 18: 387-391).

The inflammatory process is a complex series of biochemical and cellular events activated in response to tissue injury or the presence of foreign substances (Levine, Inflammatory Pain, In: Textbook of Pain, Wall and Melzack eds., 3$^{rd}$ ed., 1994).

Inflammation often occurs at the site of injured tissue, or foreign material, and contributes to the process of tissue repair and healing. The cardinal signs of inflammation include erythema (redness), heat, edema (swelling), pain and loss of function (ibid.). The majority of patients with inflammatory pain do not experience pain continually, but rather experience enhanced pain when the inflamed site is moved or touched. Inflammatory pain includes, but is not limited to, osteoarthritis and rheumatoid arthritis.

Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can also cause nerve injury. Neuropathic pain includes but is not limited to pain caused by nerve injury such as, for example, the pain from which diabetics suffer The present invention is also directed more generally to a method for treating a disorder responsive to the blockade of calcium channels, and particularly the selective blockade of N-type calcium channels, in an animal suffering from said disorder, said method comprising administering to the animal an effective amount of a compound represented by any of defined Formula I, I' or I", or a pharmaceutically acceptable salt, prodrug or solvate thereof.

The present invention is also directed to the use of a compound represented by any of defined Formula I, I' or I", or a pharmaceutically acceptable salt, prodrug or solvate thereof, in the manufacture of a medicament for treating a disorder responsive to the blockade of calcium channels in an animal suffering from said disorder. In one embodiment, the disorder is responsive to the selective blockade of N-type calcium channels.

Furthermore, the present invention is directed to a method of modulating calcium channels, especially N-type calcium channels, in an animal in need thereof, said method comprising administering to the animal at least one compound represented by any of defined Formula I, I' or I", or a pharmaceutically acceptable salt, prodrug or solvate thereof.

The present invention is also directed to the use of a compound represented by any of defined Formula I, I' or I", or a pharmaceutically acceptable salt, prodrug or solvate thereof, in the manufacture of a medicament for modulating calcium channels, especially N-type calcium channels, in an animal in need thereof.

Synthesis of Compounds

The compounds of the present invention can be prepared in a number of ways well known to those skilled in the art of organic synthesis. The compounds of the present invention can be synthesized using the methods outlined below, together with methods known in the art of synthetic organic chemistry, or variations thereof as appreciated by those skilled in the art. Preferred methods include, but are not limited to, those described below. The novel compounds of Formula I, I', or I" can be prepared using the reactions and techniques described in this section. The reactions are performed in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art. It is understood by one skilled in the art of organic synthesis that the functionality present on various portions of the starting molecule in a reaction must be compatible with the reagents and reactions proposed. Not all compounds of formula (I) falling into a given class may be compatible with some of the reaction conditions required in some of the methods described. Such restrictions to the substituents which are compatible with the reaction conditions will be readily apparent to one skilled in the art and alternative methods can be used. The compounds of formula (I) can be prepared by techniques and procedures readily available to one skilled in the art, for example by following the procedures as set forth in the following Schemes. These Schemes are not intended to limit the scope of the invention in any way. All substituents, unless otherwise indicated, are previously defined. The reagents and starting materials are readily available to one skilled in the art.

Purity of compounds was verified by LCMS measurement. LCMS methods are as follows;

(Method A) Column: Phenomemex Luna C18 (4.6×50 mm, 5 micron particle size), Temperature: 50° C., Pressure limit: 400 bar, Monitored at OD 254 nm, reference 360 nm, Flow rate: 2 ml/min.

HPLC Gradient (Buffer A=0.1% $HCO_2H/H_2O$, Buffer B=0.1% $HCO_2H/CH_3CN$)

| Time (min.) | % B |
|---|---|
| 0 | 15 |
| 1.9 | 45 |
| 4.3 | 45 |
| 8.3 | 95 |
| 11.3 | 95 |
| 11.4 | 15 |
| 15.4 | 15 |

(Method B) Column: Discovery HS C18 (4.6×150 mm, 3 micron particle size), Temperature: 25° C., Pressure limit: 400 bar, Monitored at OD 260 nm, reference 360 nm, Flow rate: 1 ml/min.

HPLC Gradient (Buffer A=0.1% $TFA/H_2O$, Buffer B=0.1% $TFA/CH_3CN$)

| Time (min.) | % B |
|---|---|
| 0 | 15 |
| 1.9 | 45 |
| 4.3 | 45 |
| 8.3 | 95 |
| 11.3 | 95 |
| 11.4 | 15 |
| 15.4 | 15 |

(Method C) Column: Phenomemex Luna C18 (4.6×50 mm, 5 micron particle size), Temperature: 50° C., Pressure limit: 344.75 bar, Monitored at OD 254 nm, Flow rate: 3 ml/min.

HPLC Gradient (Buffer A=0.1% $HCO_2H/H_2O$, Buffer B=0.1% $HCO_2H/CH_3CN$)

| Time (min.) | % B |
|---|---|
| 0 | 10 |
| 3.0 | 100 |
| 4.0 | 100 |

In order to generate compounds of general formula (I) a multi-step reaction sequence as described in Scheme 1 may be employed. Herein, a suitably N-protected 4-hydroxypiperidine or the corresponding equivalent (1a) is reacted with a suitably N-protected hydroxylamine. Typically the reaction is effected using standard "Mitsunobu-reaction" conditions, familiar to one skilled in the art, such as diethyl azodicarboxylate/triphenylphosphine. Deprotection of $P_1$ group of the compound (1b) may be accomplished using standard conditions, familiar to one skilled in the art. The acid (Z—Y—OH, Y: C=O), acid chloride (Z—Y—Cl, Y: C=O), acid anhydride (Z—Y—Z, Y: C=O) or sulfonyl chloride (Z—Y—Cl, Y: S=O) may be coupled with amine (1c) by using standard conditions, familiar to one skilled in the art. Deprotection of $P_2$ group of the compound (1d) may be accomplished using standard conditions, familiar to one skilled in the art. The resultant hydroxylamine (1e) may then be coupled with the carbonyl compound in a suitable solvent such as ethanol (EtOH) to yield the desired oxime (I). A catalyst such as acetic acid and/or elevated reaction temperature may promote this reaction.

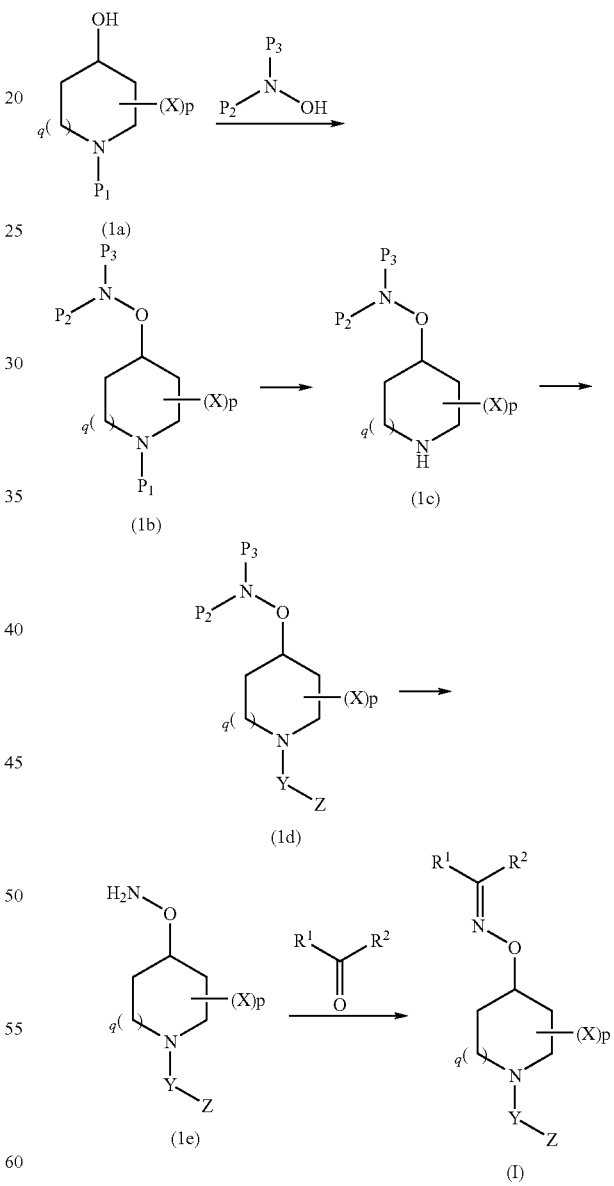

Scheme 1 wherein $P_1$ and $P_2$ are each independently an amino protecting group such as t-butoxycarbonyl and the like and $P_3$ is hydrogen, or $P_2$ and $P_3$ taken together, with the nitrogen atom to which they are attached, form phthalimide and the like, and the other symbols are the same as defined above.

An alternative way of preparing some of the compounds of the present invention is detailed in Scheme 2.

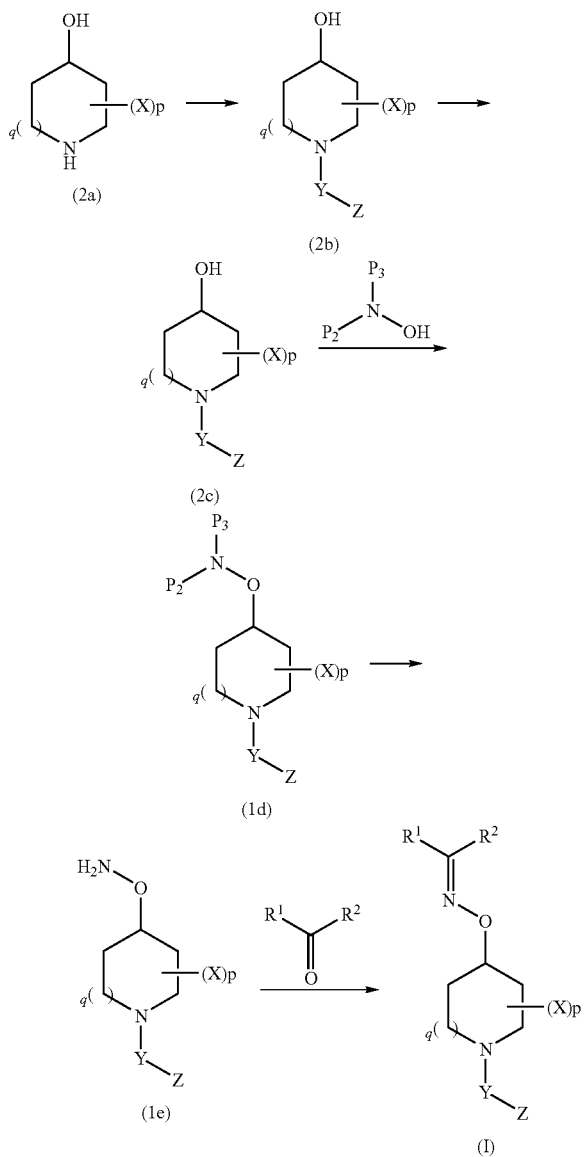

wherein $P_2$ is an amino protecting group such as t-butoxycarbonyl and the like and $P_3$ is hydrogen, or $P_2$ and $P_3$ taken together, with the nitrogen atom to which they are attached, form phthalimide and the like, and the other symbols are the same as defined above.

As an alternative to Scheme 1, Scheme 2 employs a piperidone or the corresponding equivalent (2a), which may be coupled with the acid chloride (Z—Y—Cl, Y: C=O), acid anhydride (Z—Y—Z, Y: C=O) or sulfonyl chloride (Z—Y—Cl, Y: S=O) by using standard conditions, familiar to one skilled in the art. The resultant ketone (2b) can then be reduced to the alcohol (2c). Any conventional method of reducing a ketone to an alcohol may be utilized to effect this conversion. The resulting alcohol reacts with a suitably N-protected hydroxylamine, whereby $P_2$ is, for example, tert-butoxycarbonyl. Typically the reaction is effected using standard "Mitsunobu-reaction" conditions, familiar to one skilled in the art, such as diethyl azodicarboxylate/triphenylphosphine. The resultant compound (1d) can be transformed to the compounds of formula (I) in an analogous manner to previously described in Scheme 1.

Testing of Compounds

Representative compounds of the present invention were assessed by calcium mobilization and/or electrophysiological assays for calcium channel blocker activity. One aspect of the present invention is based on the use of the compounds herein described as N-type calcium channel blockers. In one aspect of the present invention, it has been found that certain compounds herein described show selectivity as N-type calcium channel blockers. Based upon this property, these compounds are considered useful in treating, preventing, or ameliorating migraine, epilepsy, a mood disorder, schizophrenia, a neurodegenerative disorder (such as, e.g., Alzheimer's disease, ALS, or Parkinson's disease), a psychosis, depression, anxiety, hypertension, or cardiac arrhythmia. The compounds of the present invention are also expected to be effective in treating, preventing or ameliorating pain, such as acute pain, chronic pain, which includes but is not limited to, neuropathic pain and inflammatory pain or surgical pain.

More specifically, the present invention is directed to compounds of Formula I, I' or I" that are blockers of calcium channels. According to the present invention, those compounds having preferred N-type calcium channel blocking properties exhibit an $IC_{50}$ of about 100 μM or less in the calcium mobilization and/or electrophysiological assays described herein. Preferably, the compounds of the present invention exhibit an $IC_{50}$ of 10 or less. Most preferably, the compounds of the present invention exhibit an $IC_{50}$ of about 1.0 μM or less. Compounds of the present invention can be tested for their N-type and L-type $Ca^{2+}$ channel blocking activity by the following calcium mobilization and/or electrophysiological assays.

In one embodiment, compounds useful in the present invention are those represented by any one of Formula I, I' or I" that exhibit selectivity for N-type calcium channels over L-type calcium channels in the calcium mobilization and/or electrophysiological assays described herein. The phrase "selectivity for N-type calcium channels over L-type calcium channels" is used herein to mean that the ratio of an $IC_{50}$ for L-type channel blocking activity for a compound of the present invention over an $IC_{50}$ for N-type channel blocking activity for the same compound is more than 1, i.e., LTCC $IC_{50}$/NTCC $IC_{50}$>1. Preferably, compounds of the present invention exhibit an LTCC $IC_{50}$/NTCC $IC_{50}$ ratio of about 2 or more, about 10 or more, about 20 or more, about 30 or more, about 50 or more, or about 100 or more.

Calcium Mobilization and Electrophysiological Assay Protocols:

Cell maintenance and differentiation. Unless noted otherwise, cell culture reagents were purchased from Mediatech of Herndon, Md. IMR32 cells (American Type Culture Collection, ATCC, Manassas, Va.) were routinely cultured in growth medium consisting of minimum essential medium containing 10% fetal bovine serum (FBS, Hyclone, Logan, Utah), 100 U/mL penicillin, 100 μg/mL streptomycin, 2 mM L-glutamine, 1 mM sodium pyruvate, and 1×MEM non-essential amino acids. 80-90% confluent flasks of cells were differentiated using the following differentiation medium: Growth medium plus 1 mM dibutyryl cyclic AMP (Sigma, St. Louis, Mo.), and 2.5 μM bromodeoxyuridine (Sigma). Cells were differentiated for 8 days by replacing differentiation medium every 2-3 days.

A7r5 (ATCC) cells were maintained and routinely cultured in A7r5 growth medium consisting of Dulbecco's Modified Eagles Medium containing 10% FBS, 100 U/mL penicillin, 100 µg/mL streptomycin, 4 mM L-glutamine, and 0.15% sodium bicarbonate. 80-90% confluent flasks of cells were differentiated using the following differentiation medium: A7r5 Growth Medium plus 1 mM dibutyryl cyclic AMP (Sigma). Cells were differentiated for 8 days by replacing differentiation medium every 2-3 days.

Recombinant human embryonal kidney cells (HEK293, ATCC) stably transfected with either N-type calcium channel (NTCC) subunits (α1b, α2δ, and β3) or L-type calcium channel (LTCC) subunits (α1c, α2δ, and β1) were routinely cultured in growth medium consisting of Dulbecco's Modified Eagles Medium containing 10% FBS, 100 U/mL penicillin, 100 µg/mL streptomycin, 4 mM L-glutamine, 500 µg/mL geneticin (G418), 20 µg/mL Blasticidin S (InVivogen, San Diego, Calif.) and 500 µg/mL zeocin (InVivogen).

FLIPR Calcium Mobilization Assay for N-type Calcium Channel. One day prior to performing this assay, differentiated IMR32 cells were treated with 1× CellStripper, and seeded on poly-D-lysine-coated 96-well clear-bottom black plates (Becton Dickinson, Franklin Lakes, N.J.) at 200,000 cells/well. On the day of the assay, the cell plates were washed with IMR32 buffer (127 mM NaCl, 1 mM KCl, 2 mM $MgCl_2$, 700 µM $NaH_2PO_4$, 5 mM $CaCl_2$, 5 mM $NaHCO_3$, 8 mM HEPES, 10 mM glucose, pH 7.4), then pre-stimulated with KCl and loaded as follows: 0.05 mL of IMR32 buffer, 0.05 mL of each compound tested diluted in IMR32 buffer containing 20 µM nitrendipine (Sigma), and 0.1 mL KCl dissolved in IMR32 buffer, plus Fluo-4 were added (3 µM final concentration, Molecular Probes, Eugene, Oreg.). Final test compound concentrations ranged from about 846 µM to about 17 µM, final nitrendipine concentration was 5 µM, and final KCl concentration was 90 mM. After 1 hour, the cells were washed twice with 0.05 mL of each compound tested in nitrendipine-containing IMR32 buffer (no KCl or Fluo-4), and then replaced with 0.1 mL of each compound tested in nitrendipine-containing IMR32 buffer. Plates were then transferred to a Fluorimetric Imaging Plate Reader (FLIPR[96], Molecular Devices, Inc., Sunnyvale, Calif.) for assay. The FLIPR measured basal Fluo-4 fluorescence for 315 seconds (i.e., 5 minutes and 15 seconds), then added 0.1 mL KCl agonist dissolved in IMR32 buffer and measured fluorescence for another 45 seconds. Final test compound concentrations on the cells after FLIPR read ranged from about 846 pM to about 17 µM, final nitrendipine concentration was 5 µM, and final KCl concentration was 90 mM. Data were collected over the entire time course and analyzed using Excel, Graph Pad Prism (version 3.02, Graph Pad, San Diego, Calif.), or an in-house non-linear regression analysis software.

FLIPR Calcium Mobilization Assay for L-type Calcium Channel. One day prior to performing this assay, HEK293 cells stably expressing recombinant rat L-type calcium channel (LTCC) subunits (α1c, α2δ, and β1) were trypsinized, then seeded on poly-D-lysine-coated 96-well clear-bottom black plates (Becton Dickinson, Franklin Lakes, N.J.) at 75,000 cells/well. On the day of the assay, the plates were washed with LTCC wash buffer (127 mM NaCl, 2 mM $MgCl_2$, 700 µM $NaH_2PO_4$, 5 mM $CaCl_2$, 5 mM $NaHCO_3$, 8 mM HEPES, 10 mM glucose, pH 7.4), then loaded with 0.1 mL of LTCC wash buffer containing Fluo-4 (3 µM final concentration, Molecular Probes, Eugene, Oreg.). After 1 hour, the cells were washed with 0.1 mL LTCC wash buffer and resuspended in 0.05 mL LTCC assay buffer (same composition as LTCC wash buffer). Plates were then transferred to a FLIPR[96] for assay. The FLIPR measured basal Fluo-4 fluorescence for 15 seconds, then added 0.05 mL of each compound tested diluted in LTCC assay buffer at final concentrations ranging from about 846 pM to about 17 µM. Fluo-4 fluorescence was then measured for 5 minutes. 0.1 mL KCl agonist dissolved in LTCC assay buffer was then added to the cells to produce a final concentration of 90 mM KCl, and fluorescence was measured for another 45 seconds. Data were collected over the entire time course and analyzed using Excel, Graph Pad Prism, or an in-house regression analysis software.

Alternative FLIPR Calcium Mobilization Assay for L-type Calcium Channel. Alternatively, the following cell line and procedure may be used for the FLIPR calcium mobilization assay for L-type calcium channel. One day prior to performing this assay, differentiated A7r5 cells are trypsinized, then seeded on tissue culture treated 96-well clear-bottom black plates (Becton Dickinson, Franklin Lakes, N.J.) at a dilution of 1:1 from a confluent T150 $cm^2$ flask. On the day of the assay, the plates are washed with A7r5 wash buffer (127 mM NaCl, 2 mM $MgCl_2$, 700 µM $NaH_2PO_4$, 5 mM $CaCl_2$, 5 mM $NaHCO_3$, 8 mM HEPES, 10 mM glucose, pH 7.4), then loaded with 0.1 mL of A7r5 wash buffer containing Fluo-4 (3 µM final concentration, Molecular Probes, Eugene, Oreg.). After 1 hour, the cells are washed with 0.1 mL A7r5 wash buffer and resuspended in 0.05 mL A7r5 assay buffer that is composed of A7r5 wash buffer plus 50 µM valinomycin (Sigma). Plates are then transferred to a FLIPR[96] for assay. The FLIPR measures basal Fluo-4 fluorescence for 15 seconds, then adds 0.05 mL of each compound tested diluted in A7r5 assay buffer at final concentrations ranging from about 846 pM to about 17 µM. Fluo-4 fluorescence is then measured for 5 minutes. 0.1 mL KCl agonist dissolved in A7r5 assay buffer is then added to the cells to produce a final concentration of 90 mM KCl, and fluorescence was measured for another 45 seconds. Data were collected over the entire time course and analyzed using Excel, Graph Pad Prism, or an in-house regression analysis software.

Cloning of N- and L-type calcium channel subunit open reading frame cDNAs. Five cDNAs encoding subunits of the rat N- or L-type calcium channels were cloned by PCR amplification in order to reconstitute functional channels in a heterologous system. These were the alpha1b (α1b), beta1 (β1), beta3 (β3), alpha2delta (α2δ), and alpha1c (α1c) subunit cDNAs. The alpha1b subunit cDNA has been described by Dubel et al. in *Proc. Natl. Acad. Sci. U.S.A* 89: 5058-5062 (1992). The beta1 subunit cDNA has been described by Pragnell et al. in *FEBS Lett.* 291: 253-258 (1991). The beta3 subunit cDNA has been described by Castellano et al. in *J. Biol. Chem.* 268: 12359-12366 (1993). The alpha2delta subunit cDNA has been described by Kim et al. in *Proc. Natl. Acad. Sci. U.S.A.* 89: 3251-3255 (1992). The alpha1c subunit cDNA has been described by Koch et al. in *J. Biol. Chem.* 265: 17786-17791 (1990).

The 7.0 kb cDNA containing the entire α1b open reading frame (ORF) was PCR amplified as two overlapping cDNA fragments, i.e., a 2.7 kb 5' fragment and a 4.4 kb 3' fragment. The 5' fragment was amplified from rat brain cDNA using primers 1 (SEQ ID NO:1, TABLE 1) and 2 (SEQ ID NO:2, TABLE 1), and the 3' fragment was amplified from rat spinal cord cDNA using primers 3 (SEQ ID NO:3, TABLE 1) and 4 (SEQ ID NO:4, TABLE 1). The two fragments were joined by ligation at a common restriction site to create the entire 7.0 kb cDNA. This ORF encodes the protein isoform generated by alternative splicing termed "+A ΔSFMG ΔET" according to the nomenclature of Lin et al. (*Neuron* 18: 153-166 (1997)). The entire cDNA was sequenced with redundant coverage on both strands. The cDNA was then inserted into the mammalian expression vector pcDNA6.2DEST (Invitrogen, Carlsbad Calif.) by homologous recombination using the Gateway system (Invitrogen).

The 1.8 kb cDNA encoding the β1 subunit, the 1.45 cDNA encoding the beta3 subunit, and the 3.3 kb cDNA encoding the alpha2delta subunit were cloned by PCR amplification from rat spinal cord cDNA (β1) or brain cDNA (β3, α2δ). Primers 5 (SEQ ID NO:5, TABLE 1) and 6 (SEQ ID NO:6, TABLE 1) were used for the β1 cDNA amplification; primers 7 (SEQ ID NO:7, TABLE 1) and 8 (SEQ ID NO:8, TABLE 1) were used for the β3 cDNA amplification; and primers 9 (SEQ ID NO:9, TABLE 1) and 10 (SEQ ID NO:10, TABLE 1) were used for the an cDNA amplification. PCR products were subcloned and fully sequenced on both strands. Clones matching the reference sequence (β1: NM_017346; β3: NM_012828; β2δ: M86621) and the gene's GenBank rat genomic DNA sequences were recombined into the mammalian expression vector pcDNA3.2DEST (β1, β3) or pcDNA3.1-Zeo (β2δ), which had been modified to a vector compatible with the Gateway recombination system using the Gateway vector adaptor kit (Invitrogen). Proper recombination was confirmed by sequencing of recombinogenic regions. For β3 expression vector, proper protein expression was confirmed by Western blot analysis of lysates of transfected HEK293 cells using a rabbit polyclonal antiserum directed against the rat β3 subunit (USA Biological).

The 6.5 kb cDNA encoding the L-type calcium channel α1c subunit was cloned by PCR amplification from rat heart cDNA using primers 11 (SEQ ID NO:11, TABLE 1) and 12 (SEQ ID NO:12, TABLE 1). The PCR fragment was subcloned and fully sequenced on both strands to confirm its identity. A clone matching consensus reference sequence M59786 and rat genomic DNA sequences was recombined into the mammalian expression vector pcDNA6.2DEST. Sequences around the recombinogenic region were sequenced to confirm accurate recombination into the expression vector.

TABLE 1

| PRIMER SEQUENCE | SEQ ID NO. |
|---|---|
| CACC ATG GTC CGC TTC GGG GAC | 1 |
| CCG TTC AGT GGC CTC CTC C | 2 |
| C TAG CAC CAG TGA TCC TGG TCTG | 3 |
| AGT GCG TTG TGA GCG CAG TA | 4 |
| CAC CAT GGT CCA GAA GAG CGG | 5 |
| TCTCAGCGGATGTAGACGCCT | 6 |
| CAC CAT GTA TGA CGA CTC CTA C | 7 |
| GGT GGT CAG TAG CTG TCC TTA GG | 8 |
| CAC CAT GGC TGC TGG CTG CCT | 9 |
| AGA GGG TCA CCA TAG ATA GTG TCT G | 10 |
| CACCATGATTCGGGCCTTCGCT | 11 |
| AGCCTGCGGACTACAGGTTGCTGAC | 12 |

N-type Recombinant Cell Line Development. N-type calcium channel expressing HEK-293 cells were created in two stages. Stage 1 was created as follows. The rat α1b, and β3 cDNA expression constructs (2.5 μg each) were co-transfected into human embryonic kidney (HEK-293) cells by Lipofectamine Plus reagent (Invitrogen), as per manufacturer's instructions. 24 hours later, cells were split in limiting dilution into multiple 96-well plates in selection media containing 20 μg/mL blasticidin and 500 μg/mL geneticin, and incubated for 3 weeks at 37° C., 5% $CO_2$, 95% humidity. Plates containing ≤1 clone per well were cultured until wells positive for single clones were confluent. Individual clones were then arrayed into columns of a destination 96-well plate, and partly split into 6-well plates for culture maintenance. Array plates were washed once with IMR32 buffer and cells loaded for 1 hour with 0.1 mL of IMR32 buffer containing Fluo-4 (3 μM final concentration, Molecular Probes). Then they were washed twice with 0.1 mL of IMR32 buffer, and replaced with 0.1 mL IMR32 buffer. Plates were then transferred to a FLIPR[96] for assay. The FLIPR measured basal Fluo-4 fluorescence for 315 seconds, then added 0.1 mL KCl agonist dissolved in IMR32 buffer and measured fluorescence for another 45 seconds. Final KCl concentration was 90 mM. Data were collected over the entire time course and analyzed using Excel, Graph Pad Prism, or Activity Base (version 5.1, IDBS, Parsippany, N.J.) software. The clone with the greatest signal-to-noise ratio, best stability of response with passage number, and best adhesion to PDL precoated plates (Becton Dickinson) was expanded, characterized and used for stage 2 cell line development.

Stage 2 of N-type cell line development was carried out as follows. The rat α2δ cDNA expression construct (5 mg each) was transfected into the stage 1 N-type clonal cell line by Lipofectamine Plus reagent (Invitrogen), as per manufacturer's instructions. 24 hours later, cells were split in limiting dilution into multiple 96-well plates in selection media containing 20 μg/mL blasticidin, 500 μg/mL geneticin, and 250 μg/mL zeocin and incubated for 3 weeks at 37° C., 5% $CO_2$, 95% humidity. Plates containing ≤1 clone per well were cultured and handled according to the same steps and procedures described above for the stage 1 cell line. The three clones with the greatest signal-to-noise, best stability of response with passage number, and best adhesion to PDL precoated plates (Becton Dickinson) were expanded, characterized and tested in electrophysiology for the best current size, N-type pharmacology, N-type characteristic current-voltage relationship and kinetics as described below.

L-type Recombinant Cell Line Development. L-type calcium channel expressing HEK-293 cells were created in two stages. Stage 1 was created as follows. The rat α1c, and β1 cDNA expression constructs (2.5 μg each) were co-transfected into human embryonic kidney (HEK-293) cells by Lipofectamine Plus reagent (Invitrogen), as per manufacturer's instructions. 24 hours later, cells were split in limiting dilution into multiple 96-well plates in selection media containing 20 μg/mL blasticidin and 500 μg/mL geneticin, and incubated for 3 weeks at 37° C., 5% $CO_2$, 95% humidity. Plates containing 1 clone per well were cultured until wells positive for single clones were confluent. Individual clones were then arrayed into columns of a destination 96-well plate, and partly split into 6-well plates for culture maintenance. Array plates were washed once with LTCC wash (or assay) buffer and cells loaded for 1 hour with 0.1 mL of LTCC buffer containing Fluo-4 (3 μM final concentration, Molecular Probes). Then they were washed twice with 0.1 mL of LTCC buffer, and replaced with 0.1 mL LTCC buffer. Plates were then transferred to a FLIPR[96] for assay. The FLIPR measured basal Fluo-4 fluorescence for 315 seconds, then added 0.1 mL KCl agonist dissolved in LTCC buffer and measured fluorescence for another 45 seconds. Final KCl concentration was 90 mM. Data were collected over the entire time course and analyzed using Excel, Graph Pad Prism, or Activity Base software. The clone with the greatest signal-to-noise ratio, best stability of response with passage number, and best adhesion to PDL precoated plates (Becton Dickinson) was expanded, characterized and used for stage 2 cell line development.

Stage 2 of L-type cell line development was carried out as follows. The rat cDNA expression construct (5 μg each) was transfected into the stage 1 L-type clonal cell line by Lipofectamine Plus reagent (Invitrogen), as per manufacturer's instructions. 24 hours later, cells were split in limiting dilution into multiple 96-well plates in selection media containing 20 μg/mL blasticidin, 500 μg/mL geneticin, and 250 μg/mL zeocin and incubated for 3 weeks at 37° C., 5% $CO_2$, 95% humidity. Plates containing ≤1 clone per well were cultured and handled according to the same steps and procedures described above for the stage 1 cell line. The three clones with the greatest signal-to-noise, best stability of response with passage number, and best adhesion to PDL precoated plates (Becton Dickinson) were expanded and characterized.

N-type Electrophysiology in Recombinant Cells. For electrophysiological recording, the cells expressing α1b, β3 and α2δ subunits were seeded on 35-mm culture Petri dishes at a density of approximately $10^4$ cells/dish and kept in an incubator for up to three days for subsequent recordings. For recordings, the dishes were positioned on the stage of an inverted microscope (Nikon, Eclipse E600, Japan) and superfused with a bath solution comprised of $BaCl_2$ (11 mM), $MgCl_2$ (1.5 mM), HEPES (10 mM), TEA chloride (120 mM), glucose (10 mM) adjusted to pH 7.4 with KOH. Whole-cell voltage-clamp recordings were made using conventional patch-clamp techniques (Hamill et al., *Pfluegers Arch.* 391: 85-100 (1981)) at room temperature (22-24° C.). The patch-clamp pipettes were pulled from WPI, thick-walled borosilicate glass (WPI, Sarasota, Fla.). Currents were recorded using an Axopatch 200A amplifier (Axon Instruments, Union City, Calif.) and were leak-subtracted (P/4), low-pass filtered (1 kHz, 4-pole Bessel), digitized (20-50-μs intervals), and stored using Digidata 1200 B interface and Pclamp8.0/Clampex software (Axon Instruments, Union City, Calif.). The pipettes were back-filled with internal solution containing CsCl (110 mM), $MgCl_2$ (3 mM), EGTA (3 mM), HEPES (40 mM), Mg-ATP (4 mM), $Na_2GTP$ (0.5 mM), and adjusted to pH 7.2 with CsOH. The pipette resistance ranged from 2 to 3 MOhm and was compensated by 75-80% by the built-in electronic circuitry.

Currents were elicited by stepping from a holding potential of −90 mV to 0 mV for 20 ms every 20 sec. At the −90 mV membrane voltage about 50% of channels were in the inactivated state, and thus contact with a blocker would involve interaction with both resting and inactivated channels. Every drug was applied at 3 to 4 concentrations increasing in a cumulative manner. Fractional inhibition levels in steady-state were used to draw the partial inhibition concentration curves to get the $IC_{50}$ (i.e. concentration causing 50% reduction in the size of the response) values at −90 mV.

Stock solutions of each test compound were prepared using DMSO. Serial dilutions to desired concentrations were done with bath solution; concentration of DMSO in final solutions was 0.1%. Drugs were applied by gravity flow using a plane multi-barrel array shooter positioned 0.5 mm apart from the cell.

All curve fittings were carried out using Origin software (version 5.0, Microcal). A Hill equation was fit to the concentration-inhibition curves to determine $IC_{50}$ values.

N-type Electrophysiology in Neuronal Cells. To determine dissociation constants in resting versus inactivated state for N-type calcium channels, neuronal cells that endogenously express N-type calcium channels can be used. For electrophysiological recording, the neuronal cells expressing N-type calcium channels are seeded on 35-mm culture Petri dishes at a density of approximately $10^4$ cells/dish and kept in an incubator for up to three days for subsequent recordings. For recordings, the dishes are positioned on the stage of an inverted microscope (Nikon, Eclipse E600, Japan) and superfused with a bath solution comprised of $BaCl_2$ (11 mM), $MgCl_2$ (1.5 mM), HEPES (10 mM), TEA chloride (120 mM), glucose (10 mM) adjusted to pH 7.4 with KOH. Whole-cell voltage-clamp recordings are made using conventional patch-clamp techniques (Hamill et al., *Pfluegers Arch.* 391: 85-100 (1981)) at room temperature (22-24° C.). The patch-clamp pipettes are pulled from WPI, thick-walled borosilicate glass (WPI, Sarasota, Fla.). Currents are recorded using an Axopatch 200A amplifier (Axon Instruments, Union City, Calif.) and leak-subtracted (P/4), low-pass filtered (1 kHz, 4-pole Bessel), digitized (20-50-μs intervals), and stored using Digidata 1200 B interface and Pclamp8.0/Clampex software (Axon Instruments, Union City, Calif.). The pipettes are back-filled with internal solution containing CsCl (110 mM), $MgCl_2$ (3 mM), EGTA (3 mM), HEPES (40 mM), Mg-ATP (4 mM), $Na_2GTP$ (0.5 mM), and adjusted to pH 7.2 with CsOH. The pipette resistance ranges from 2 to 3 MOhm and is compensated by 75-80% by the built-in electronic circuitry.

Currents are elicited by stepping from a holding potential of −90 mV to 0 mV for 20 ms every 10 sec. At the −90 mV membrane voltage a proportion of channels is in the inactivated state, and thus contact with a blocker would involve interaction with both resting and inactivated channels. This protocol is used as a first tier screen. For dissection of two components of inhibition (resting block with the apparent dissociation constant $K_r$ and inactivated state block with KO, steady-state inactivation curves are collected using a double-pulse protocol. Three-second long depolarizing pre-pulse incrementing in 10 mV steps is followed by a 10 ms test pulse to 0 mV.

Stock solutions of each test compound are prepared using DMSO. Serial dilutions to desired concentrations are done with bath solution; concentration of DMSO in final solutions is 0.1%. Drugs are applied by gravity flow using a plane multi-barrel array shooter positioned ~1 mm apart from the cell.

All curve fittings can be carried out using Origin software (version 5.0, Microcal). A Hill equation is used to fit the concentration-response curves and to determine $IC_{50}$ values. A Boltzman equation is used to fit inactivation curves, returning half-inactivation voltage, $V_{0.5}$, slope p and the amplitude of current at the most negative voltage where eventually all channels are in the resting state. These parameters are used to calculate the apparent dissociation constants: $K_r=((Ab/Ac)/(1-(Ab/Ac))*[b])$ where [b] is the drug concentration, Ac is the maximum test current amplitude in control conditions and Ab is the maximum test current amplitude in the presence of a blocker; IC; $=[b]/((\exp(-(dx/p))*(1+([b]/K_r))-1)$ where dx is the difference between half-inactivation voltage $V_{0.5}$ in the presence and absence of drug and p is the slope.

In Vivo Pharmacology

The compounds of the present invention can be tested for in vivo anticonvulsant activity after i.v., p.o., or i.p. injection using any of a number of anticonvulsant tests in mice, including the maximum electroshock seizure test (MES). Maximum electroshock seizures are induced in male NSA mice weighing between 15-20 g and in male Sprague-Dawley rats weighing between 200-225 g by application of current (for mice: 50 mA, 60 pulses/sec, 0.8 msec pulse width, 1 sec duration, D.C.; for rats: 99 mA, 125 pulses/sec, 0.8 msec pulse width, 2 sec duration, D.C.) using a Ugo Basile ECT device (Model 7801). Mice are restrained by gripping the loose skin on their dorsal surface and saline-coated corneal electrodes are held lightly against the two corneae. Rats are allowed free movement on the bench top and ear-clip electrodes are used. Current is applied and animals are observed for a period of up to 30 seconds for the occurrence of a tonic hindlimb extensor response. A tonic seizure is defined as a hindlimb extension in excess of 90 degrees from the plane of the body. Results can be treated in a quantal manner.

The compounds can be tested for their antinociceptive activity in the formalin model as described in Hunskaar, S., O. B. Fasmer, and K. Hole, *J. Neurosci. Methods* 14: 69-76 (1985). Male Swiss Webster NIH mice (20-30 g; Harlan, San Diego, Calif.) can be used in all experiments. Food is withdrawn on the day of experiment. Mice are placed in Plexiglass jars for at least 1 hour to acclimate to the environment. Following the acclimation period mice are weighed and given either the compound of interest administered i.p. or p.o., or the appropriate volume of vehicle (10% Tween-80) as control. Fifteen minutes after the i.p. dosing, and 30 minutes after the p.o. dosing mice are injected with formalin (20 μL of 5% formaldehyde solution in saline) into the dorsal surface of the right hind paw. Mice are transferred to the Plexiglass jars and monitored for the amount of time spent licking or biting the injected paw. Periods of licking and biting are recorded in 5-minute intervals for 1 hour after the formalin injection. All experiments are done in a blinded manner during the light cycle. The early phase of the formalin response is measured as licking/biting between 0-5 minutes, and the late phase is measured from 15-50 minutes. Differences between vehicle and drug treated groups can be analyzed by one-way analysis of variance (ANOVA). A P value <0.05 is considered significant. Compounds are considered to be efficacious for treating acute and chronic pain if they have activity in blocking both the early and second phase of formalin-induced paw-licking activity.

Compounds can be tested for their potential to treat chronic pain (i.e., antiallodynic and antihyperalgesic activities) using the Chung model of peripheral neuropathy (Kim and Chung, *Pain* 50: 355-363 (1992)). Male Sprague-Dawley rats weighing between 200-225 g are anesthetized with halothane (1-3% in a mixture of 70% air and 30% oxygen), and their body temperature controlled during anesthesia through use of a homeothermic blanket. A 2-cm dorsal midline incision is then made at the L5 and L6 level, and the para-vertebral muscle groups retracted bilaterally. L5 and L6 spinal nerves are then exposed, isolated, and tightly ligated with 6-0 or 7-0 silk suture. A sham operation is performed exposing the contralateral L5 and L6 spinal nerves, without ligating, as a negative control.

Tactile Allodynia: Sensitivity to non-noxious mechanical stimuli can be measured in animals to assess tactile allodynia. Rats are transferred to an elevated testing cage with a wire mesh floor and allowed to acclimate for five to ten minutes. A series of von Frey monofilaments are applied to the plantar surface of the hindpaw to determine the animal's withdrawal threshold. The first filament used possesses a buckling weight of 9.1 gms (0.96 log value) and is applied up to five times to see if it elicits a withdrawal response. If the animal has a withdrawal response, then the next lightest filament in the series would be applied up to five times to determine if it also could elicit a response. This procedure is repeated with subsequent lesser filaments until there is no response and the identity of the lightest filament that elicits a response is recorded. If the animal does not have a withdrawal response from the initial 9.1 gms filament, then subsequent filaments of increased weight are applied until a filament elicits a response and the identity of this filament is recorded. For each animal, three measurements are made at every time point to produce an average withdrawal threshold determination. Tests can be performed prior to, and at 1, 2, 4 and 24 hours post drug administration.

Mechanical Hyperalgesia: Sensitivity to noxious mechanical stimuli can be measured in animals using the paw pressure test to assess mechanical hyperalgesia. In rats, hind paw withdrawal thresholds ("PWT"), measured in grams, in response to a noxious mechanical stimulus are determined using an analgesymeter (Model 7200, commercially available from Ugo Basile of Italy), as described in Stein (*Biochemistry & Behavior* 31: 451-455 (1988)). The rat's paw is placed on a small platform, and weight is applied in a graded manner up to a maximum of 250 grams. The endpoint is taken as the weight at which the paw is completely withdrawn. PWT is determined once for each rat at each time point. PWT can be measured only in the injured paw, or in both the injured and non-injured paw. In one non-limiting embodiment, mechanical hyperalgesia associated with nerve injury induced pain (neuropathic pain) can be assessed in rats. Rats are tested prior to surgery to determine a baseline, or normal, PWT. Rats are tested again 2 to 3 weeks post-surgery, prior to, and at different times after (e.g. 1, 3, 5 and 24 hr) drug administration. An increase in PWT following drug administration indicates that the test compound reduces mechanical hyperalgesia.

Pharmaceutical Compositions

Although a compound of the present invention may be administered to a mammal in the form of a raw chemical without any other components present, the compound is preferably administered as part of a pharmaceutical composition containing the compound combined with a suitable pharmaceutically acceptable carrier. Such a carrier can be selected from pharmaceutically acceptable excipients and auxiliaries.

Compositions within the scope of the present invention include all compositions where a compound of the present invention is combined with a pharmaceutically acceptable carrier. In a preferred embodiment, the compound is present in the composition in an amount that is effective to achieve its intended therapeutic purpose. While individual needs may vary, a determination of optimal ranges of effective amounts of each compound is within the skill of the art. Typically, the compounds may be administered to mammal, e.g. human, orally at a dose of from about 0.0025 to about 1500 mg per kg body weight of the mammal, or an equivalent amount of a pharmaceutically acceptable salt thereof, per day to treat the particular disorder. A useful oral dose of a compound of the present invention administered to a mammal is from about 0.0025 to about 50 mg per kg body weight of the mammal, or an equivalent amount of the pharmaceutically acceptable salt thereof. For intramuscular injection, the dose is typically about one-half of the oral dose.

A unit oral dose may comprise from about 0.01 to about 50 mg, and preferably about 0.1 to about 10 mg, of the compound. The unit dose can be administered one or more times daily as one or more tablets, each containing from about 0.01 to about 50 mg of the compound, or an equivalent amount of a pharmaceutically acceptable salt or solvate thereof.

In one embodiment, a pharmaceutical composition of the present invention can be administered orally and is formulated into tablets, dragees, capsules or an oral liquid preparation.

Alternatively, a pharmaceutical composition of the present invention can be administered rectally, and is formulated in suppositories.

Alternatively, a pharmaceutical composition of the present invention can be administered by injection.

Alternatively, a pharmaceutical composition of the present invention can be administered transdermally.

Alternatively, a pharmaceutical composition of the present invention can be administered by inhalation or by intranasal administration.

Alternatively, a pharmaceutical composition of the present invention can be administered by the intravaginal route.

A pharmaceutical composition of the present invention can contain from about 0.01 to 99 percent by weight, and preferably from about 0.25 to 75 percent by weight, of active compound(s).

The present methods of the invention, such as the method for treating, preventing, or ameliorating a disorder responsive to the blockade of calcium channels in an animal in need thereof, can further comprise administering a second therapeutic agent to the animal being administered a compound of Formula I, I' or I''. In one embodiment, the second therapeutic agent is administered in an effective amount.

Effective amounts of the other therapeutic agents are known to those skilled in the art. However, it is well within the skilled artisan's purview to determine the other therapeutic agent's optimal effective-amount range. In one embodiment of the invention, where another therapeutic agent is administered to an animal, the effective amount of the compound of the present invention is less than its effective amount would be where the other therapeutic agent is not administered. In this case, without being bound by theory, it is believed that compounds of the present invention and the other therapeutic agent act synergistically to treat, prevent, or ameliorate a disorder or condition.

The second therapeutic agent can be, but is not limited to, an opioid agonist, a non-opioid analgesic, a non-steroidal anti-inflammatory agent, an antimigraine agent, a Cox-II inhibitor, a β-adrenergic blocker, an anticonvulsant, an antidepressant, an anticancer agent, an agent for treating addictive disorder, an agent for treating Parkinson's disease and parkinsonism, an agent for treating anxiety, an agent for treating epilepsy, an agent for treating a seizure, an agent for treating a stroke, an agent for treating a pruritic condition, an agent for treating psychosis, an agent for treating ALS, an agent for treating a cognitive disorder, an agent for treating a migraine, an agent for treating vomiting, an agent for treating dyskinesia, or an agent for treating depression, and mixtures thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Examples of other suitable non-opioid analgesics include the following, non limiting, chemical classes of analgesic, antipyretic, nonsteroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic Antipyretic and Antiinflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9th ed 1996) and Glen R. Hanson, *Analgesic, Antipyretic and Anti Inflammatory Drugs* in Remington: *The Science and Practice of Pharmacy* Vol II 1196-1221 (A. R. Gennaro ed. 19th ed. 1995) which are hereby incorporated by reference in their entireties. Suitable Cox-II inhibitors and 5-lipoxygenase inhibitors, as well as combinations thereof, are described in U.S. Pat. No. 6,136,839, which is hereby incorporated by reference in its entirety. Examples of useful Cox II inhibitors include, but are not limited to, rofecoxib and celecoxib.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, and cisplatin.

Therapeutic agents useful for treating or preventing an addictive disorder include, but are not limited to, methadone, desipramine, amantadine, fluoxetine, buprenorphine, an opiate agonist, 3-phenoxypyridine, or a serotonin antagonist.

Examples of useful therapeutic agents for treating or preventing Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating or preventing epilepsy or seizure include, but are not limited to, carbamazepine, ethosuximide, gabapentin, lamotrigine, phenobarbital, phenyloin, primidone, valproic acid, trimethadione, benzodiazepines, gamma-vinyl GABA, acetazolamide, and felbamate.

Examples of useful therapeutic agents for treating or preventing stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating or preventing a pruritic condition include, but are not limited to, naltrexone; nalmefene; danazol; tricyclics such as amitriptyline, imipramine, and doxepin; antidepressants such as those given below; menthol; camphor; phenol; pramoxine; capsaicin; tar; steroids; and antihistamines.

Examples of useful therapeutic agents for treating or preventing psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating or preventing ALS include, but are not limited to, baclofen, neurotrophic factors, riluzole, tizanidine, benzodiazepines such as clonazepan and dantrolene.

Examples of useful therapeutic agents for treating or preventing cognitive disorders include, but are not limited to, agents for treating or preventing dementia such as tacrine; donepezil; ibuprofen; antipsychotic drugs such as thioridazine and haloperidol; and antidepressant drugs such as those given below.

Examples of useful therapeutic agents for treating or preventing a migraine include, but are not limited to, sumatriptan; methysergide; ergotamine; caffeine; and beta-blockers such as propranolol, verapamil, and divalproex.

Examples of useful therapeutic agents for treating or preventing vomiting include, but are not limited to, 5-HT3 receptor antagonists such as odansetron, dolasetron, granisetron, and tropisetron; dopamine receptor antagonists such as prochlorperazine, thiethylperazine, chlorpromazine, metoclopramide, and domperidone; glucocorticoids such as dexamethasone; and benzodiazepines such as lorazepam and alprazolam.

Examples of useful therapeutic agents for treating or preventing dyskinesia include, but are not limited to, reserpine and tetrabenazine.

Examples of useful therapeutic agents for treating or preventing depression include, but are not limited to, tricyclic antidepressants such as amitryptyline, amoxapine, bupropion, clomipramine, desipramine, doxepin, imipramine, maprotiline, nefazadone, nortriptyline, protriptyline, trazodone, trimipramine, and venlafaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A compound of the present invention and the second therapeutic agent can act additively or, in one embodiment, synergistically. In one embodiment, a compound of the present invention is administered concurrently with the second therapeutic agent; for example, a composition comprising an effective amount of a compound of Formula I, I' or I", and an effective amount of a second therapeutic agent can be administered. Alternatively, a composition comprising an effective amount of a compound of Formula I, I' or I" and a different composition comprising an effective amount of a second therapeutic agent can be concurrently administered. In another embodiment, an effective amount of a compound of the present invention is administered prior or subsequent to administration of an effective amount of the second therapeutic agent. In this embodiment, the compound of the present invention is administered while the second therapeutic agent exerts its therapeutic effect, or the other therapeutic agent is administered while the compound of the present invention exerts its preventive or therapeutic effect for treating, ameliorating or preventing a disorder or condition.

A pharmaceutical composition of the present invention can be administered to any animal that may experience the beneficial effects of a compound of the present invention. Foremost among such animals are mammals, e.g., humans and companion animals, although the invention is not intended to be so limited.

A pharmaceutical composition of the present invention can be administered by any means that achieves its intended purpose. For example, administration can be by the parenteral, subcutaneous, intravenous, intramuscular, intraperitoneal, transdermal, intranasal, rectal, intravaginal or buccal route, or by inhalation. Alternatively, or concurrently, administration can be by the oral route. The dosage administered and route of administration will vary, depending upon the circumstances of the particular subject, and taking into account such factors as age, health, and weight of the recipient, condition or disorder to be treated, kind of concurrent treatment, if any, frequency of treatment, and the nature of the effect desired.

A pharmaceutical composition of the present invention is preferably manufactured in a manner which is itself known, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate can be used. Dye stuffs or pigments may be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which may be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers may be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound may be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

The following examples are illustrative, but not limiting, of the compounds, compositions and methods of the present invention. Suitable modifications and adaptations of the variety of conditions and parameters normally encountered in clinical therapy and which are obvious to those skilled in the art in view of this disclosure are within the spirit and scope of the invention.

EXAMPLES

Example 1

(E)-3-((1-(4-(Trifluoromethoxy)phenylsulfonyl)piperidin-4-yloxyimino)methyl)benzonitrile

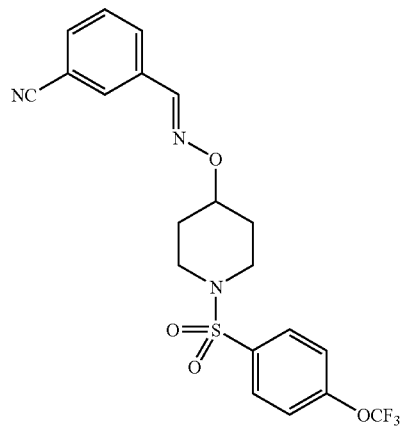

a) Diethyl azodicarboxylate (40% in toluene, 2.5 ml, 5.5 mmol) was added to the mixture of N-Boc-4-hydroxypiperidine (1.0 g, 5.0 mmol), N-hydroxyphthalimide (816 mg, 5.0 mmol) and triphenylphosphine (1.3 g, 5.0 mmol) in THF (10 ml) at 0° C. and stirred at room temperature for 1.5 hours. The solvent was evaporated under reduced pressure and the residue was diluted with ethyl acetate and washed with water and brine, dried (MgSO$_4$) and evaporated under reduced pressure. The residue was purified by column chromatography on silica (EtOAc/Hexanes 30/70-70/30) to give tert-butyl 4-(1,3-dioxoisoindolin-2-yloxy)piperidine-1-carboxylate (1.37 g, 80%).

b) Hydrogen chloride in 1,4-dioxane (4 M, 7.0 ml) was added to the solution of tert-butyl 4-(1,3-dioxoisoindolin-2-yloxy)piperidine-1-carboxylate (692 mg, 2.00 mmol) in 1,4-dioxane (4 ml) and stirred for 1 hour. The precipitated material was collected, washed with n-hexane (2 ml×2) and dried under reduced pressure at 80° C. to give 2-(piperidin-4-yloxy)isoindoline-1,3-dione hydrochloride (533 mg, 94%).

c) A suspension of 2-(piperidin-4-yloxy)isoindoline-1,3-dione hydrochloride (533 mg, 1.9 mmol) and diisopropylethylamine (0.97 ml, 5.7 mmol) in DMF (5 ml) was stirred at 80° C. for 30 minutes and the resulted solution was cooled at 0° C. To this ice-cooled solution, a solution of 4-trifluoromethoxysulfonyl chloride (589 mg, 2.1 mmol) in DMF (2 ml) was added dropwise over 10 minutes and the whole was stirred at room temperature for 30 minutes. The reaction mixture was diluted with ethyl acetate and washed with water (×3) and brine, dried (MgSO$_4$) and evaporated under reduced pressure. The residue was purified by column chromatography on silica (EtOAc/Hexanes 20/80-50/50) to give 2-(1-(4-(trifluoromethoxy)phenylsulfonyl)piperidin-4-yloxy)isoindoline-1,3-dione (749 mg, 84%).

d) A mixture of 2-(1-(4-(trifluoromethoxy)phenylsulfonyl)piperidin-4-yloxy)isoindoline-1,3-dione (640 mg, 1.36 mmol) and hydrazine monohydrate (0.073 ml, 1.5 mmol) in EtOH (6 ml) was stirred for 1 hour. The precipitated materials were filtered off and washed with EtOH (2 ml×2), then the filtrate was evaporated under reduced pressure to give O-(1-(4-(trifluoromethoxy)phenylsulfonyl)piperidin-4-yl)hydroxylamine (519 mg, 100%).

e) A solution of O-(1-(4-(trifluoromethoxy)phenylsulfonyl)piperidin-4-yl)hydroxylamine (130 mg, 0.38 mmol), 3-formylbenzonitrile (45 mg, 0.38 mmol) and acetic acid (0.022 ml, 0.38 mmol) in EtOH (4 ml) was stirred for 1 hour and the solvent was evaporated under reduced pressure. The residue was purified by column chromatography on silica (EtOAc/Hexanes 20/80-50/50) and recrystallized from EtOAc/Hexanes to give (E)-3-((1-(4-(trifluoromethoxy)phenylsulfonyl)piperidin-4-yloxyimino)methyl)benzonitrile (96 mg, 56%, colorless solid, LC: 98%, retention time: 7.94 min (Method A), M/Z: 453.

$^1$H-NMR (DMSO-d$_6$) δ: 8.27 (1H, s), 7.99 (1H, s), 7.85-7.96 (4H, m), 7.59-7.68 (3H, m), 4.25 (1H, m), 3.28 (2H, m), 2.89 (2H, m), 2.01 (2H, m), 1.74 (2H, m).

Example 2

3-(Cyclopropyl(1-(4-(trifluoromethoxy)phenylsulfonyl)piperidin-4-yloxyimino)methyl)benzonitrile

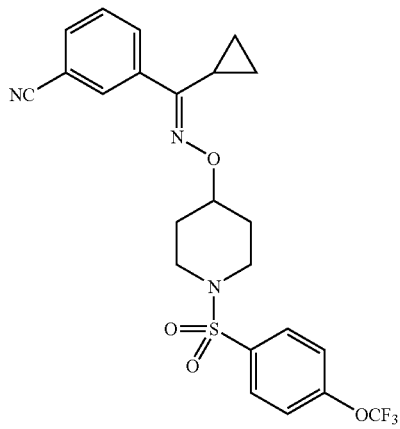

The key intermediate 3-(Cyclopropanecarbonyl)benzonitrile was prepared as follows;

a) Cyclopropylmagnesium bromide (1M in THF, 6 ml, 6 mmol) was added to a solution of 3-formylbenzonitrile in THF (12 ml) at −78° C. and stirred at 0° C. for 5 hours. The reaction was quenched with saturated NH$_4$Cl solution (30 ml), extracted with EtOAc, washed with water (×2) and brine, dried (MgSO$_4$) and evaporated under reduced pressure. The residue was purified by column chromatography on silica (EtOAc/Hexanes 20/80-50/50) to give 3-(cyclopropyl(hydroxy)methyl)benzonitrile (778 mg, 91%).

b) 2-Iodoxybenzoic acid (IBX) was added to a solution of 3-(cyclopropyl(hydroxy)methyl)benzonitrile (171 mg, 1 mmol) in EtOAc (5 ml) at room temperature and stirred at 80° C. for 2 hours. After cooling to 0° C., the precipitated materials were filtered off and washed with EtOAc (3 ml×2), then the filtrate was evaporated under reduced pressure. The residue was purified by column chromatography on silica (EtOAc/Hexanes 5/95-30/70) to give 3-(cyclopropanecarbonyl)benzonitrile (225 mg, 100%).

3-(Cyclopropanecarbonyl)benzonitrile was coupled with O-(1-(4-(trifluoromethoxy)phenylsulfonyl)piperidin-4-yl) hydroxylamine to give 3-(cyclopropyl(1-(4-(trifluoromethoxy)phenylsulfonyl)piperidin-4-yloxyimino)methyl) benzonitrile as a mixture of stereoisomers.

Colorless oil, LC: 100%, retention time: 8.20 min (Method A), M/Z: 493.

$^1$H-NMR (DMSO-d$_6$) δ: 7.43-7.95 (8H, m), 4.05-4.30 (1H, m), 2.77-3.13 (4H, m), 1.58-2.00 (5H, m), 0.66-0.82 (2H, m), 0.43 (1H, m).

Example 3

Bis(4-fluorophenyl)methanone O-1-(4-(trifluoromethoxy)phenylsulfonyl)piperidin-4-yl oxime

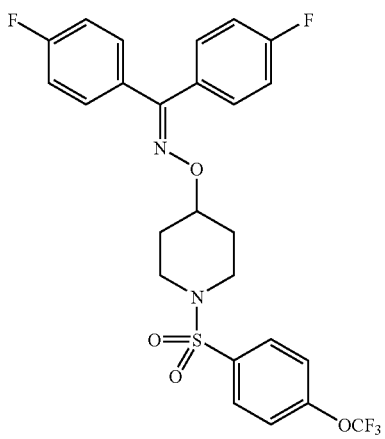 [SMILES: O=S(=O)(c1ccc(OC(F)(F)F)cc1)N1CCC(ON=C(c2ccc(F)cc2)c2ccc(F)cc2)CC1]

a) A suspension of 4-piperidone monohydrate hydrochloride (5.0 g, 33 mmol) and diisopropylethylamine (17 ml, 98 mmol) in DMF (200 ml) was stirred at 80° C. for 30 minutes and the resulted solution was cooled at 0° C. To this ice-cooled solution, a solution of 4-trifluoromethoxysulfonyl chloride (11.0 g, 39 mmol) in DMF (40 ml) was added dropwise and the whole was stirred at room temperature overnight. The solvent was evaporated under reduced pressure and ice-water (80 ml) was added to the residue. The precipitated material was collected, washed with water (50 ml×3) and n-hexane (30 ml) and dried under reduced pressure at 80° C. to give 1-(4-(trifluoromethoxy)phenylsulfonyl)piperidin-4-one (9.8 g, 93%).

b) NaBH$_4$ was added to a solution of 1-(4-(trifluoromethoxy)phenylsulfonyl)piperidin-4-one (1.0 g, 3.0 mmol) in MeOH (15 ml) at 0° C. and stirred at 0° C. for 45 minutes. The reaction was quenched with water (30 ml) and hydrochloric acid (2 M, 5 ml), extracted with EtOAc, washed with water (×2) and brine, dried (MgSO$_4$) and evaporated under reduced pressure to give 1-(4-(trifluoromethoxy)phenylsulfonyl)piperidin-4-ol (1.0 g, 100%).

c) Diethyl azodicarboxylate (40% in toluene, 1.0 ml, 2.2 mmol) was added to the mixture of 1-(4-(trifluoromethoxy)phenylsulfonyl)piperidin-4-ol (651 mg, 2.0 mmol), N-hydroxyphthalimide (359 mg, 2.2 mmol) and triphenylphosphine (577 mg, 2.2 mmol) in THF (8 ml) at 0° C. and stirred at room temperature for 2 days. The solvent was evaporated under reduced pressure and the residue was purified by column chromatography on silica (EtOAc/Hexanes 10/90-50/50) to give 2-(1-(4-(trifluoromethoxy)phenylsulfonyl)piperidin-4-yloxy)isoindoline-1,3-dione (390 mg, 40%).

d) A mixture of 2-(1-(4-(trifluoromethoxy)phenylsulfonyl)piperidin-4-yloxy)isoindoline-1,3-dione (390 mg, 0.82 mmol) and hydrazine monohydrate (0.044 ml, 0.90 mmol) in EtOH (4 ml) was stirred for 1 hour. The precipitated materials were filtered off and washed with EtOH (2 ml×2), then the filtrate was evaporated under reduced pressure to give O-(1-(4-(trifluoromethoxy)phenylsulfonyl)piperidin-4-yl)hydroxylamine (279 mg, 100%).

e) A solution of O-(1-(4-(trifluoromethoxy)phenylsulfonyl)piperidin-4-yl)hydroxylamine (130 mg, 0.38 mmol), 4,4'-difluorobenzophenone (83 mg, 0.38 mmol) and acetic acid (0.021 ml, 0.38 mmol) in EtOH (4 ml) was stirred at 100° C. for 2 days and the solvent was evaporated under reduced pressure. The residue was purified by column chromatography on silica (EtOAc/Hexanes 1/99-20/80) to give bis(4-fluorophenyl)methanone O-1-(4-(trifluoromethoxy)phenylsulfonyl)piperidin-4-yl oxime (103 mg, 50%, colorless oil, LC: 95%, retention time: 8.87 min (Method A), M/Z: 540.

$^1$H-NMR (DMSO-d$_6$) δ: 7.87 (2H, d, 8.0 Hz), 7.66 (2H, d, 8.0 Hz), 7.38 (2H, m), 7.22 (4H, m), 7.10 (2H, m), 4.33 (1H, m), 3.08 (2H, m), 2.74 (2H, m), 1.89 (2H, m), 1.78 (2H, m).

Similarly, the following compounds were prepared

Example 4

(E)-3-(1-(1-(4-(Trifluoromethoxy)phenylsulfonyl)piperidin-4-yloxyimino)ethyl)benzonitrile

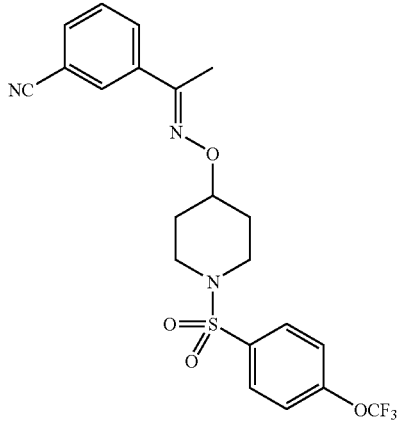

Colorless solid, LC: 97%, retention time: 8.35 min (Method A), M/Z: 467.

$^1$H-NMR (DMSO-d$_6$) δ: 8.05 (1H, s), 7.99 (1H, s), 7.84-7.98 (4H, m), 7.57-7.69 (3H, m), 4.28 (1H, m), 3.16 (2H, m), 2.93 (2H, m), 2.08 (3H, s), 1.91 (2H, m), 1.77 (2H, m).

Compounds of the invention have been tested in the calcium mobilization and/or electrophysiological assay for N-type calcium channel blocking activity, which are described in detail above. Some compounds described have also been tested in the calcium mobilization assay for L-type calcium channel blocking activity, which is described in detail above. Representative values are presented in TABLE 2.

TABLE 2

Evaluation of the tested compounds as N-type calcium channel (NTCC) blockers and L-type calcium channel (LTCC) blockers after a calcium mobilization in vitro assay

| Example Number | Compound Name | NTCC IC$_{50}$ (nM) | LTCC IC$_{50}$ (nM) |
|---|---|---|---|
| 2 | 3-(Cyclopropyl(1-(4-(trifluoromethoxy)-phenylsulfonyl)piperidin-4-yloxyimino)methyl)benzonitrile | 200 | >20000 |
| 3 | Bis(4-fluorophenyl)methanone O-1-(4-(trifluoromethoxy)phenylsulfonyl)-piperidin-4-yl oxime | 100 | >20000 |

TABLE 2-continued

Evaluation of the tested compounds as N-type calcium channel (NTCC) blockers and L-type calcium channel (LTCC) blockers after a calcium mobilization in vitro assay

| Example Number | Compound Name | NTCC IC$_{50}$ (nM) | LTCC IC$_{50}$ (nM) |
|---|---|---|---|
| 4 | (E)-3-(1-(1-(4-(Trifluoromethoxy)phenylsulfonyl)-piperidin-4-yloxyimino)ethyl)benzonitrile | 180 | >20000 |

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:

1. A compound having the Formula I:

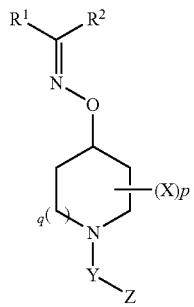

or a pharmaceutically acceptable salt, thereof wherein:
Y is CO or $SO_m$;
Z is optionally substituted aryl or optionally substituted heterocyclyl;
$R^1$ and $R^2$ are each independently hydrogen, optionally substituted lower alkyl, optionally substituted lower alkenyl, optionally substituted lower alkynyl, optionally substituted cycloalkyl, optionally substituted cycloalkenyl, optionally substituted aryl, optionally substituted heterocyclyl, cyano, $COR^5$, or $CONR^5R^6$, or
$R^1$ and $R^2$ taken together, with the carbon atom to which they are attached, form optionally substituted cycloalkyl, optionally substituted bicycloalkyl, optionally substituted cycloalkenyl or optionally substituted heterocyclyl;
$R^5$ and $R^6$ are each independently hydrogen, optionally substituted lower alkyl, optionally substituted lower alkenyl, optionally substituted lower alkynyl, optionally substituted cycloalkyl, optionally substituted bicycloalkyl, optionally substituted cycloalkenyl, optionally substituted aryl or optionally substituted heterocyclyl;
each X is independently =O, optionally substituted lower alkyl, optionally substituted lower alkenyl, optionally substituted lower alkynyl, halogen, cyano, nitro, $NR^5R^6$, $OR^5$, $SR^5$, $COR^5$, $COOR^5$, $CONR^5R^6$, $NR^5COR^5$, $OCOR^5$, $SOR^5$, $SO_2R^5$, $SO_3R^5$, $SONR^5R^6$, $SO_2NR^5R^6$, $NR^5SOR^5$, or $NR^5SO_2R^5$;
m is 1 or 2; and
p is 0, 1 or 2;
provided that:
when $R^1$ is aminothiazolyl, $R^2$ is $CONHR^6$, wherein $R^6$ is optionally substituted heterocyclyl and Y is CO, then Z is not 4-nitrobenzyloxy.

2. The compound of claim 1, wherein Y is $SO_2$.

3. A compound having the Formula I as claimed in claim 1 or 2, wherein the compound is $^3H$ radiolabeled.

4. A pharmaceutical composition for modulating calcium channels in a mammal, comprising the compound having the Formula I':

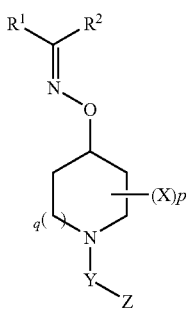

or a pharmaceutically acceptable salt thereof, wherein:
Y is CO or $SO_m$;
Z is optionally substituted heterocyclyl;
$R^1$ and $R^2$ are each independently hydrogen, optionally substituted lower alkyl, optionally substituted lower alkenyl, optionally substituted lower alkynyl, optionally substituted cycloalkyl, optionally substituted cycloalkenyl, optionally substituted aryl, optionally substituted heterocyclyl, cyano, $COR^5$, or $CONR^5R^6$, or
$R^1$ and $R^2$ taken together, with the carbon atom to which they are attached, form optionally substituted cycloalkyl, optionally substituted bicycloalkyl, optionally substituted cycloalkenyl or optionally substituted heterocyclyl;
$R^5$ and $R^6$ are each independently hydrogen, optionally substituted lower alkyl, optionally substituted lower alkenyl, optionally substituted lower alkynyl, optionally substituted cycloalkyl, optionally substituted bicycloalkyl, optionally substituted cycloalkenyl, optionally substituted aryl or optionally substituted heterocyclyl;
each X is independently =O, optionally substituted lower alkyl, optionally substituted lower alkenyl, optionally substituted lower alkynyl, halogen, cyano, nitro, $NR^5R^6$, $OR^5$, $SR^5$, $COR^5$, $COOR^5$, $CONR^5R^6$, $NR^5COR^5$, $OCOR^5$, $SOR^5$, $SO_2R^5$, $SO_3R^5 SONR^5R^6$, $SO_2NR^5R^6$, $NR^5SOR^5$, or $NR^5SO_2R^5$;
m is 1 or 2; and
p is 0, 1 or 2;

provided that:
when $R^1$ is aminothiazolyl, $R^2$ is $CONHR^6$, wherein $R^6$ is optionally substituted heterocyclyl and Y is CO, then Z is not 4-nitrobenzyloxy;
and a pharmaceutically acceptable carrier.

5. The compound of claim 4, wherein Y is $SO_2$.

6. A compound having the Formula I as claimed in claim 1 or 2, wherein the compound is $^{11}C$ radiolabeled.

7. A compound having the Formula I as claimed in claim 1 or 2, wherein the compound is $^{14}C$ radiolabeled.

* * * * *